(12) United States Patent
Shiono et al.

(10) Patent No.: US 8,742,038 B2
(45) Date of Patent: Jun. 3, 2014

(54) RESIST COMPOSITION FOR IMMERSION EXPOSURE, METHOD OF FORMING RESIST PATTERN USING THE SAME, AND FLUORINE-CONTAINING COMPOUND

(75) Inventors: Daiju Shiono, Kawasaki (JP); Takahiro Dazai, Kawasaki (JP); Sanae Furuya, Kawasaki (JP); Tomoyuki Hirano, Kawasaki (JP); Takayoshi Mori, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 341 days.

(21) Appl. No.: 12/360,415

(22) Filed: Jan. 27, 2009

(65) Prior Publication Data
US 2009/0197204 A1   Aug. 6, 2009

(30) Foreign Application Priority Data

Feb. 6, 2008  (JP) ................ 2008-027045
Apr. 7, 2008  (JP) ................ 2008-099826
Jun. 23, 2008 (JP) ................ 2008-163862
Dec. 12, 2008 (JP) ................ 2008-317487

(51) Int. Cl.
C08G 61/04 (2006.01)
C07C 69/52 (2006.01)

(52) U.S. Cl.
USPC .......................................... 526/72; 560/223

(58) Field of Classification Search
None
See application file for complete search history.

(56) References Cited

U.S. PATENT DOCUMENTS

| | | | |
|---|---|---|---|
| 4,495,275 A * | 1/1985 | Yokoyama et al. | 430/527 |
| 4,638,024 A | 1/1987 | Sato et al. | |
| 4,828,952 A * | 5/1989 | Kato et al. | 430/87 |
| 5,580,694 A | 12/1996 | Allen et al. | |
| 5,945,517 A | 8/1999 | Nitta et al. | |
| 6,153,733 A | 11/2000 | Yukawa et al. | |
| 6,165,678 A | 12/2000 | Allen et al. | |
| 6,255,392 B1 | 7/2001 | Inoue et al. | |
| 6,686,429 B2 | 2/2004 | Dammel et al. | |
| 7,074,543 B2 | 7/2006 | Iwai et al. | |
| 7,291,690 B2 | 11/2007 | Yamago et al. | |
| 7,354,693 B2 | 4/2008 | Hatakeyama et al. | |
| 7,459,261 B2 | 12/2008 | Hatakeyama et al. | |
| 7,482,108 B2 | 1/2009 | Matsumaru et al. | |
| 7,867,697 B2 | 1/2011 | Kodama | |
| 8,039,199 B2 | 10/2011 | Abe | |
| 8,048,612 B2 | 11/2011 | Fuji et al. | |
| 8,053,161 B2 | 11/2011 | Wada et al. | |
| 8,192,915 B2 | 6/2012 | Dazai et al. | |
| 8,221,956 B2 | 7/2012 | Shiono et al. | |
| 2005/0014090 A1 | 1/2005 | Hirayama et al. | |
| 2005/0019690 A1 | 1/2005 | Kodama | |
| 2005/0271978 A1 | 12/2005 | Takeda et al. | |
| 2006/0008736 A1 | 1/2006 | Kanda et al. | |
| 2006/0029884 A1 | 2/2006 | Hatakeyama et al. | |
| 2006/0110677 A1 | 5/2006 | Houlihan et al. | |
| 2006/0246373 A1 | 11/2006 | Wang | |
| 2006/0269871 A1 | 11/2006 | Harada et al. | |
| 2007/0160929 A1 | 7/2007 | Hasegawa et al. | |
| 2007/0172769 A1 | 7/2007 | Kanna et al. | |
| 2007/0219338 A1 | 9/2007 | Takeda et al. | |
| 2007/0231708 A1 | 10/2007 | Matsumaru et al. | |
| 2007/0231738 A1 | 10/2007 | Kaneko et al. | |
| 2007/0254235 A1 | 11/2007 | Allen et al. | |
| 2007/0298352 A1 | 12/2007 | Kobayashi et al. | |
| 2007/0298355 A1 | 12/2007 | Harada et al. | |
| 2008/0008961 A1 | 1/2008 | Nishi et al. | |
| 2008/0081290 A1 | 4/2008 | Wada et al. | |
| 2008/0090171 A1 | 4/2008 | Irie et al. | |
| 2008/0102407 A1 | 5/2008 | Ohsawa et al. | |
| 2008/0118860 A1 | 5/2008 | Harada et al. | |
| 2008/0153030 A1 | 6/2008 | Kobayashi et al. | |
| 2008/0193879 A1 | 8/2008 | Allen et al. | |
| 2008/0311507 A1 | 12/2008 | Isono et al. | |

(Continued)

FOREIGN PATENT DOCUMENTS

EP  1 580 598 A  9/2005
EP  1 589 377 A  10/2005

(Continued)

OTHER PUBLICATIONS

D. Gil et al., "First Microprocessors with Immersion Lithograhy," Optical Microlithography XVIII, Proceedings of SPIE vol. 5754, pp. 119-128 (2005).

(Continued)

*Primary Examiner* — Paul A Zucker
(74) *Attorney, Agent, or Firm* — Knobbe Martens Olson & Bear LLP

(57) ABSTRACT

A resist composition for immersion exposure, including a base component (A) that exhibits changed solubility in an alkali developing solution under action of acid, an acid generator component (B) that generates acid upon exposure, and a fluorine-containing compound (C) represented by a general formula (c-1) shown below that is decomposable in an alkali developing solution:

[Chemical Formula 1]

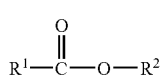

(c-1)

wherein $R^1$ represents an organic group which may contain a polymerizable group, with the proviso that said polymerizable group has a carbon-carbon multiple bond, and the carbon atoms forming the multiple bond are not directly bonded to the carbon atom within the —C(=O)— group in general formula (c-1); and $R^2$ represents an organic group having a fluorine atom.

28 Claims, 1 Drawing Sheet

(56) References Cited

U.S. PATENT DOCUMENTS

| | | |
|---|---|---|
| 2008/0319134 A1 | 12/2008 | Ma et al. |
| 2009/0068590 A1 | 3/2009 | Dazai et al. |
| 2009/0105400 A1 | 4/2009 | Komatsu et al. |
| 2009/0117489 A1 | 5/2009 | Wang et al. |
| 2009/0197204 A1 | 8/2009 | Shiono et al. |
| 2009/0226842 A1 | 9/2009 | Shimizu et al. |
| 2009/0233223 A1 | 9/2009 | Tachibana et al. |
| 2009/0317743 A1 | 12/2009 | Shiono et al. |
| 2010/0035178 A1 | 2/2010 | Abe et al. |
| 2010/0062369 A1 | 3/2010 | Dazai et al. |
| 2010/0069590 A1 | 3/2010 | Utsumi et al. |
| 2010/0075249 A1 | 3/2010 | Utsumi et al. |
| 2010/0081088 A1 | 4/2010 | Kawaue et al. |
| 2010/0136480 A1 | 6/2010 | Motoike et al. |
| 2010/0168358 A1 | 7/2010 | Shimamaki et al. |
| 2010/0196820 A1 | 8/2010 | Kawaue et al. |
| 2010/0209848 A1 | 8/2010 | Dazai et al. |
| 2010/0233623 A1 | 9/2010 | Kurosawa et al. |
| 2010/0233625 A1 | 9/2010 | Hirano et al. |
| 2010/0233626 A1 | 9/2010 | Shimizu et al. |
| 2010/0266957 A1 | 10/2010 | Harada et al. |
| 2010/0310985 A1 | 12/2010 | Mori et al. |
| 2011/0104611 A1 | 5/2011 | Sakakibara et al. |
| 2011/0117497 A1 | 5/2011 | Sato et al. |
| 2011/0117499 A1 | 5/2011 | Matsumiya et al. |
| 2011/0236824 A1 | 9/2011 | Hirano et al. |
| 2012/0094236 A1 | 4/2012 | Shiono et al. |

FOREIGN PATENT DOCUMENTS

| | | | |
|---|---|---|---|
| EP | 2 048 128 A | | 4/2009 |
| JP | 53139693 A | * | 5/1977 |
| JP | 06-0017505 A | * | 1/1994 |
| JP | 06001750 | | 1/1994 |
| JP | A-06-083079 | | 3/1994 |
| JP | A-06-306013 | | 11/1994 |
| JP | H09-208554 | | 8/1997 |
| JP | H10-221852 | | 8/1998 |
| JP | H11-035551 | | 2/1999 |
| JP | H11-035552 | | 2/1999 |
| JP | H11-035573 | | 2/1999 |
| JP | H11-133593 A | | 5/1999 |
| JP | H11-322707 | | 11/1999 |
| JP | 2003-241385 | | 8/2003 |
| JP | 2004-323693 | | 11/2004 |
| JP | A-2005-055890 | | 3/2005 |
| JP | 2005-126459 | | 5/2005 |
| JP | 2005-344009 | | 12/2005 |
| JP | 2006-045311 | | 2/2006 |
| JP | 2006-048029 | | 2/2006 |
| JP | 2006-215526 | | 8/2006 |
| JP | 2006-299278 | | 11/2006 |
| JP | 2006-309245 | | 11/2006 |
| JP | 2006-328259 | | 12/2006 |
| JP | A-2007-093910 | | 4/2007 |
| JP | A-2007-119696 | | 5/2007 |
| JP | 2007-219471 | | 8/2007 |
| JP | A-2007-246600 | | 9/2007 |
| JP | A-2008-007409 | | 1/2008 |
| JP | 2008-033287 | | 2/2008 |
| JP | 2008-058538 | | 3/2008 |
| JP | 2008-096816 | | 4/2008 |
| JP | 2008-116496 | | 5/2008 |
| JP | A-2008-111103 | | 5/2008 |
| JP | A-2008-115203 | | 5/2008 |
| JP | A-2008-521039 | | 6/2008 |
| JP | 2008-158339 | | 7/2008 |
| JP | A-2008-247919 | | 10/2008 |
| JP | A-2009-062491 | | 3/2009 |
| JP | 2009-091350 | | 4/2009 |
| JP | 2009-091351 | | 4/2009 |
| JP | A-2009-098509 | | 5/2009 |
| JP | 2009-199058 | | 9/2009 |
| JP | A-2009-244859 | | 10/2009 |
| JP | 2010-018777 | | 1/2010 |
| JP | A-2010-002839 | | 1/2010 |
| JP | A-2010-134417 | | 6/2010 |
| JP | A-2010-139996 | | 6/2010 |
| JP | A-2010-204187 | | 9/2010 |
| JP | A-2010-230891 | | 10/2010 |
| JP | A-2010-250105 | | 11/2010 |
| KR | 10-2007-0074476 A | | 7/2007 |
| TW | 200741347 | | 11/2007 |
| TW | 200801049 | | 1/2008 |
| WO | WO 92/00366 A1 | * | 1/1992 |
| WO | WO 2004-074242 | | 9/2004 |
| WO | WO 2006/054173 A1 | | 5/2006 |
| WO | WO 2007/091517 A1 | | 8/2007 |
| WO | WO 2008/021291 | | 2/2008 |
| WO | WO 2008/053697 | | 5/2008 |
| WO | WO 2008/123560 A | | 10/2008 |
| WO | WO 2009/142183 A1 | | 11/2009 |
| WO | WO 2010/001913 A1 | | 1/2010 |

OTHER PUBLICATIONS

Shun-Ichi Kodama et al., "Synthesis of Novel Fluoropolymer for 157nm Photoresists by Cyclo-polymerization." Advances in Resist Technology and Processing XIX, Proceedings of SPIE vol. 4690, pp. 76-83, (2002).

Decision for Grant of Patent received in corresponding Korean Patent Application No. 10-2009-0007960 dated Jun. 28, 2011.

The European Search Report issued in corresponding European Patent Application No. EP 09152046, dated May 20, 2009. The letter acknowledging receipt (on Jun. 2, 2009) of the Search Report by the Foreign Associate is included.

Office Action issued in U.S. Appl. No. 13/336,131 on Oct. 16, 2012.

Office Action issued in U.S. Appl. No. 12/457,424 on Jun. 17, 2011.

Notice of Allowance issued in U.S. Appl. No. 12/457,424 on Nov. 30, 2011.

Office Action issued in U.S. Appl. No. 13/218,797 on Apr. 17, 2012.

Irie et al., "Surface Property Control for 193nm Immersion Resist," Journal of Photopolymer Science and Technology, vol. 19, No. 4, pp. 565-568, 2006.

Office Action issued in U.S. Appl. No. 12/457,705 on Sep. 27, 2011.

Office Action issued in U.S. Appl. No. 12/979,067 on Aug. 3, 2012.

Office Action issued in U.S. Appl. No. 12/824,089 on Apr. 6, 2012.

Office Action issued in U.S. Appl. No. 13/310,625 on Jul. 24, 2012.

Office Action issued in U.S. Appl. No. 12/824,089 on Jul. 25, 2012.

Office Action issued in Japanese Patent Application No. 2008-163861 on Jun. 26, 2012.

Office Action issued in Taiwanese Patent Application No. 098103527 on Jul. 23, 2012.

Office Action issued on Jan. 6, 2012 for U.S. Appl. No. 12/721,291.

Office Action issued on Mar. 15, 2012 for U.S. Appl. No. 12/717,785.

Office Action issued on Mar. 4, 2013 for U.S. Appl. No. 12/979,067.

Office Action issued on Feb. 26, 2013 for Japanese Patent Application No. 2009-052179.

Office Action issued on Mar. 12, 2013 for Japanese Patent Application No. 2008-317487.

Office Action issued on Mar. 12, 2013 for Japanese Patent Application No. 2009-055745.

Notice of Allowance issued on May 1, 2013 for U.S. Appl. No. 13/218,797.

Office Action issued on Aug. 1, 2013 in U.S. Appl. No. 13/661,518.

Office Action issued on Aug. 6, 2013 in Japanese Patent Application No. 2009-159073.

Office Action issued on Sep. 26, 2013 in U.S. Appl. No. 12/979,067.

Notice of Allowance issued on Jul. 23, 2013 in Japanese Patent Application No. 2009-057167.

Notice of Allowance issued on Jan. 7, 2014 in Japanese Patent Application No. 2010-000662.

* cited by examiner

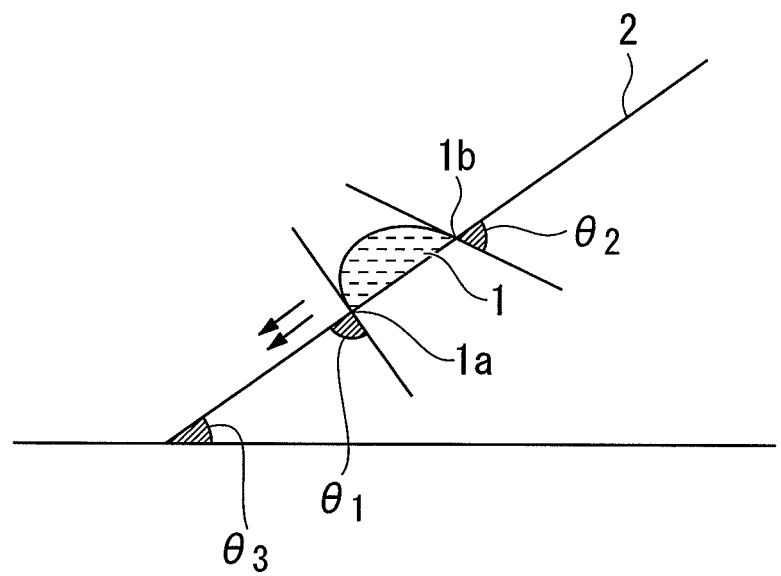

RESIST COMPOSITION FOR IMMERSION EXPOSURE, METHOD OF FORMING RESIST PATTERN USING THE SAME, AND FLUORINE-CONTAINING COMPOUND

TECHNICAL FIELD

The present invention relates to a resist composition for immersion exposure (liquid immersion lithography) including a fluorine-containing compound, a method of forming a resist pattern using the resist composition for immersion exposure, and a fluorine-containing compound.

Priority is claimed on Japanese Patent Application No. 2008-027045, filed Feb. 6, 2008, Japanese Patent Application No. 2008-099826, filed Apr. 7, 2008, Japanese Patent Application No. 2008-163862, filed Jun. 23, 2008, and Japanese Patent Application No. 2008-317487, filed Dec. 12, 2008, the contents of which are incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

For miniaturization of semiconductor devices, shortening of the wavelength of the exposure light source, and increasing of the numerical aperture (NA) of the projector lens have progressed. Currently, exposure apparatuses in which an ArF excimer laser having a wavelength of 193 nm is used as an exposure light source and NA=0.84 have been developed. As shortening the wavelength of the exposure light source progresses, it is required to improve various lithography properties of the resist material, such as the sensitivity to the exposure light source and a resolution capable of reproducing patterns of minute dimensions. As a resist material which satisfies these conditions, a chemically amplified resist is used, which includes a base resin that exhibits a changed solubility in an alkali developing solution under action of acid and an acid generator that generates acid upon exposure.

Currently, resins that contain structural units derived from (meth)acrylate esters within the main chain (acrylic resins) are now widely used as base resins for resists that use ArF excimer laser lithography, as they exhibit excellent transparency in the vicinity of 193 nm.

Here, the term "(meth)acrylic acid" is a generic term that includes either or both of acrylic acid having a hydrogen atom bonded to the α-position and methacrylic acid having a methyl group bonded to the α-position.

The term "(meth)acrylate ester" is a generic term that includes either or both of the acrylate ester having a hydrogen atom bonded to the α-position and the methacrylate ester having a methyl group bonded to the α-position.

The term "(meth)acrylate" is a generic term that includes either or both of the acrylate having a hydrogen atom bonded to the α-position and the methacrylate having a methyl group bonded to the α-position.

As a technique for further improving the resolution, a lithography method called liquid immersion lithography (hereafter, frequently referred to as "immersion exposure") is known in which exposure (immersion exposure) is conducted in a state where the region between the lens and the resist layer formed on a wafer is filled with a solvent (a immersion medium) that has a larger refractive index than the refractive index of air (see for example, Non-Patent Document 1).

According to this type of immersion exposure, it is considered that higher resolutions equivalent to those obtained using a shorter wavelength light source or a larger NA lens can be obtained using the same exposure light source wavelength, with no lowering of the depth of focus. Furthermore, immersion exposure can be conducted using a conventional exposure apparatus. As a result, it is expected that immersion exposure will enable the formation of resist patterns of higher resolution and superior depth of focus at lower costs. Accordingly, in the production of semiconductor devices, which requires enormous capital investment, immersion exposure is attracting considerable attention as a method that offers significant potential to the semiconductor industry, both in terms of cost and in terms of lithography properties such as resolution.

Immersion lithography is effective in forming patterns having various shapes. Further, immersion exposure is expected to be capable of being used in combination with currently studied super-resolution techniques, such as phase shift method and modified illumination method. Currently, as the immersion exposure technique, technique using an ArF excimer laser as an exposure source is being actively studied, and water is mainly used as the immersion medium.

In recent years, fluorine-containing compounds have been attracting attention for their properties such as water repellency and transparency, and active research and development of fluorine-containing compounds have been conducted in various fields. For example, in the fields of resist materials, currently, an acid-labile group such as a methoxyethyl group, tert-butyl group or tert-butoxycarbonyl group is being introduced into a fluorine-containing polymeric compound, and the fluorine-containing polymeric compound is used as a base resin for a chemically amplified positive resist. However, when such a fluorine-containing polymeric compound is used as a base resin for a chemically amplified positive resist, disadvantages are caused in that a large amount of an out gas is generated, and resistance to a dry-etching gas (etching resistance) is unsatisfactory.

Recently, as a fluorine-containing polymeric compound exhibiting excellent etching resistance, a fluorine-containing polymeric compound having an acid-labile group containing a cyclic hydrocarbon group has been reported (see, for example, Non-Patent Document 2).

[Non-Patent Document 1] Proceedings of SPIE (U.S.), vol. 5754, pp. 119-128 (2005)

[Non-Patent Document 2] Proceedings of SPIE (U.S.), vol. 4690, pp. 76-83 (2002)

SUMMARY OF THE INVENTION

In immersion exposure, it is required to use a resist material which exhibits not only general lithography properties (e.g., sensitivity, resolution, etching resistance and the like), but also properties suited for immersion lithography. For example, in immersion exposure, when the resist film comes in contact with the immersion medium, elution of a substance contained in the resist film into the immersion medium occurs. This elution of a substance causes phenomenons such as degeneration of the resist film and change in the refractive index of the immersion medium, thereby adversely affecting the lithography properties. The amount of the eluted substance is affected by the properties of the resist film surface (e.g., hydrophilicity, hydrophobicity, and the like). For example, by enhancing the hydrophobicity of the resist film surface, the elution of a substance can be reduced. Further, when the immersion medium is water, and immersion exposure is performed using a scanning-type immersion exposure apparatus as disclosed in Non-Patent Document 1, tracking ability of water with respect to the movement of the lens (hereafter, frequently referred to as "water tracking ability") is required. When the water tracking ability is low, the exposure speed becomes low, and as a result, there is a possibility that the productivity is adversely affected. It is presumed that the water tracking ability can be improved by enhancing the hydrophobicity of the resist film (rendering the resist film hydrophobic).

Thus, it is presumed that the above-described characteristic problems of immersion lithography such as reducing elution of a substance and improving the water tracking ability can be solved by enhancing the hydrophobicity of the resist film surface. However, when the resist film is simply rendered hydrophobic, lithography properties are adversely affected. For example, when the hydrophobicity of a resist film is enhanced, a problem occurs in that defects are likely to be generated in the resist film following alkali developing. Especially, in a positive resist composition, defects are likely to be generated at unexposed portions.

Here, defects refers to general abnormalities of a resist pattern, which are detected when observed from right above the developed resist pattern, using a surface defect detection equipment (trade name: "KLA") manufactured by KLA-TENCOR CORPORATION. Examples of these abnormalities include post-developing scum, foam, dust, bridges across different portions of the resist pattern, color irregularities, and foreign deposits.

It is presumed that the above-mentioned problems can be solved by a material which is hydrophobic during immersion exposure, and becomes hydrophilic during developing. However, at present, a material exhibiting such properties is essentially unknown.

The present invention takes the above circumstances into consideration, with an object of providing a resist composition preferable for use in immersion exposure, a method of forming a resist pattern using the resist composition, and a fluorine-containing compound useful as an additive for the resist composition.

For solving the above-mentioned problems, the present invention employs the following aspects.

Specifically, a first aspect of the present invention is a resist composition for immersion exposure, including a base component (A) that exhibits changed solubility in an alkali developing solution under action of acid, an acid generator component (B) that generates acid upon exposure, and a fluorine-containing compound (C) represented by a general formula (c-1) shown below that is decomposable in an alkali developing solution.

[Chemical Formula 1.]

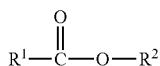

(c-1)

wherein $R^1$ represents an organic group which may have a polymerizable group, with the proviso that said polymerizable group has a carbon-carbon multiple bond, and the carbon atoms forming the multiple bond are not directly bonded to the carbon atom within the —C(=O)— group in general formula (c-1); and $R^2$ represents an organic group having a fluorine atom.

A second aspect of the present invention is a method of forming a resist pattern, including forming a resist film using a resist composition for immersion exposure according to the first aspect, subjecting the resist film to immersion exposure, and subjecting the resist film to alkali developing to form a resist pattern.

A third aspect of the present invention is a fluorine-containing compound represented by general formula (c-1) shown below.

[Chemical Formula 2.]

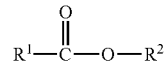

(c-1)

wherein $R^1$ represents an organic group which may contain a polymerizable group, with the proviso that said polymerizable group has a carbon-carbon multiple bond, and the carbon atoms forming the multiple bond are not directly bonded to the carbon atom with the —C(=O)— group in general formula (c-1); and $R^2$ represents an organic group having a fluorine atom.

In the present description and claims, an "alkyl group" includes linear, branched or cyclic, monovalent saturated hydrocarbon, unless otherwise specified.

The term "alkylene group" includes linear, branched or cyclic divalent saturated hydrocarbon, unless otherwise specified.

A "lower alkyl group" is an alkyl group of 1 to 5 carbon atoms.

A "halogenated alkyl group" is a group in which a part or all of the hydrogen atoms of an alkyl group is substituted with halogen atoms. Examples of halogen atoms include fluorine atoms, chlorine atoms, bromine atoms and iodine atoms.

The term "aliphatic" is a relative concept used in relation to the term "aromatic", and defines a group or compound that has no aromaticity.

The term "structural unit" refers to a monomer unit that contributes to the formation of a polymeric compound (polymer, copolymer).

The term "exposure" is used as a general concept that includes irradiation with any form of radiation.

According to the present invention, there are provided a resist composition preferable for use in immersion exposure, a method of forming a resist pattern using the resist composition, and a fluorine-containing compound useful as an additive for the resist composition.

BRIEF DESCRIPTION OF THE DRAWINGS

FIG. 1 is an explanatory diagram of advancing angle ($\theta_1$), receding angle ($\theta_2$) and sliding angle ($\theta_3$).

DESCRIPTION OF REFERENCE NUMERALS AND CHARACTERS

1 Droplet
1a Lower end
1b Upper end
2 Plane
($\theta_1$) Advancing angle
($\theta_2$) Receding angle
($\theta_3$) Sliding angle

DETAILED DESCRIPTION OF THE INVENTION

<<Resist Composition for Immersion Exposure>>

The resist composition for immersion exposure according to the present invention includes a base component (A) which exhibits changed solubility in an alkali developing solution under action of acid (hereafter, referred to as "component (A)"), an acid-generator component (B) which generates acid upon exposure (hereafter, referred to as "component (B)"), and a fluorine-containing compound (C) represented by a general formula (c-1) above that is decomposable in an alkali developing solution (hereafter, referred to as "component (C)").

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more used as base components are broadly classified into low molecular weight organic compounds having a molecular weight of 500 to less than 2,000 (hereafter, frequently referred to as "low molecular weight materials") and high molecular weight organic compounds (polymeric materials) having a molecular weight of 2,000 or more. Generally, as the aforementioned low molecular weight material, a non-polymer is used. As a polymeric material, a resin (polymer or copolymer) is used, and the molecular weight of the resin is the polystyrene equivalent value determined by gel permeation chromatography (GPC). Hereafter, a "resin" refers to a resin having a molecular weight of 2,000 or more.

As the component (A), a resin which exhibits changed solubility in an alkali developing solution under action of acid may be used. Alternatively, as the component (A), a low molecular weight material which exhibits changed solubility in an alkali developing solution under action of acid may be used.

When the resist composition for immersion exposure according to the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, as it enables formation of a satisfactory resist pattern with minimal swelling. Here, the term "α-(hydroxyalkyl) acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linking agent added is preferably within the range from 1 to 50 parts by weight, relative to 100 parts by weight of the alkali-soluble resin.

When the resist composition of the present invention is a positive resist composition, as the component (A), a base component which exhibits increased solubility in an alkali developing solution by action of acid is used. The component (A) is insoluble in an alkali developing solution prior to exposure, and when acid is generated from the component (B) upon exposure, the solubility thereof in an alkali developing solution increases. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component which exhibits increased solubility in an alkali developing solution under action of acid. That is, the resist composition of the present invention is preferably a positive resist composition.

The component (A) may be a resin component (A1) which exhibits increased solubility in an alkali developing solution under action of acid (hereafter, referred to as "component (A1)"), a low molecular weight material (A2) which exhibits increased solubility in an alkali developing solution under action of acid (hereafter, referred to as "component (A2)"), or a mixture of the component (A1) and the component (A2).

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, ethyl group, propyl group, isopropyl group, n-butyl group, isobutyl group, tert-butyl group, pentyl group, isopentyl group, and neopentyl group.

Specific examples of the halogenated lower alkyl group include groups in which some or all of the hydrogen atoms of the aforementioned "lower alkyl group for the substituent at the α-position" are substituted with halogen atoms. Examples of halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

It is particularly desirable that the component (A1) have a structural unit (a1) derived from an acrylate ester containing an acid dissociable, dissolution inhibiting group.

Further, it is preferable that the component (A1) have a structural unit (a2) derived from an acrylate ester containing a lactone-containing cyclic group, as well as the structural unit (a1).

Furthermore, it is preferable that the component (A1) have a structural unit (a3) derived from an acrylate ester containing a polar group-containing aliphatic hydrocarbon group, as well as the structural unit (a1), or the structural unit (a1) and the structural unit (a2).

Structural Unit (a1):

As the acid-dissociable, dissolution-inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution.

Generally, groups that form either a cyclic or chain-like tertiary alkyl ester with the carboxyl group of the (meth) acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclodecanyl group, and a branched alkylene group having a tertiary carbon atom bonded thereto, as the groups bonded to the oxygen atom of the carbonyl group (—C(O)—O—) within the structural units represented by general formulas (a1"-1) to (a1"-6) shown below, can be used.

[Chemical Formula 3.]

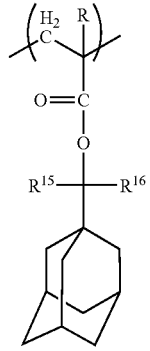

(a1"-1)

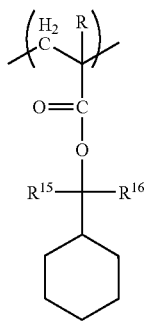

(a1″-2)

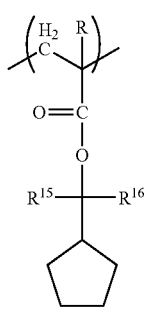

(a1″-3)

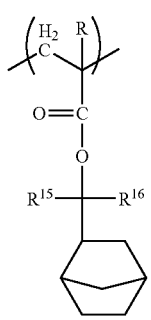

(a1″-4)

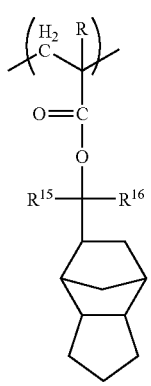

(a1″-5)

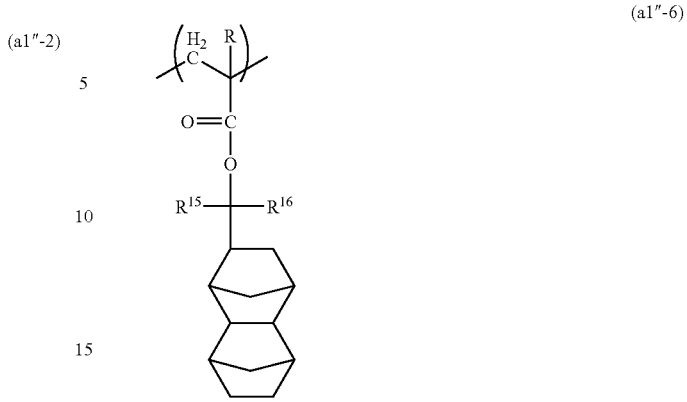

(a1″-6)

wherein R represents a hydrogen atom, a lower alkyl group or a halogenated lower alkyl group; and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 4.]

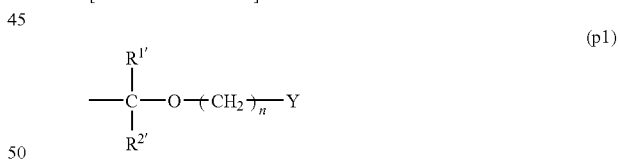

(p1)

wherein $R^{1\prime}$ and $R^{2\prime}$ each independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same lower alkyl groups as those for R above can be used. As the lower alkyl group for $R^{1\prime}$ and $R^{2\prime}$, a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

[Chemical Formula 5.]

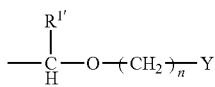

(p1-1)

wherein $R^{1'}$, n and Y are as defined above.

As the lower alkyl group for Y, the same lower alkyl groups as those for R above can be used.

As the aliphatic cyclic group for Y, any of the aliphatic monocyclic/polycyclic groups which have been proposed for conventional ArF resists and the like can be appropriately selected for use. For example, the same groups as those described above in connection with the "aliphatic cyclic group" can be used.

Further, as the acetal-type, acid dissociable, dissolution inhibiting group, groups represented by general formula (p2) shown below can also be shown.

[Chemical Formula 6.]

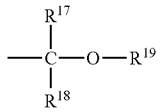

(p2)

wherein $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. Examples of cycloalkyl groups include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 7.]

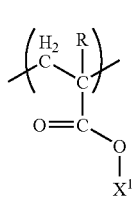

(a1-0-1)

wherein R represents a hydrogen atom, a lower alkyl group or a halogenated lower alkyl group; and $X^1$ represents an acid dissociable, dissolution inhibiting group.

[Chemical Formula 8.]

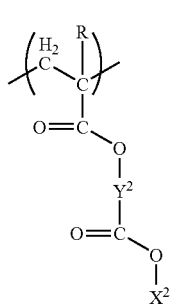

(a1-0-2)

wherein R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined above.

$X^2$ is the same as $X^1$ in general formula (a1-0-1).

$Y^2$ is preferably an alkylene group of 1 to 10 carbon atoms or a divalent aliphatic cyclic group. As the aliphatic cyclic group, the same groups as those described above in connection with the explanation of "aliphatic cyclic group" can be used, except that two hydrogen atoms have been removed therefrom.

When $Y^2$ represents an alkylene group of 1 to 10 carbon atoms, it is more preferable that the number of carbons is 1 to 6, still more preferably 1 to 4, and most preferably 1 to 3.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

Specific examples of the structural unit (a1) include structural units represented by general formulas (a1-1) to (a1-4) shown below.

[Chemical Formula 9.]

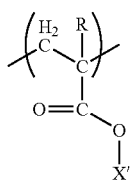
(a1-1)

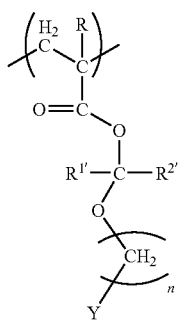
(a1-2)

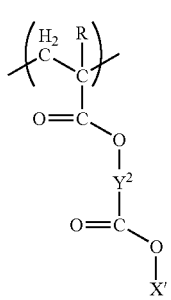
(a1-3)

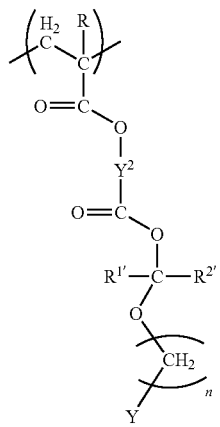
(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group or an aliphatic cyclic group; R is as defined above; and $R^{1'}$ and $R^{2'}$ each independently represents a hydrogen atom or a lower alkyl group of 1 to 5 carbon atoms.

Examples of the tertiary alkyl ester-type acid dissociable, dissolution inhibiting group for X' are the same as the above-mentioned tertiary alkyl ester-type acid dissociable, dissolution inhibiting groups for $X^1$.

As $R^{1'}$, $R^{2'}$, n and Y, the same groups as those for $R^{1'}$, $R^{2'}$, n and Y defined in general formula (p1) described above in connection with the "acetal-type acid dissociable, dissolution inhibiting group" may be used.

As $Y^2$, the same groups as those for $Y^2$ defined in general formula (a1-0-2) above may be used.

Specific examples of structural units represented by general formula (a1-1) to (a1-4) are shown below.

[Chemical Formula 10.]

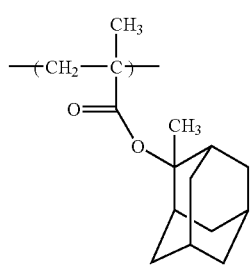
(a1-1-1)

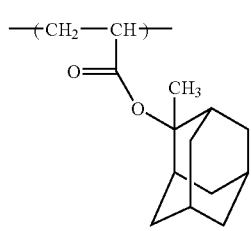
(a1-1-2)

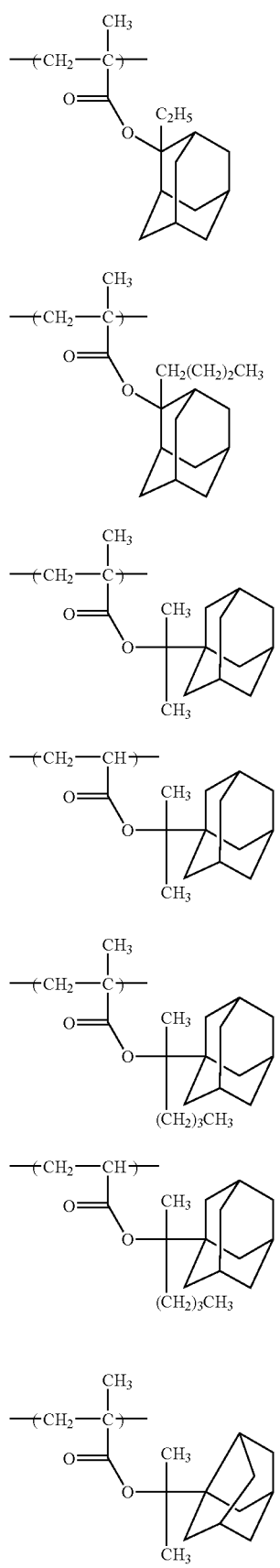
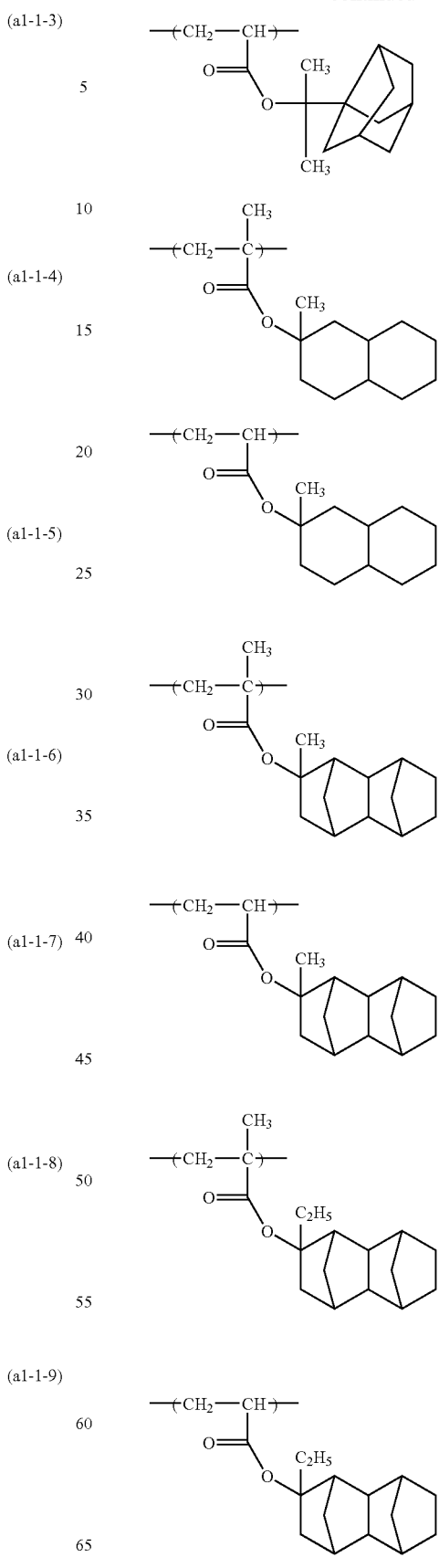

[Chemical Formula 11.]
(a1-1-17) 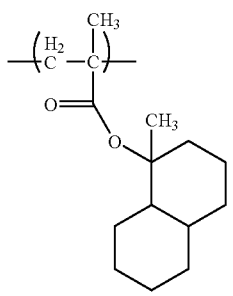
(a1-1-18) 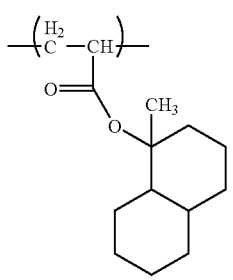
(a1-1-19) 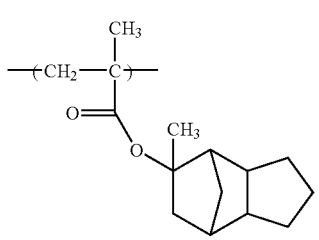
(a1-1-20) 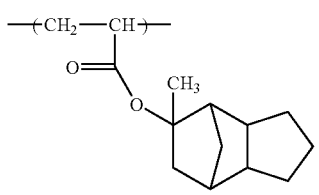
(a1-1-21) 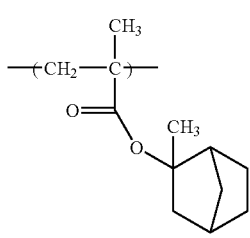
(a1-1-22) 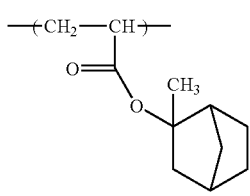
(a1-1-23) 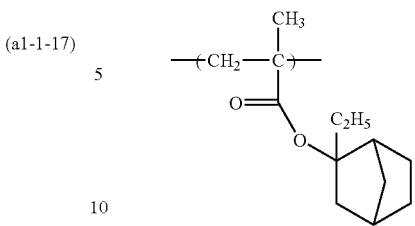
(a1-1-24) 
(a1-1-25) 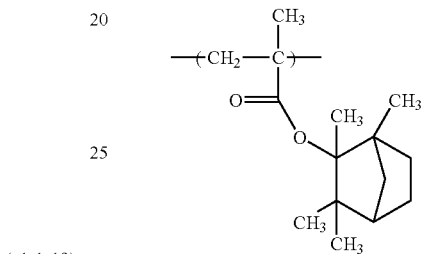
(a1-1-26) 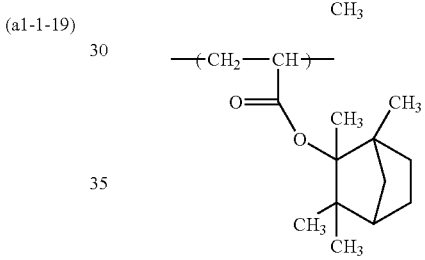
(a1-1-27) 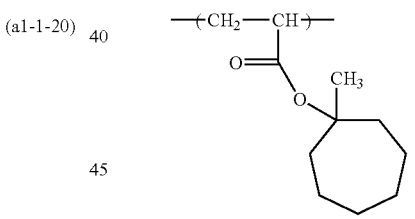
(a1-1-28) 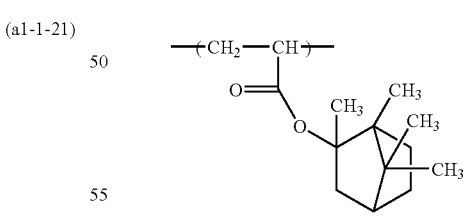
(a1-1-29) 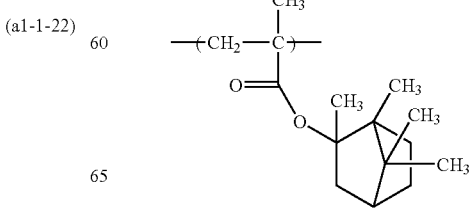

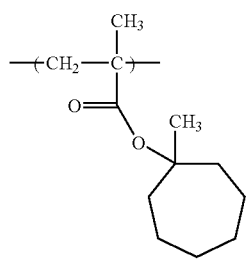
(a1-1-30)
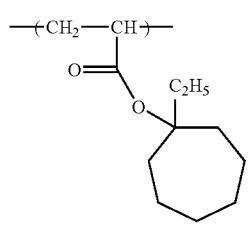
(a1-1-31)
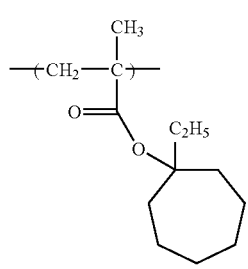
(a1-1-32)
[Chemical Formula 12.]
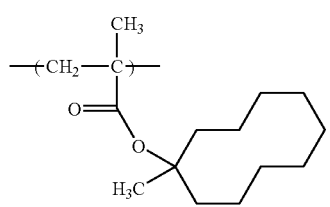
(a1-1-33)
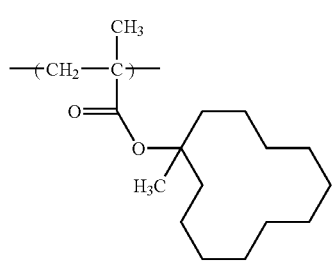
(a1-1-34)
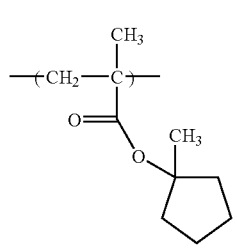
(a1-1-35)
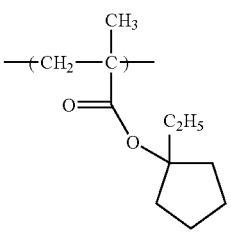
(a1-1-36)
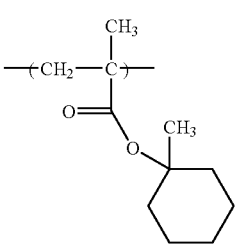
(a1-1-37)
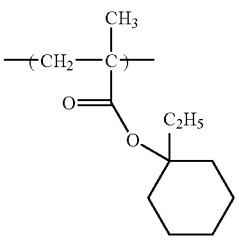
(a1-1-38)
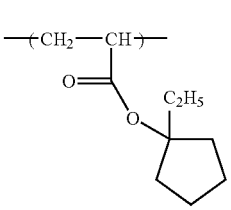
(a1-1-39)
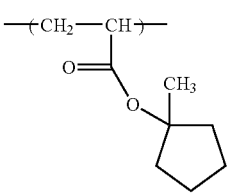
(a1-1-40)
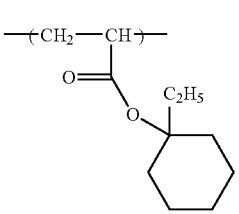
(a1-1-41)
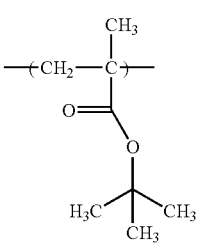
(a1-1-42)

(a1-1-43) 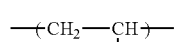
(a1-1-44) 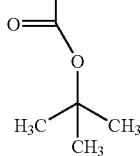
(a1-1-45) 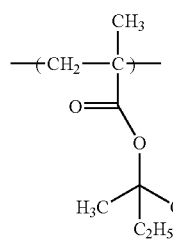
[Chemical Formula 13.]
(a1-2-1) 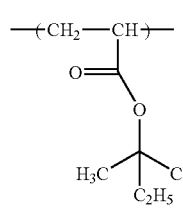
(a1-2-2) 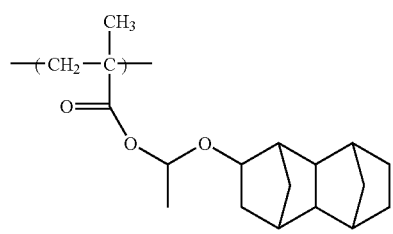
(a1-2-3) 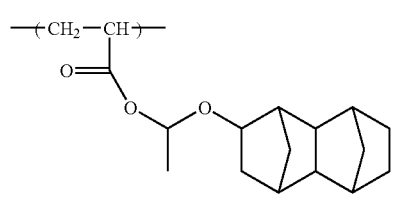
(a1-2-4) 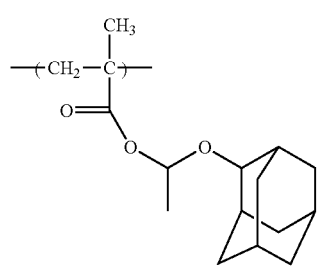
(a1-2-5) 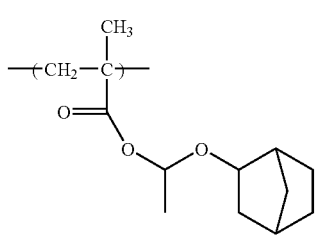
(a1-2-6) 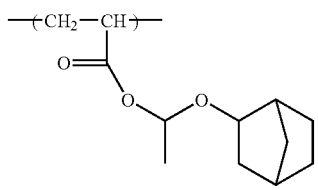
[Chemical Formula 14.]
(a1-2-7) 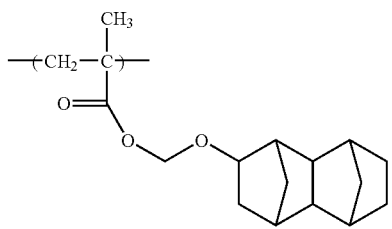
(a1-2-8) 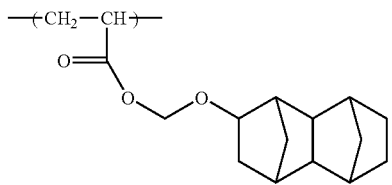
(a1-2-9) 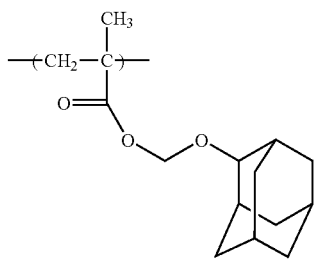
(a1-2-10) 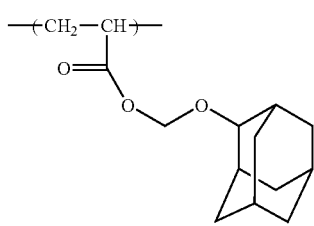
(a1-2-11) 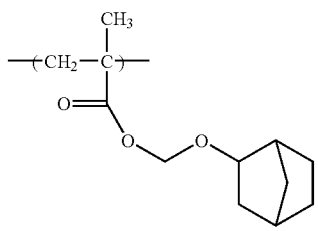

(a1-2-12)
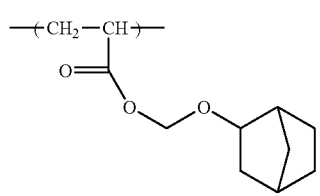
(a1-2-13)
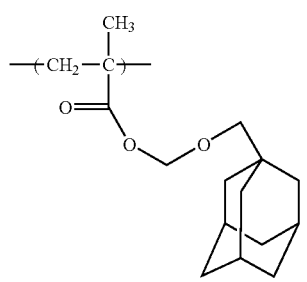
(a1-2-14)
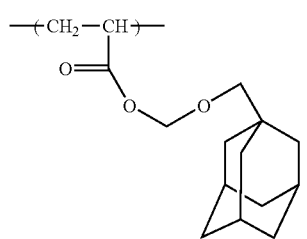
(a1-2-15)
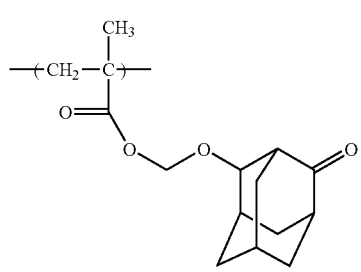
(a1-2-16)
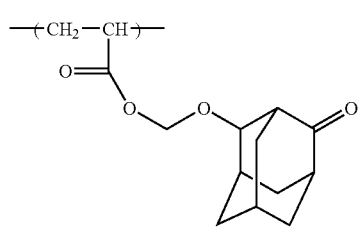
(a1-2-17)
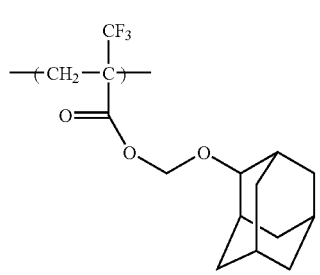
(a1-2-18)
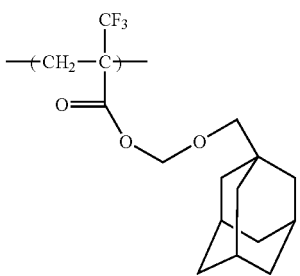
(a1-2-19)
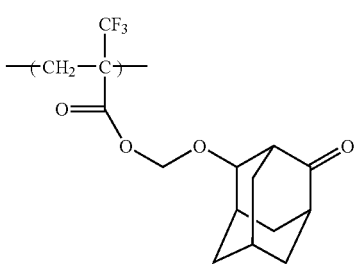
(a1-2-20)
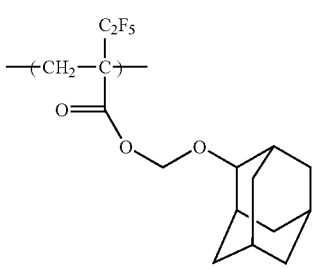
[Chemical Formula 15.]
(a1-2-21)
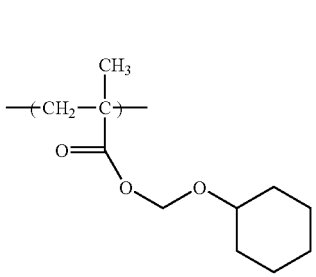
(a1-2-22)
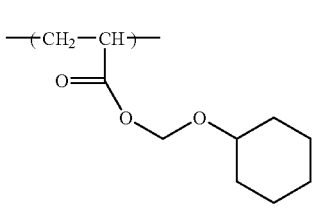
(a1-2-23)
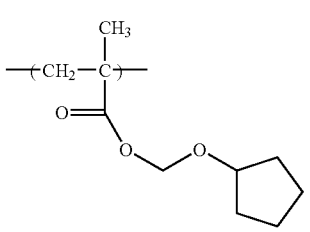

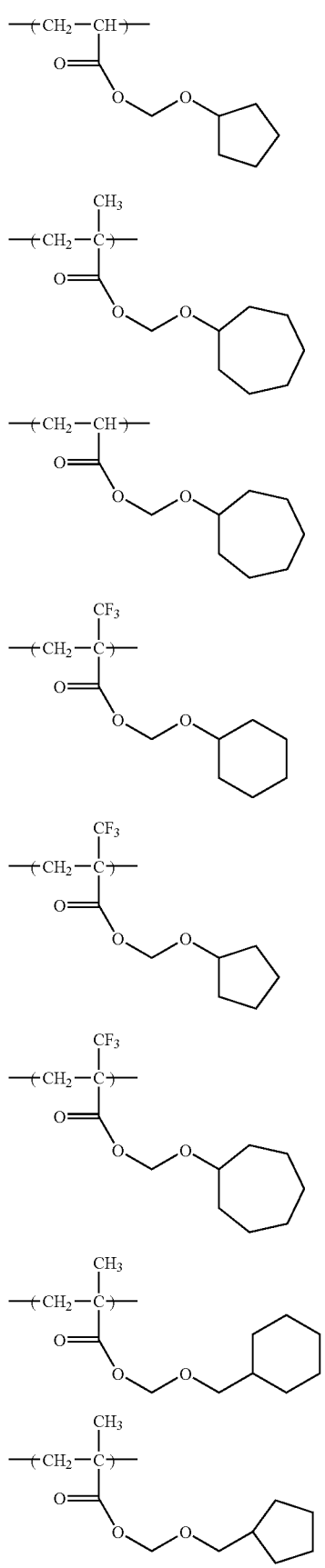
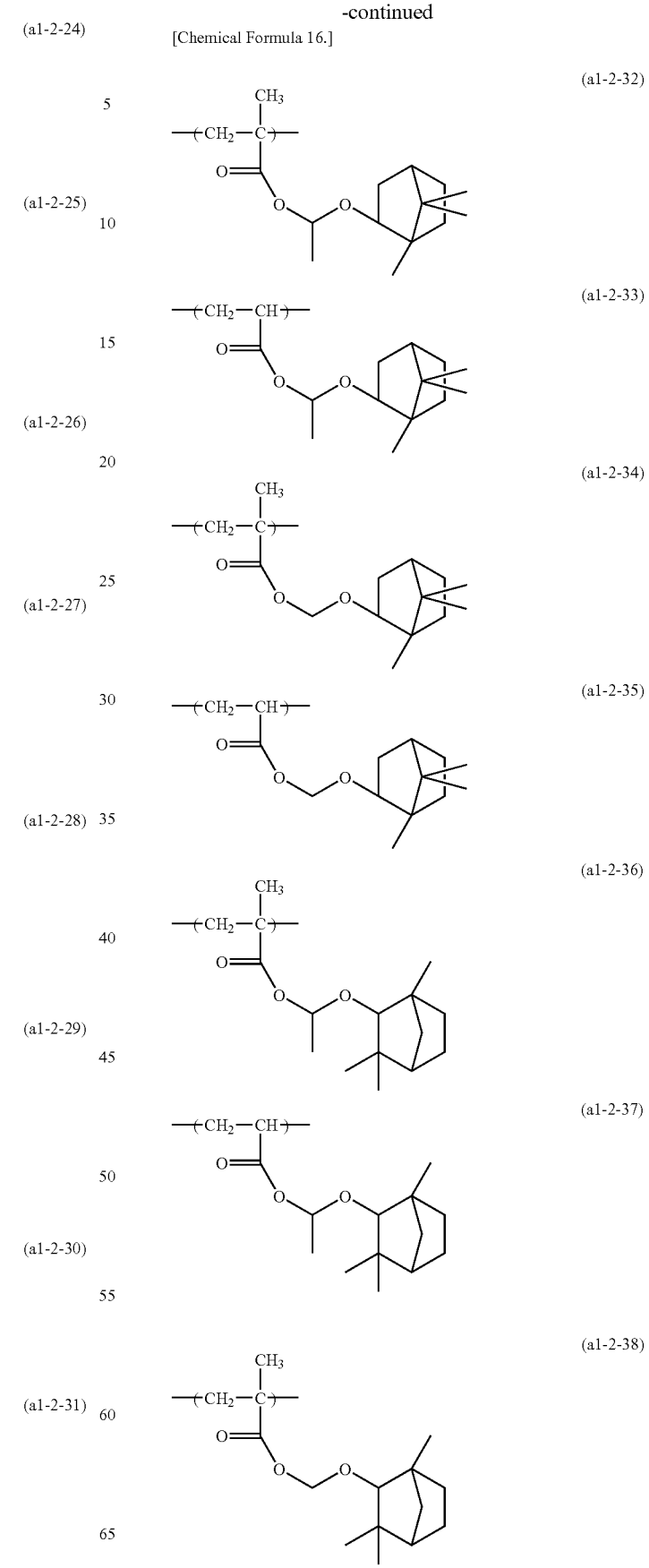

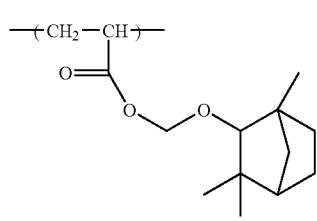
(a1-2-39)
[Chemical Formula 17.]
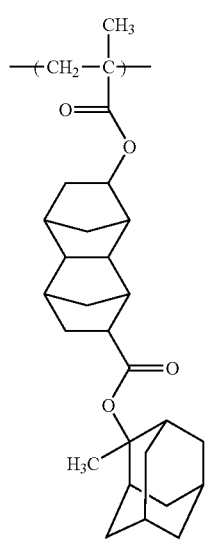
(a1-3-1)
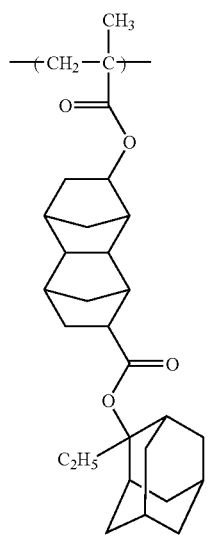
(a1-3-2)
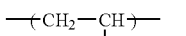
(a1-3-3)
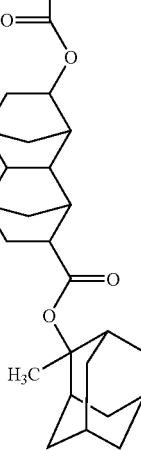
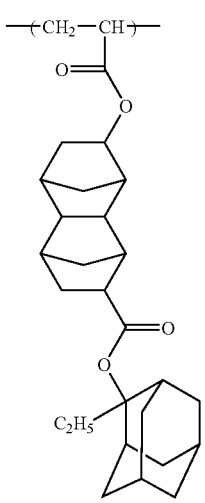
(a1-3-4)
(a1-3-5)

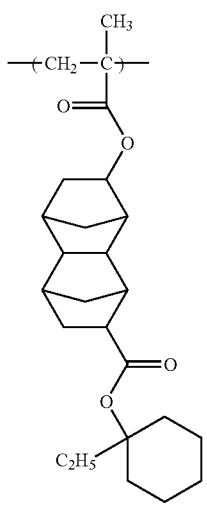
(a1-3-6)
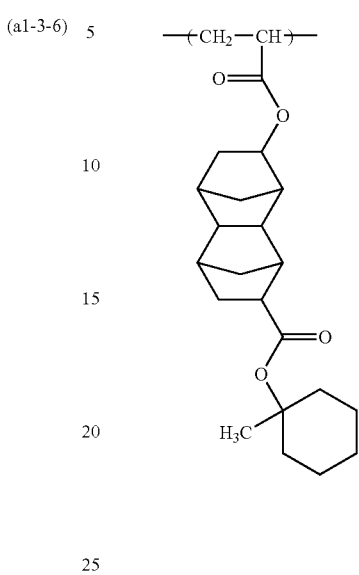
(a1-3-9)
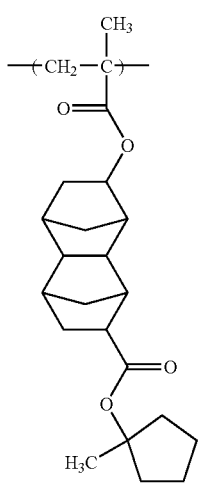
(a1-3-7)
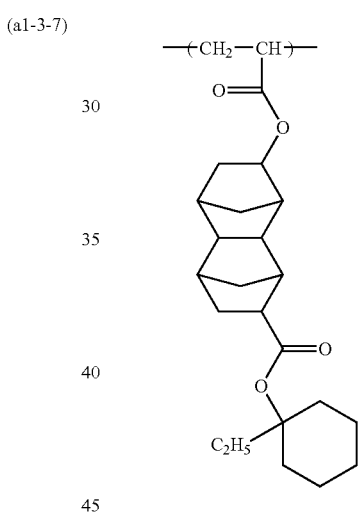
(a1-3-10)
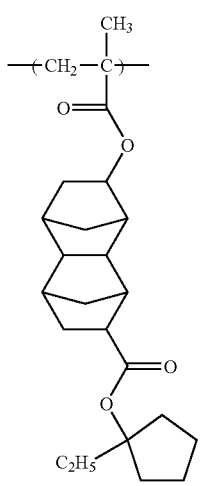
(a1-3-8)
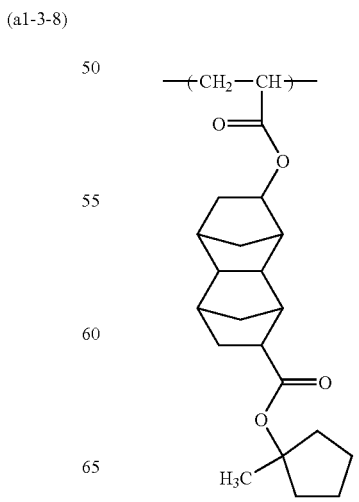
(a1-3-11)

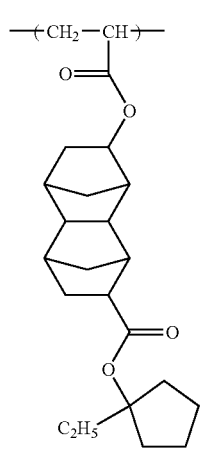 (a1-3-12)
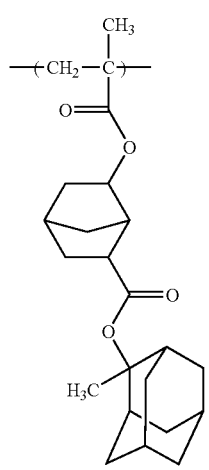 (a1-3-13)
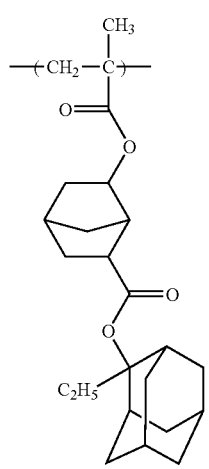 (a1-3-14)
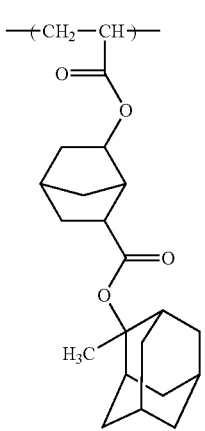 (a1-3-15)
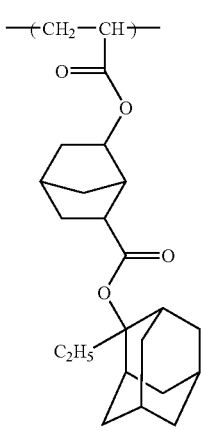 (a1-3-16)
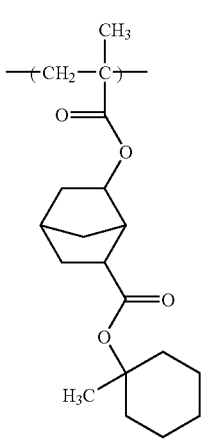 (a1-3-17)

(a1-3-18) 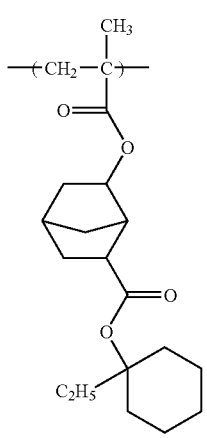
[Chemical Formula 18.]
(a1-3-19) 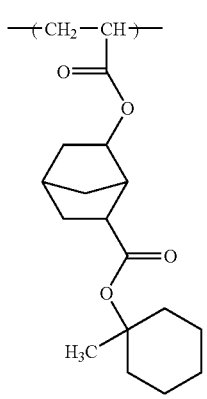
(a1-3-20) 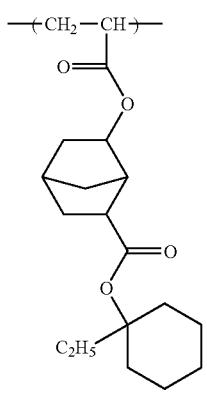
(a1-3-21) 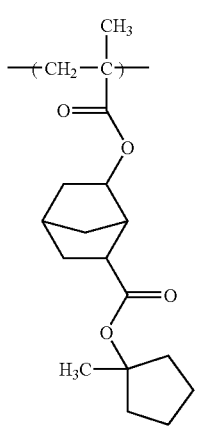
(a1-3-22) 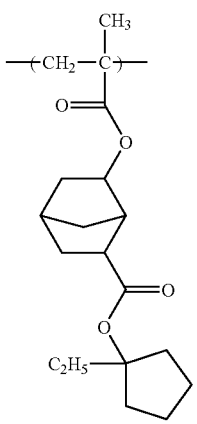
(a1-3-23) 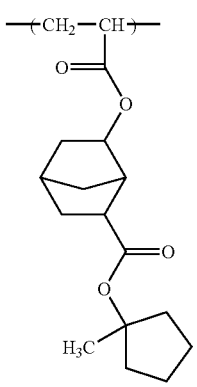
(a1-3-24) 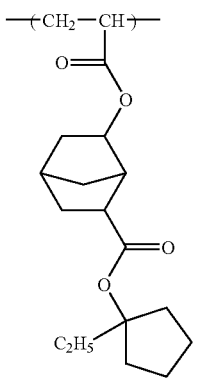
[Chemical Formula 19.]
(a1-3-25) 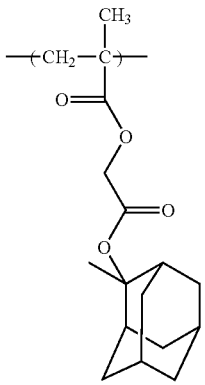

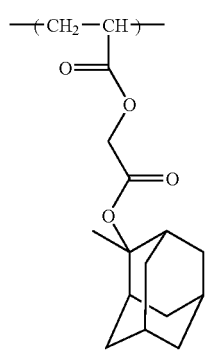 (a1-3-26)
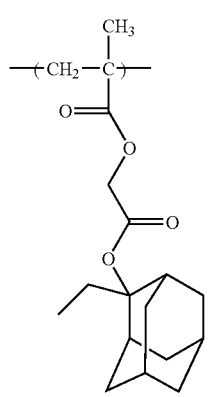 (a1-3-27)
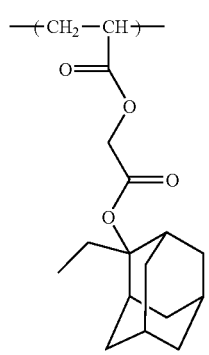 (a1-3-28)
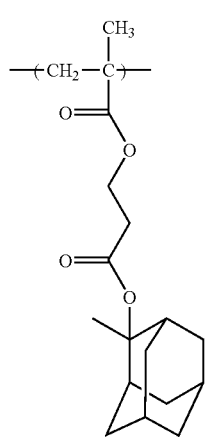 (a1-3-29)
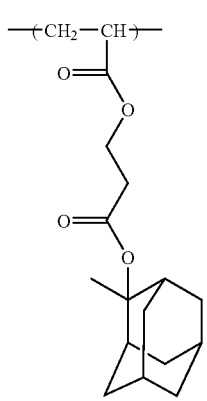 (a1-3-30)
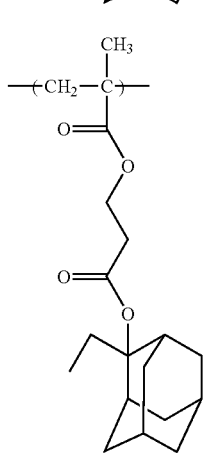 (a1-3-31)
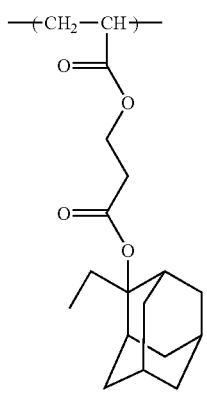 (a1-3-32)
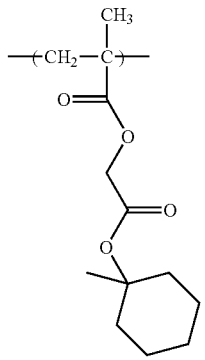 (a1-3-33)

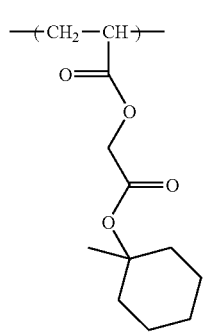 (a1-3-34)
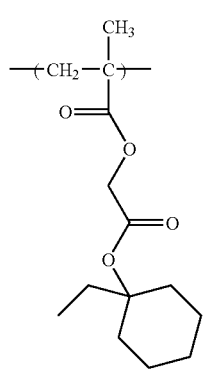 (a1-3-35)
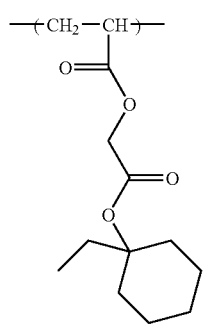 (a1-3-36)
[Chemical Formula 20.]
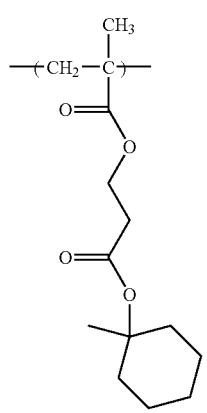 (a1-3-37)
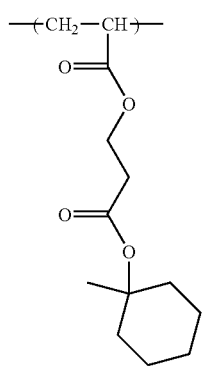 (a1-3-38)
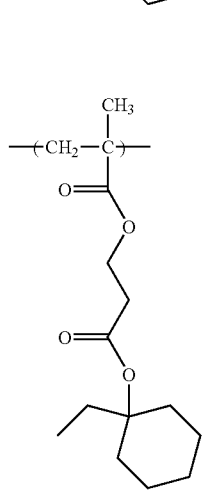 (a1-3-39)
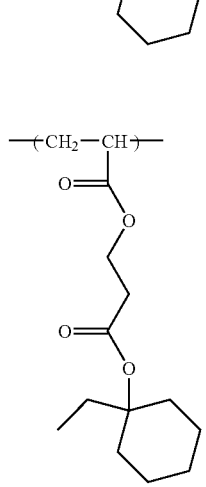 (a1-3-40)
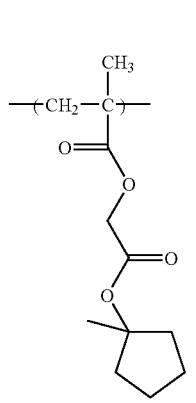 (a1-3-41)

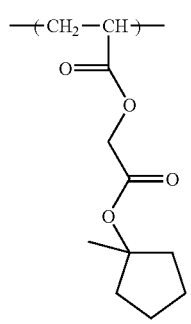 (a1-3-42)
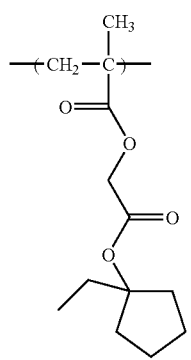 (a1-3-43)
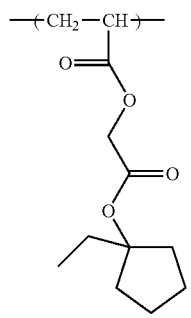 (a1-3-44)
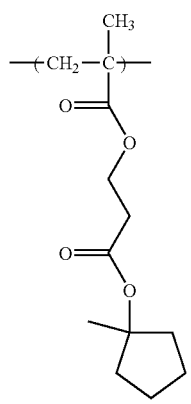 (a1-3-45)
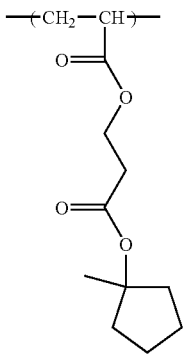 (a1-3-46)
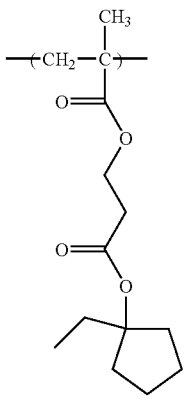 (a1-3-47)
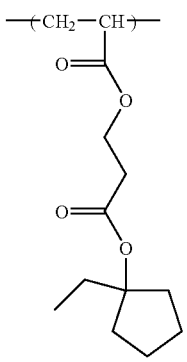 (a1-3-48)
[Chemical Formula 21.]
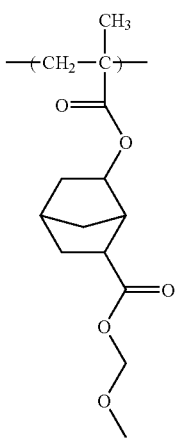 (a1-4-1)

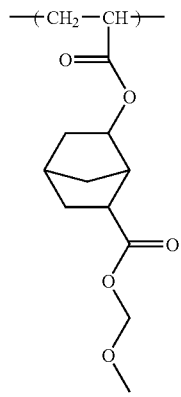
(a1-4-2)
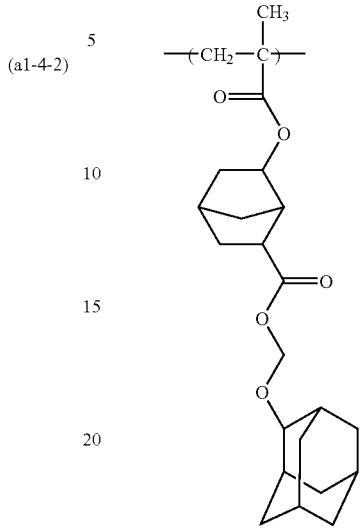
(a1-4-5)
(a1-4-3)
(a1-4-6)
(a1-4-4)
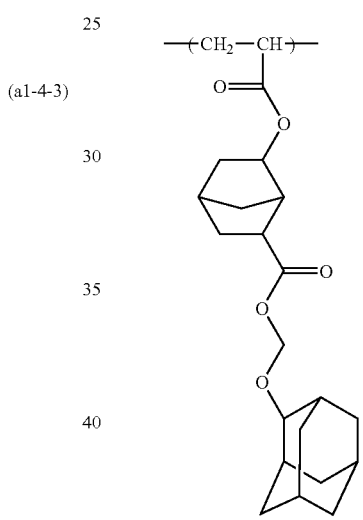
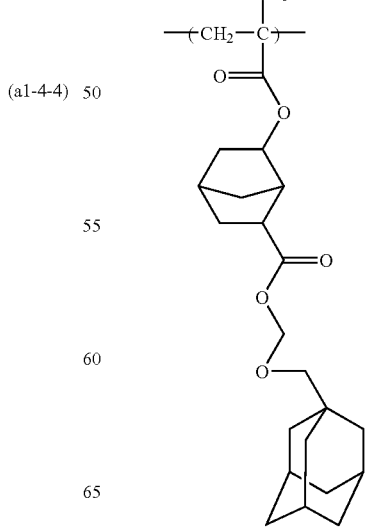
(a1-4-7)

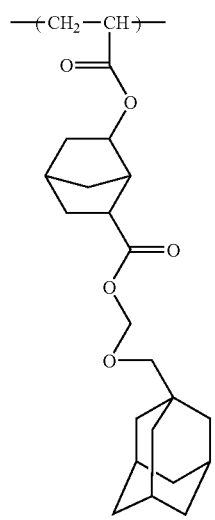
(a1-4-8)
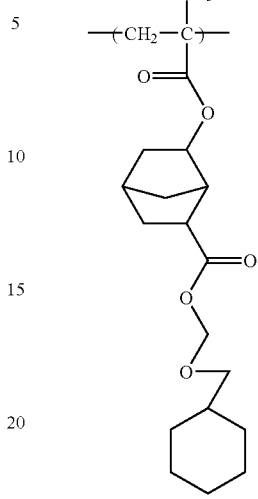
(a1-4-11)
(a1-4-9)
(a1-4-12)
(a1-4-10)
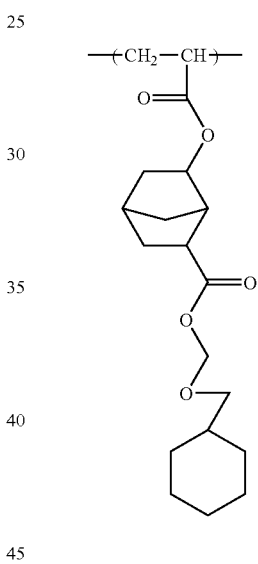
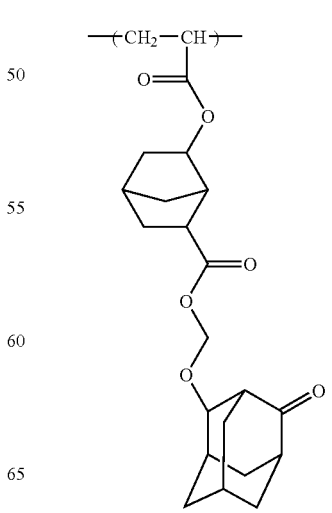
(a1-4-13)

(a1-4-14)
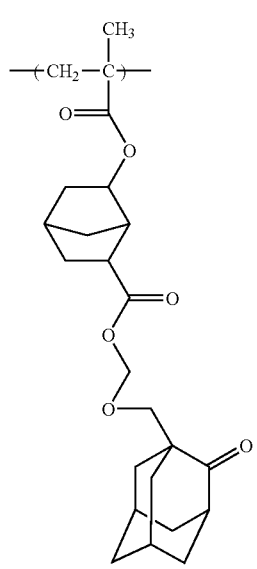
(a1-4-15)
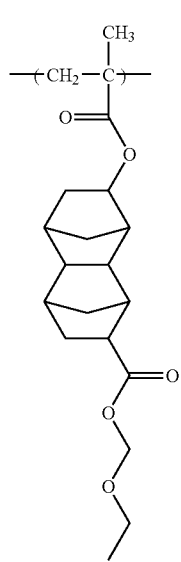
(a1-4-16)
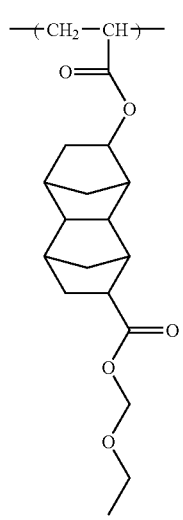
(a1-4-17)
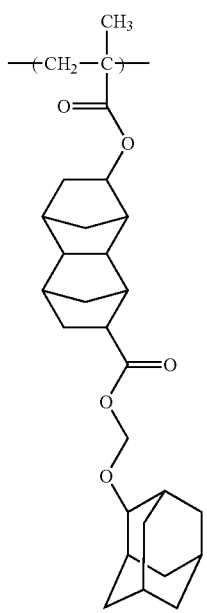
[Chemical Formula 22.]
(a1-4-18)
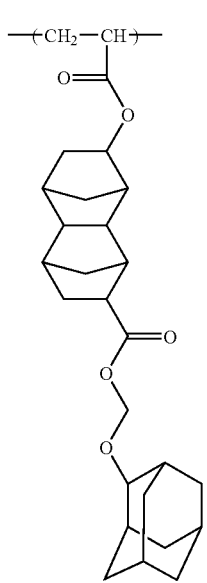

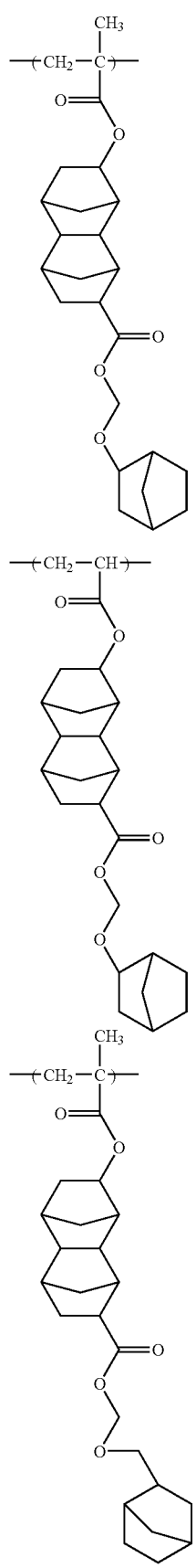

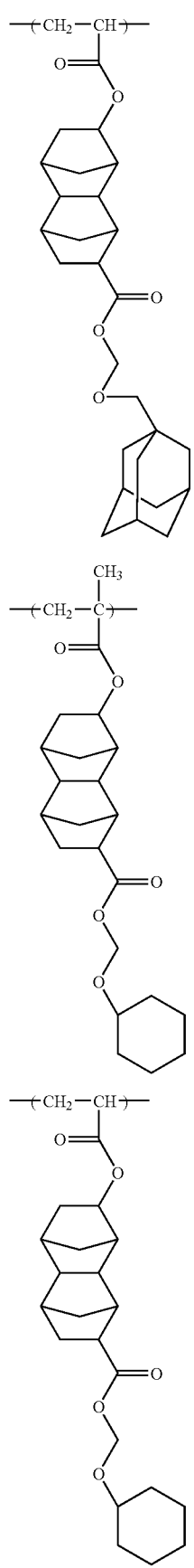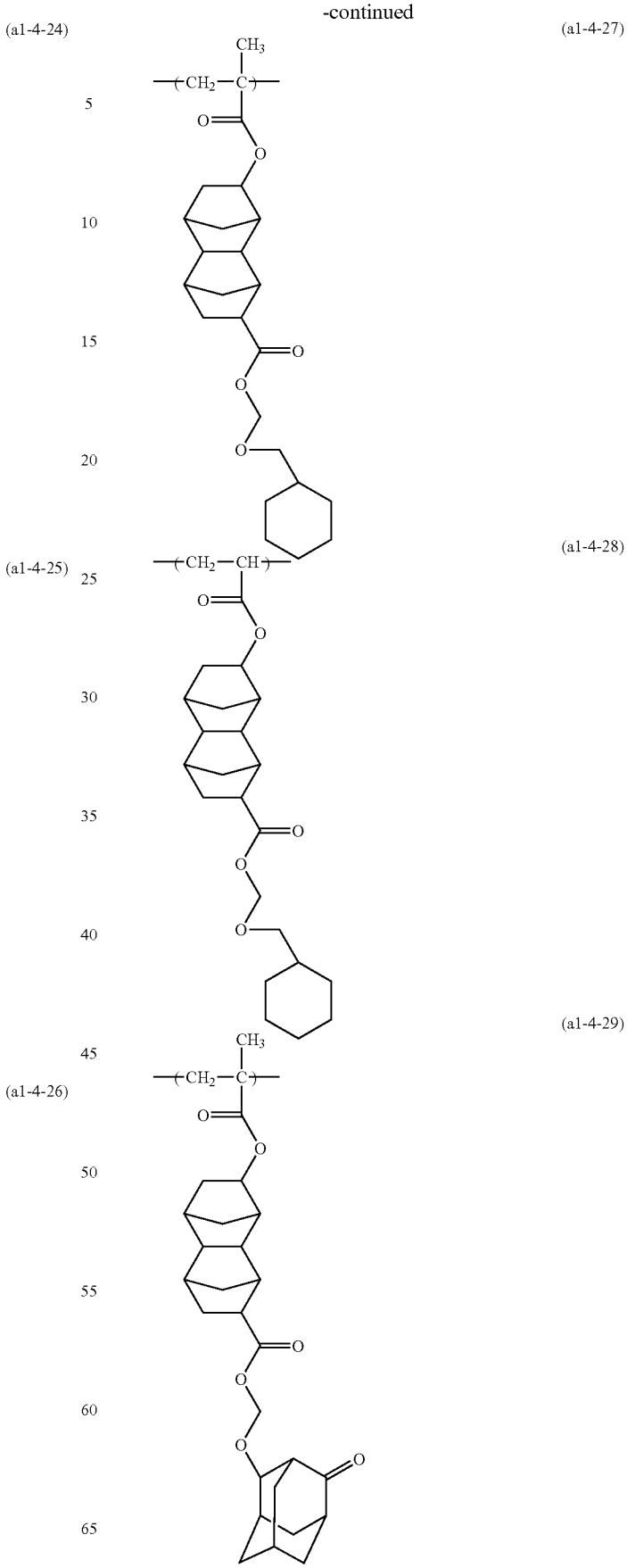

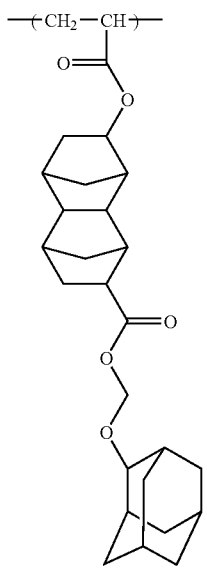

(a1-4-30)

Among these, structural units represented by general formula (a1-1) are preferable. More specifically, at least one structural unit selected from the group consisting of structural units represented by formulas (a1-1-1) to (a-1-1-6) and (a1-1-35) to (a1-1-41) is more preferable.

Further, as the structural unit (a1), structural units represented by general formula (a1-1-01) shown below which includes the structural units represented by formulas (a1-1-1) to (a1-1-4), and structural units represented by general formula (a1-1-02) shown below which includes the structural units represented by formulas (a1-1-35) to (a1-1-41) are also preferable.

[Chemical Formula 23.]

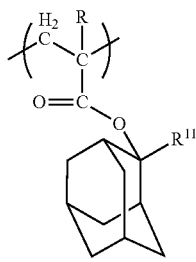

(a-1-01)

wherein R represents a hydrogen atom, a lower alkyl group or a halogenated lower alkyl group; and $R^{11}$ represents a lower alkyl group.

[Chemical Formula 24.]

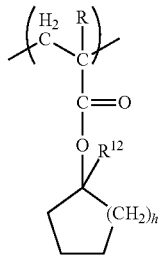

(a1-1-02)

wherein R represents a hydrogen atom, a lower alkyl group or a halogenated lower alkyl group; $R^{12}$ represents a lower alkyl group; and h represents an integer of 1 to 3.

In general formula (a1-1-01), R is as defined above. The lower alkyl group for $R^{11}$ is the same as the lower alkyl group for R above, preferably a methyl group or an ethyl group, and most preferably a methyl group.

In general formula (a1-1-02), R is as defined above. The lower alkyl group for $R^{12}$ is the same as the lower alkyl group for R above. $R^{12}$ is preferably a methyl group or an ethyl group, and most preferably an ethyl group. h is preferably 1 or 2, and most preferably 2.

As the structural unit (a1), one type may be used alone, or two or more types may be used in combination.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a resist composition prepared from the component (A1). On the other hand, by making the amount of the structural unit (a1) no more than the upper limit of the above-mentioned range, a good balance can be achieved with the other structural units.

Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include groups in which one hydrogen atom has been removed from a monocyclic lactone such as γ-butyrolactone or mevalonic lactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 25.]

(a2-1)
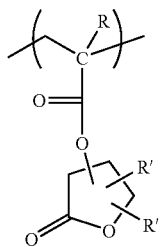

(a2-2)
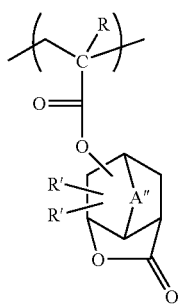

(a2-3)
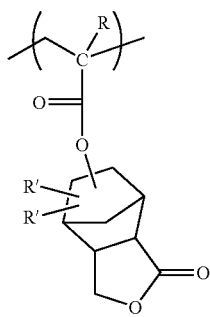

(a2-4)
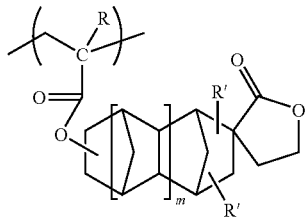

(a2-5)
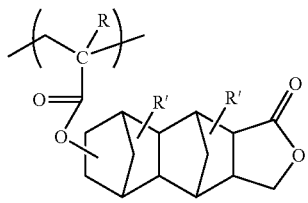

wherein R represents a hydrogen atom, a lower alkyl group or a halogenated lower alkyl group; R' represents a hydrogen atom, a lower alkyl group, an alkoxy group of 1 to 5 carbon atoms or —COOR", wherein R" represents a hydrogen atom or a linear, branched or cyclic alkyl group of 1 to 15 carbon atoms; m represents 0 or 1; and A" represents an alkylene group of 1 to 5 carbon atoms which may contain an oxygen atom or a sulfur atom, an oxygen atom or a sulfur atom.

In general formulas (a2-1) to (a2-5), R is the same as R in the structural unit (a1).

The lower alkyl group for R' is the same as the lower alkyl group for R in the structural unit (a1).

When R" is a linear or branched alkyl group, it preferably has 1 to 10 carbon atoms, more preferably 1 to 5 carbon atoms.

When R" is a cyclic alkyl group, it preferably has 3 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

In the structural units represented by general formulas (a2-1) to (a2-5), in consideration of industrial availability, R' is preferably a hydrogen atom.

Specific examples of alkylene groups of 1 to 5 carbon atoms for A" include a methylene group, ethylene group, n-propylene group, isopropylene group, —O—CH$_2$—, —CH$_2$—O—CH$_2$—, —S—CH$_2$— and —CH$_2$—S—CH$_2$—.

Specific examples of structural units represented by general formulas (a2-1) to (a2-5) above are shown below.

[Chemical Formula 26.]

(a2-1-1)
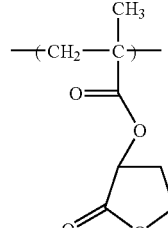

(a2-1-2)
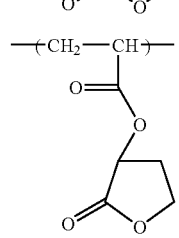

(a2-1-3)
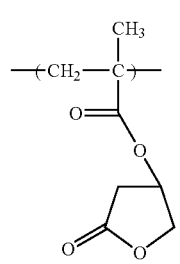

(a2-1-4) 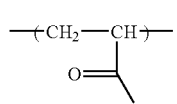
(a2-1-5) 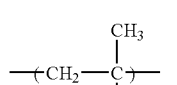
(a2-1-6) 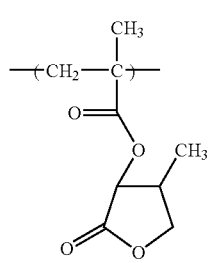
[Chemical Formula 27.]
(a2-2-1) 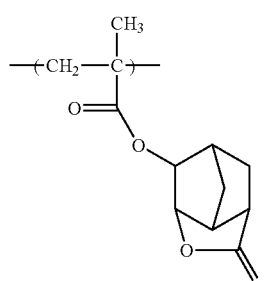
(a2-2-2) 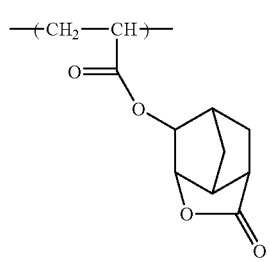
(a2-2-3) 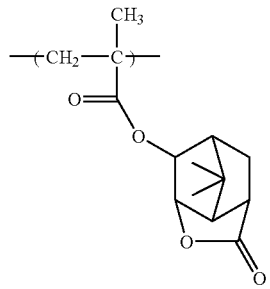
(a2-2-4) 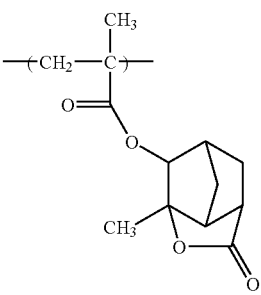
(a2-2-5) 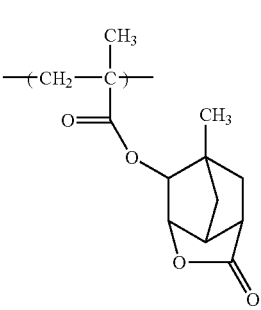
(a2-2-6) 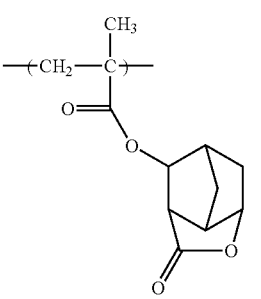
(a2-2-7) 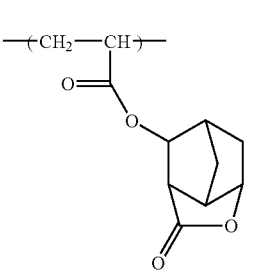
(a2-2-8) 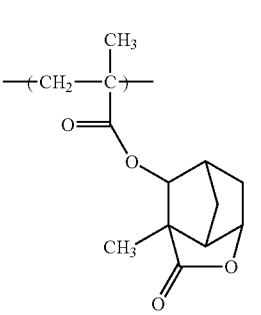

(a2-2-9)
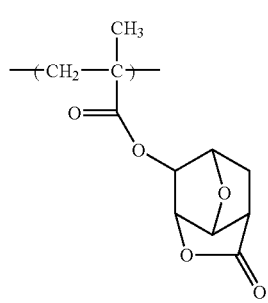
(a2-2-10)
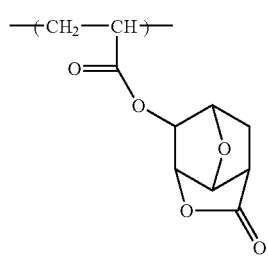
(a2-2-11)
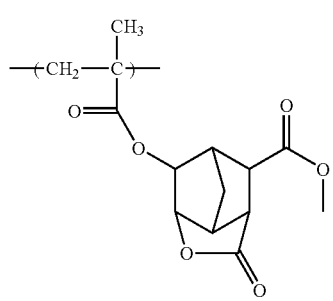
(a2-2-12)
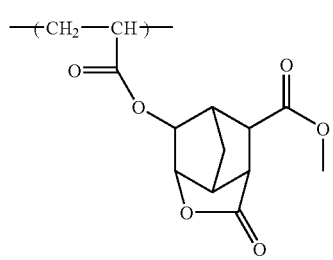
(a2-2-13)
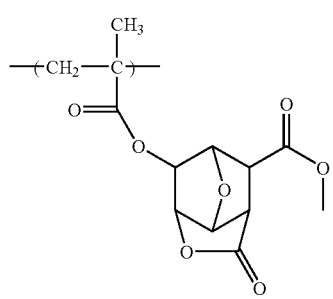
(a2-2-14)
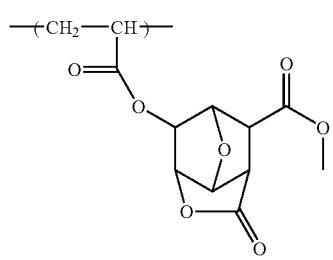
[Chemical Formula 28.]
(a2-3-1)
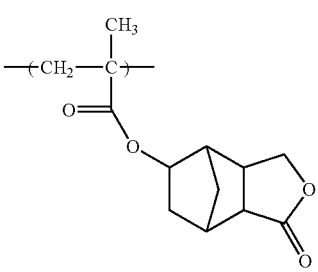
(a2-3-2)
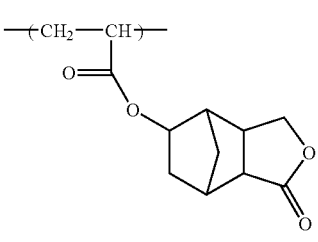
(a2-3-3)
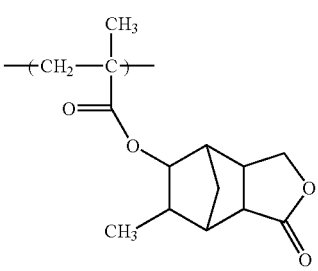
(a2-3-4)
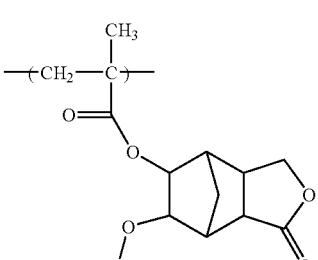
(a2-3-5)
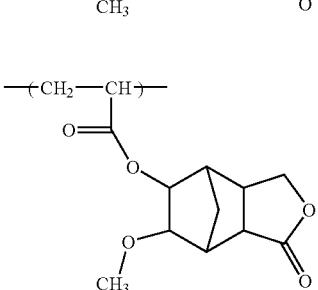
(a2-3-6)
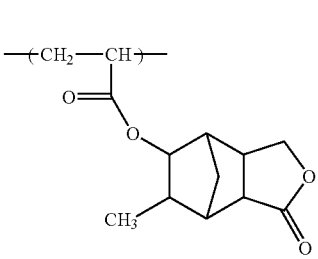

-continued
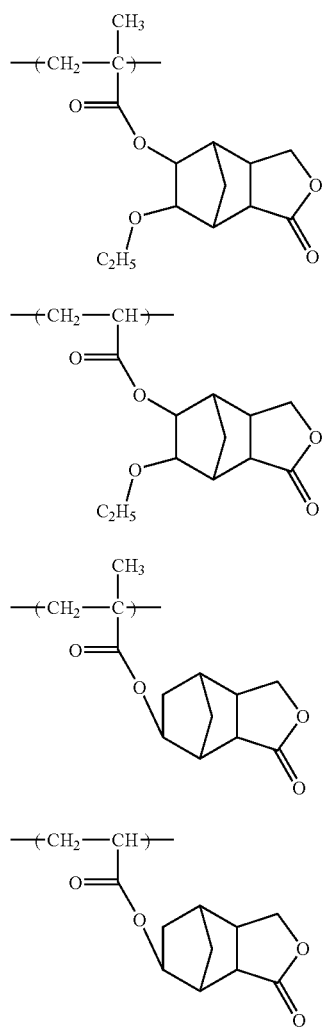
(a2-3-7)
(a2-3-8)
(a2-3-9)
(a2-3-10)
[Chemical Formula 29.]
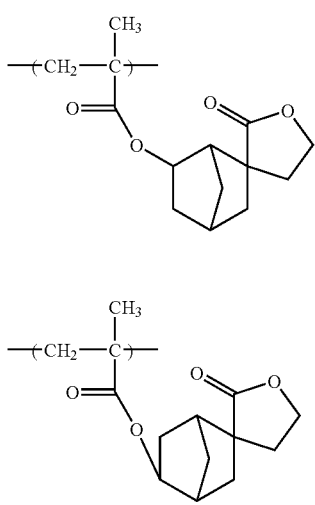
(a2-4-1)
(a2-4-2)
-continued
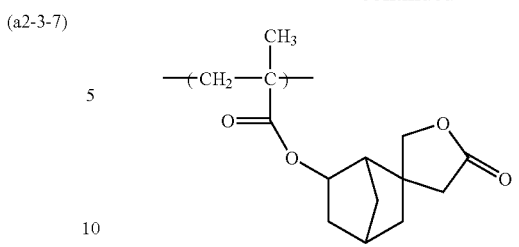
(a2-4-3)
(a2-4-4)
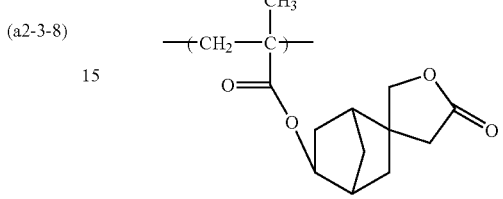
(a2-4-5)
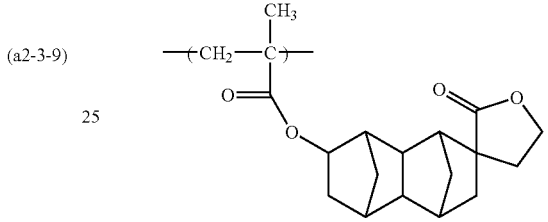
(a2-4-6)
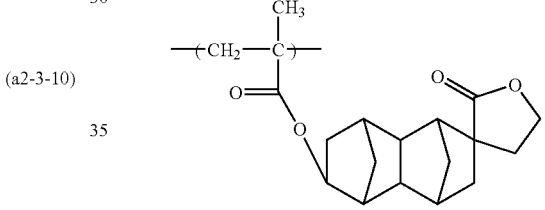
(a2-4-7)
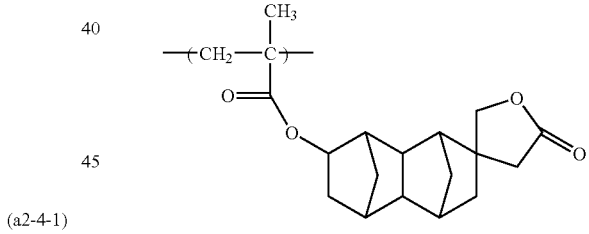
(a2-4-8)
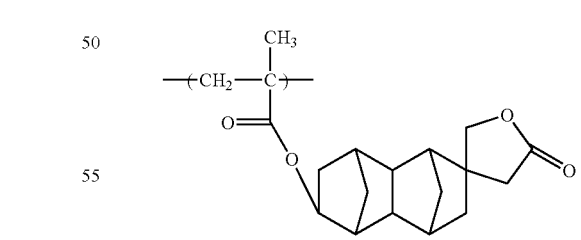
(a2-4-9)
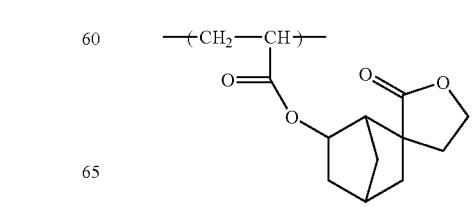

-continued

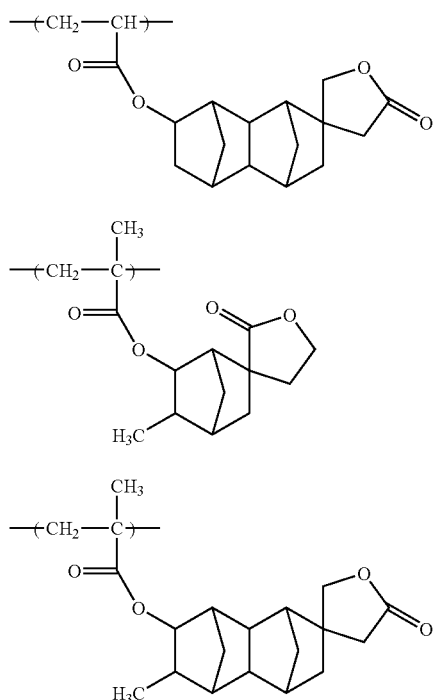

(a2-4-10)
(a2-4-11)
(a2-4-12)

[Chemical Formula 30.]

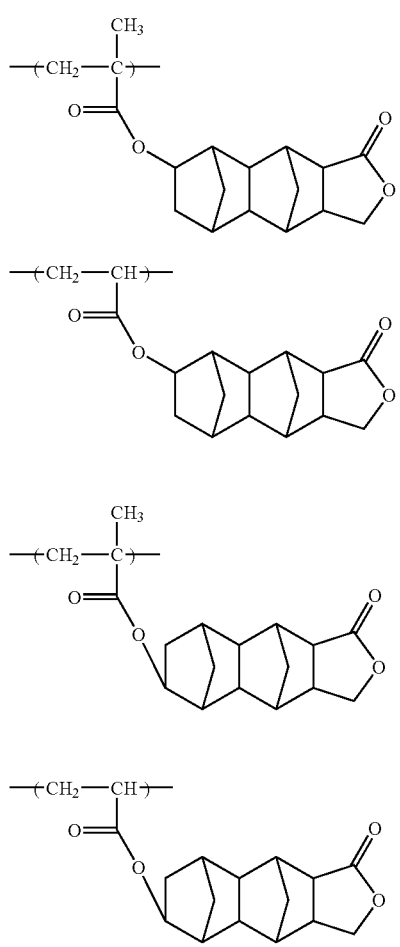

(a2-5-1)
(a2-5-2)
(a2-5-3)
(a2-5-4)

-continued

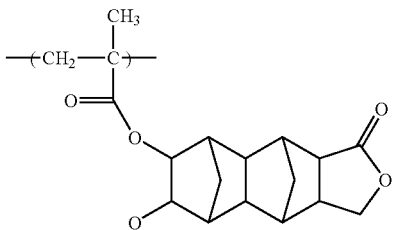

(a2-5-5)

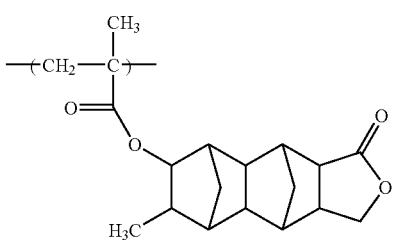

(a2-5-6)

As the structural unit (a2), at least one structural unit selected from the group consisting of formulas (a2-1) to (a2-5) is preferable, and at least one structural unit selected from the group consisting of formulas (a2-1) to (a2-3) is more preferable. Specifically, it is preferable to use at least one structural unit selected from the group consisting of formulas (a2-1-1), (a2-1-2), (a2-2-1), (a2-2-2), (a2-2-9), (a2-2-10), (a2-3-1), (a2-3-2), (a2-3-9) and (a2-3-10).

As the structural unit (a2), one type of structural unit may be used, or two or more types may be used in combination.

In the component (A1), the amount of the structural unit (a2) based on the combined total of all structural units constituting the component (A1) is preferably 5 to 60 mol %, more preferably 10 to 50 mol %, and still more preferably 20 to 50 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

Structural Unit (a3):

The structural unit (a3) is a structural unit derived from an acrylate ester containing a polar group-containing aliphatic hydrocarbon group.

When the component (A1) includes the structural unit (a3), the hydrophilicity of the component (A1) is improved, and hence, the compatibility of the component (A1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), and (a3-3) shown below are preferable.

[Chemical Formula 31.]

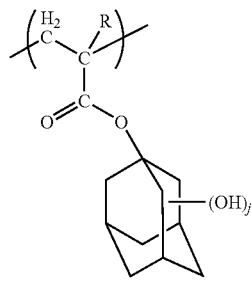

(a3-1)

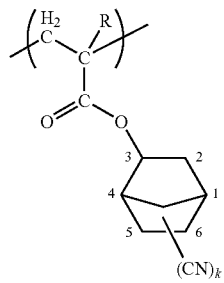

(a3-2)

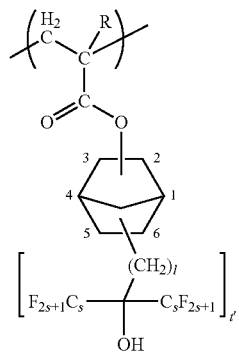

(a3-3)

wherein R is as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1, l is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol is preferably bonded to the 5th or 6th position of the norbornyl group.

In the component (A1), as the structural unit (a3), one type of structural unit may be used, or two or more types may be used in combination.

When the component (A1) contains the structural unit (a3), the amount of structural unit (a3) based on the combined total of all structural units constituting the component (A1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 32.]

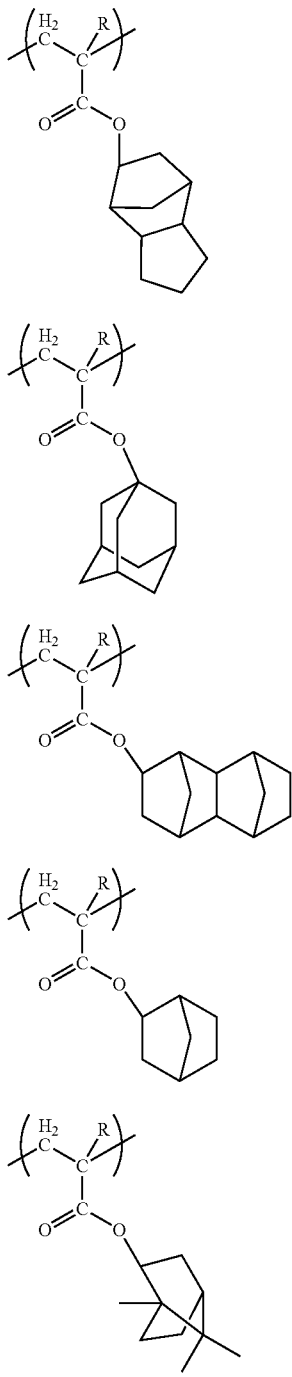

(a4-1)

(a4-2)

(a4-3)

(a4-4)

(a4-5)

wherein R is as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the present invention, the component (A1) preferably contains a copolymer having the structural units (a1), (a2) and (a3). Examples of such a copolymer include a copolymer consisting of the structural units (a1) and (a2) and (a3), and a copolymer consisting of the structural units (a1), (a2), (a3) and (a4).

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By making the weight average molecular weight no more than the upper limit of the above-mentioned range, the component (A1) exhibits satisfactory solubility in a resist solvent when used as a resist. On the other hand, by making the weight average molecular weight at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

[Component (A2)]

As the component (A2), it is preferable to use a compound that has a molecular weight of at least 500 and less than 2,000, contains a hydrophilic group, and also contains an acid dissociable, dissolution inhibiting group described above in connection with the component (A1). Specific examples include compounds containing a plurality of phenol skeletons in which a part of the hydrogen atoms within hydroxyl groups have been substituted with the aforementioned acid dissociable, dissolution-inhibiting groups.

Examples of the component (A2) include low molecular weight phenolic compounds in which a portion of the hydroxyl group hydrogen atoms have been substituted with an aforementioned acid dissociable, dissolution inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl) methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl) isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid dissociable, dissolution inhibiting group, and suitable examples include the groups described above.

As the component (A), one type may be used, or two or more types may be used in combination.

Among the above-mentioned examples, as the component (A), a base component that exhibits increased solubility in an alkali developing solution under action of acid is preferable, and it is particularly desirable that the component (A) contain the component (A1).

In the resist composition of the present invention, the amount of the component (A) can be appropriately adjusted depending on the thickness of the resist film to be formed, and the like.

<Component (B)>

As the component (B), there is no particular limitation, and any of the known acid generators used in conventional chemically amplified resist compositions can be used. Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator a compound represented by general formula (b-1) or (b-2) shown below can be preferably used.

[Chemical Formula 33.]

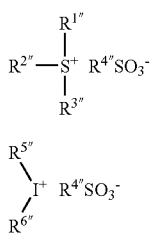

(b-1)

(b-2)

wherein $R^{1\prime\prime}$ to $R^{3\prime\prime}$, $R^{5\prime\prime}$ and $R^{6\prime\prime}$ each independently represents an aryl group or alkyl group, wherein two of $R^{1\prime\prime}$ to $R^{3\prime\prime}$ in formula (b-1) may be bonded to each other to form a ring with the sulfur atom; and $R^{4\prime\prime}$ represents a linear, branched or cyclic alkyl group or fluorinated alkyl group, with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ each independently represents an aryl group or an alkyl group. In formula (b-1), two of $R^{1\prime\prime}$ to $R^{3\prime\prime}$ in formula (b-1) may be bonded to each other to form a ring with the sulfur atom.

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, an aryl group having 6 to 20 carbon atoms may be used in which some or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, and most preferably a methoxy group, an ethoxy group, an n-propoxy group, an iso-propoxy group, an n-butoxy group or a tert-butoxy group.

The halogen atom, with which hydrogen atoms of the aryl group may be substituted, is preferably a fluorine atom.

The alkyl group for $R^{1\prime\prime}$ to $R^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is particularly desirable that each of $R^{1\prime\prime}$ to $R^{3\prime\prime}$ is a phenyl group or a naphthyl group.

When two of $R^{1\prime\prime}$ to $R^{3\prime\prime}$ in formula (b-1) are bonded to each other to form a ring with the sulfur atom, it is preferable that the two of $R^{1\prime\prime}$ to $R^{3\prime\prime}$ form a 3 to 10-membered ring including the sulfur atom, and it is particularly desirable that the two of $R^{1\prime\prime}$ to $R^{3\prime\prime}$ form a 5 to 7-membered ring including the sulfur atom. When two of $R^{1\prime\prime}$ to $R^{3\prime\prime}$ in formula (b-1) are bonded to each other to form a ring with the sulfur atom, the remaining one of $R^{1\prime\prime}$ to $R^{3\prime\prime}$ is preferably an aryl group. As the aryl group, the same aryl groups as those described above for $R^{1\prime\prime}$ to $R^{3\prime\prime}$ can be used.

$R^{4\prime\prime}$ represents a linear, branched or cyclic alkyl or fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group, as described for $R^{1\prime\prime}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (percentage of fluorine atoms within the alkyl group) is preferably from 10 to 100%, more preferably from 50 to 100%, and it is particularly desirable that all hydrogen atoms are substituted with fluorine atoms (i.e., the fluorinated alkyl group is a perfluoroalkyl group) because the acid strength increases.

$R^{4\prime\prime}$ is most preferably a linear or cyclic alkyl group or fluorinated alkyl group.

In formula (b-2), $R^{5\prime\prime}$ and $R^{6\prime\prime}$ each independently represents an aryl group or alkyl group. At least one of $R^{5\prime\prime}$ and $R^{6\prime\prime}$ represents an aryl group. It is preferable that both of $R^{5\prime\prime}$ and $R^{6\prime\prime}$ represent an aryl group.

As the aryl group for $R^{5\prime\prime}$ and $R^{6\prime\prime}$, the same aryl groups as those for $R^{1\prime\prime}$ to $R^{3\prime\prime}$ can be used.

As the alkyl group for $R^{5\prime\prime}$ and $R^{6\prime\prime}$, the same alkyl groups as those for $R^{1\prime\prime}$ to $R^{3\prime\prime}$ can be used.

It is particularly desirable that both of $R^{5\prime\prime}$ and $R^{6\prime\prime}$ represents a phenyl group.

As $R^{4\prime\prime}$ in formula (b-2), the same groups as those described above for $R^{4\prime\prime}$ in formula (b-1) can be used.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

[Chemical Formula 34.]

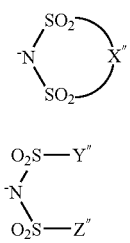

wherein X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Y" and Z" each independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group of X" or those of the alkyl group of Y" and Z" within the range of the number of carbon atoms, the better the solubility in a resist solvent.

Further, in the alkylene group of X" or the alkyl group of Y" and Z", it is preferable that the number of hydrogen atoms substituted with fluorine atoms is as large as possible, as the acid strength increases, and the transparency to high energy radiation of 200 nm or less or electron beam is improved. The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by general formula (b-5) or (b-6) shown below may be used.

[Chemical Formula 35.]

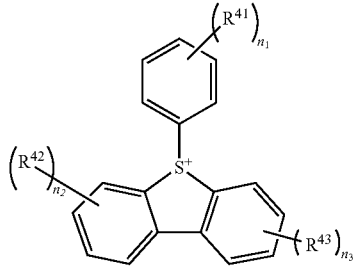

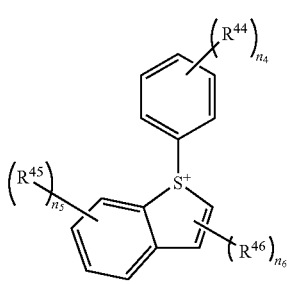

(b-6)

wherein $R^{41}$ to $R^{46}$ each independently represents an alkyl group, an acetyl group, an alkoxy group, a carboxy group, a hydroxyl group or a hydroxyalkyl group; $n_1$ to $n_5$ each independently represents an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, hydroxyethyl group and hydroxypropyl group.

If there are two or more of an individual $R^{41}$ to $R^{46}$ group, as indicated by the corresponding value of $n_1$ to $n_6$, then the two or more of the individual $R^{41}$ to $R^{46}$ group may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties ($R^{4"}SO_3^-$) for onium salt-based acid generators represented by general formula (b-1) or (b-2) shown above; and anion moieties represented by general formula (b-3) or (b-4) shown above. Among these, fluorinated alkylsulfonic acid ions are preferable, more preferably fluorinated alkylsulfonic acid ions of 1 to 4 carbon atoms, and linear perfluoroalkylsulfonic acid ions of 1 to 4 carbon atoms are particularly desirable. Specific examples include a trifluoromethylsulfonic acid ion, heptafluoro-n-propylsulfonic ion and nonafluoro-n-butylsulfonic acid ion.

In the present description, an oximesulfonate-based acid generator is a compound having at least one group represented by general formula (B-1) shown below, and has a feature of generating acid by irradiation. Such oxime-sulfonate-based acid generators are widely used for a chemically amplified resist composition, and can be appropriately selected.

[Chemical Formula 36.]

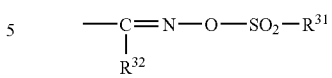

(B-1)

wherein $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "having a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 37.]

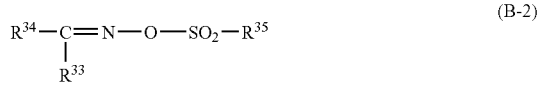

(B-2)

wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 38.]

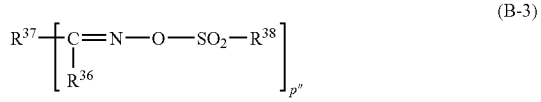

(B-3)

wherein $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be shown.

[Chemical Formula 39.]

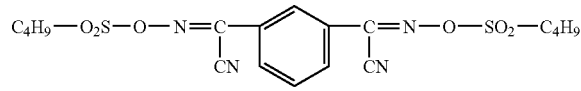

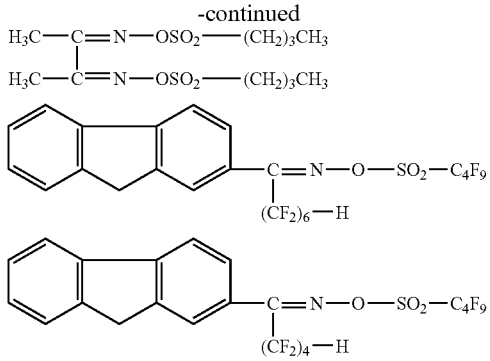

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be used.

As the component (B), one type of acid generator may be used, or two or more types may be used in combination.

In the present invention, as the component (B), it is preferable to use an onium salt-based acid generator having a fluorinated alkylsulfonic acid ion which may have a substituent as the anion moiety.

In the resist composition for immersion exposure according to the present invention, the amount of the component (B) is preferably 0.5 to 30 parts by weight, and more preferably 1 to 10 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Component (C)>

In the present invention, the component (C) is a fluorine-containing compound represented by a general formula (c-1) shown below that is decomposable in an alkali developing solution.

[Chemical Formula 40.]

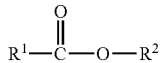

(c-1)

wherein $R^1$ represents an organic group which may have a polymerizable group, with the proviso that said polymerizable group has a carbon-carbon multiple bond, and the carbon atoms forming the multiple bond are not directly bonded to the carbon atom with the —C(=O)— group in general formula (c-1); and $R^2$ represents an organic group having a fluorine atom.

In the formation of a resist pattern, by virtue of the resist composition for immersion exposure according to the present invention containing the component (C), a resist film can be formed which is hydrophobic during immersion exposure, and becomes hydrophilic during alkali developing.

In the present description and claims, a fluorine-containing compound that is "decomposable in an alkali developing solution" refers to a fluorine-containing compound that is decomposable by action of an alkali developing solution (preferably decomposable by action of a 2.38% by weight aqueous solution of tetramethylammonium hydroxide (TMAH) at 23° C.), and exhibits increased alkali solubility in the alkali developing solution. The component (C) is a compound that is hardly soluble in an alkali developing solution prior to decomposition, and when the component (C) is decomposed by action of the developing solution, a carboxy group which is a hydrophilic group is generated, thereby exhibiting increased solubility in the alkali developing solution.

In general formula (c-1), $R^1$ represents an organic group which may contain a polymerizable group.

A "polymerizable group" refers to a group that renders a compound having the group polymerizable by a radical polymerization or the like.

The polymerizable group has a carbon-carbon multiple bond, and the carbon atoms forming the multiple bond are not directly bonded to the carbon atom within the —C(=O)— group in general formula (c-1). More specifically, when $R^1$ represents an organic group having a polymerizable group, $R^1$ is an organic group which has a group other than a polymerizable group between the carbon atoms forming a multiple bond and the carbon atom within the —C(=O)— group in general formula (c-1).

The component (C) may be either a polymeric compound (polymer, copolymer) including a recurring unit, or a low molecular weight compound (non-polymer).

Hereafter, when the component (C) is a low molecular weight compound, the component (C) will be frequently referred to as "fluorine-containing compound (C1)". On the other hand, when the component (C) is a polymeric compound, the component (C) will be frequently referred to as "fluorine-containing compound (C2)".

[Fluorine-Containing Compound (C1)]

In a fluorine-containing compound (C1), as $R^1$ in general formula (c-1) above, an organic group containing a polymerizable group is preferable. That is, $R^1$ is preferably an organic group constituted of a polymerizable group and a group other than polymerizable groups.

Typically, as an organic group containing a polymerizable group for $R^1$, an organic group containing a polymerizable group which is used as a monomer can be used. An example of such an organic group includes a group having an ethylenic unsaturated double bond.

Examples of groups having an ethylenic unsaturated double bond include a group represented by the formula $CH_2=CR-A_{aryl}$- (wherein $A_{aryl}$ represents an aromatic cyclic group which may have a substituent) and a group represented by the formula $CH_2=CR-C(=O)-O-$.

In the formula above, R is as defined for R described above in connection with the component (A), namely, a hydrogen atom, a lower alkyl group or a halogenated lower alkyl group.

Specific examples of lower alkyl groups for R include linear or branched alkyl groups such as a methyl group, ethyl group, propyl group, isopropyl group, n-butyl group, isobutyl group, tert-butyl group, pentyl group, isopentyl group, and neopentyl group.

Specific examples of halogenated lower alkyl groups for R include groups in which a part or all of the hydrogen atoms of the aforementioned lower alkyl group are substituted with halogen atoms. Examples of halogen atoms include fluorine atoms, chlorine atoms, bromine atoms and iodine atoms, and fluorine atoms are particularly desirable.

As R, a hydrogen atom, a lower alkyl group or a fluorinated lower alkyl group is preferable, and a hydrogen atom or a methyl group is more preferable.

$A_{aryl}$ represents an aromatic cyclic group which may have a substituent. Specifically, as $A_{aryl}$, an aromatic hydrocarbon ring (which may have a substituent) having 2 hydrogen atoms removed therefrom can be used.

The ring skeleton of the aromatic cyclic group for $A_{aryl}$ preferably has 5 to 16 carbon atoms. Examples of ring skeletons include a benzene ring, a naphthalene ring, a phenanthrene ring and an anthracene ring. Among these, a benzene ring or a naphthalene ring is particularly desirable.

Examples of substituents which an aromatic cyclic group for $A_{aryl}$ may have include a halogen atom, an alkyl group, an alkoxy group, a halogenated lower alkyl group and an oxygen atom (=O). Examples of halogen atoms include a fluorine atom, a chlorine atom, an iodine atom and a bromine atom. As the substituent which an aromatic cyclic group for $A_{aryl}$ may have, a fluorine atom is preferable.

$A_{aryl}$ may be either an aromatic cyclic group having no substituent, or an aromatic cyclic group having a substituent, although an aromatic cyclic group having no substituent is preferable.

When $A_{aryl}$ is an aromatic cyclic group having a substituent, the number of the substituent may be either 1 or at least 2, preferably 1 or 2, and more preferably 1.

Alternatively, as an organic group containing a polymerizable group for $R^1$, an organic group constituted of a group having an ethylenic unsaturated double bond and a group other than polymerizable groups can be preferably used.

Preferable examples of groups having an ethylenic unsaturated double bond include the aforementioned group represented by the formula $CH_2=CR-C(=O)-O-$ and the aforementioned group represented by the formula $CH_2=CR-A_{aryl}$- (wherein $A_{aryl}$ represents an aromatic cyclic group which may have a substituent).

It is preferable that each R independently represent a hydrogen atom or a methyl group. $A_{aryl}$ is as defined above.

As a group other than polymerizable groups, a divalent linkage group, preferably a divalent organic group having no acid dissociable portion, can be used. Preferable examples of such groups include a hydrocarbon group which may have a substituent, and a group containing a hetero atom.

An "acid dissociable portion" refers to a portion within the organic group which is dissociated from the organic group by action of acid generated by exposure.

(Hydrocarbon Group which May have a Substituent)

With respect to the group other than polymerizable groups, a hydrocarbon group "having has a substituent" refers to a hydrocarbon group in which a part or all of the hydrogen atoms within the hydrocarbon group has been substituted with an atom or group other than hydrogen.

The hydrocarbon group may be either an aliphatic hydrocarbon group, or an aromatic hydrocarbon group.

An aliphatic hydrocarbon group refers to a hydrocarbon group having no aromaticity. The aliphatic hydrocarbon group may be either saturated or unsaturated, but in general, the aliphatic hydrocarbon group is preferably saturated.

Specific examples of aliphatic cyclic groups include a linear or branched aliphatic hydrocarbon group and an aliphatic hydrocarbon group containing a ring in the structure thereof.

The linear or branched aliphatic hydrocarbon group preferably has 1 to 10 carbon atoms, more preferably 1 to 8, still more preferably 1 to 5, still more preferably 1 to 3, and most preferably 2.

As a linear aliphatic hydrocarbon group, a linear alkylene group is preferable, and specific examples include a methylene group, an ethylene group $[-(CH_2)_2-]$, a trimethylene group $[-CH_2CH_2CH_2-]$, a tetramethylene group $[-CH_2CH_2CH_2CH_2-]$ and a pentamethylene group $[-CH_2CH_2CH_2CH_2CH_2-]$.

As a branched aliphatic hydrocarbon group, a branched alkylene group is preferable, and specific examples include alkylmethylene groups such as $-CH(CH_3)-$, $-CH(CH_2CH_3)-$, $-C(CH_3)_2-$, $-C(CH_3)(CH_2CH_3)-$, $-C(CH_3)(CH_2CH_2CH_3)-$ and $-C(CH_2CH_3)_2$; alkylethylene groups such as $-CH(CH_3)CH_2-$, $-CH(CH_3)CH(CH_3)-$, $-C(CH_3)_2CH_2-$, and $-CH(CH_2CH_3)CH_2-$; alkyltrimethylene groups such as $-CH(CH_3)CH_2CH_2-$ and $-CH_2CH(CH_3)CH_2-$; and alkyltetramethylene groups such as $-CH(CH_3)CH_2CH_2CH_2-$ and $-CH_2CH(CH_3)CH_2CH_2-$. The alkyl group within the alkylalkylene group is preferably a linear alkyl group of 1 to 5 carbon atoms.

The linear or branched (chain-like) aliphatic hydrocarbon group may or may not have a substituent. Examples of substituents include a fluorine atom, a fluorinated alkyl group of 1 to 5 carbon atoms, and an oxygen atom (=O).

Examples of aliphatic hydrocarbon groups containing a ring include a cyclic aliphatic hydrocarbon group (an aliphatic hydrocarbon ring having 2 hydrogen atoms removed therefrom), a group in which the cyclic aliphatic hydrocarbon group is bonded to the terminal of the aforementioned chain-like aliphatic hydrocarbon group, and a group in which the cyclic aliphatic hydrocarbon group is present within the aforementioned chain-like aliphatic hydrocarbon group.

The cyclic aliphatic hydrocarbon group preferably has 3 to 20 carbon atoms, more preferably 3 to 12.

The cyclic aliphatic hydrocarbon group may be either a polycyclic group or a monocyclic group. As a monocyclic group, a monocycloalkane of 3 to 6 carbon atoms having 2 hydrogen atoms removed therefrom can be preferably used. Examples of monocycloalkanes include cyclopentane and cyclohexane.

As a polycyclic group, a polycycloalkane of 7 to 12 carbon atoms having 2 hydrogen atoms removed therefrom can be preferably used. Examples of polycycloalkanes include adamantane, isobornane, tricyclodecane and tetracyclododecane.

The cyclic aliphatic hydrocarbon group may or may not have a substituent. Examples of substituents include a lower alkyl group of 1 to 5 carbon atoms, a fluorine atom, a fluorinated alkyl group of 1 to 5 carbon atoms, and an oxygen atom (=O).

Examples of aromatic hydrocarbon groups include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which a part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

Among these examples, the aforementioned divalent aromatic hydrocarbon group is preferable, and an aromatic hydrocarbon group in which one hydrogen atom has been removed from a phenyl group, or an aromatic hydrocarbon group in which one hydrogen atom has been removed from a naphthyl group is particularly desirable.

The alkyl chain within the arylalkyl group preferably has 1 to 4 carbon atom, more preferably 1 or 2, and most preferably 1.

The aromatic hydrocarbon group may or may not have a substituent. Examples of substituents include a lower alkyl group of 1 to 5 carbon atoms, a fluorine atom, a fluorinated alkyl group of 1 to 5 carbon atoms, and an oxygen atom (=O).

Among the above-mentioned examples, as the hydrocarbon group which may have a substituent, a linear, branched or cyclic aliphatic hydrocarbon group or a divalent aromatic hydrocarbon group is preferable, and a methylene group, and ethylene group, —CH(CH$_3$)—, a group in which one hydrogen atom has been removed from a tetracyclododecanyl group, or an aromatic hydrocarbon group in which one hydrogen atom has been removed from a phenyl group is particularly desirable.

(Group Containing a Hetero Atom)

A hetero atom is an atom other than a carbon atom and a hydrogen atom, and examples thereof include an oxygen atom, a nitrogen atom, a sulfur atom and a halogen atom.

Examples of groups containing a hetero atom include —O—, —C(=O)—, —C(=O)—O—, a carbonate bond (—O—C(=O)—O—), —NH—, —NR$^{04}$— (wherein R$^{04}$ represents an alkyl group), —NH—C(=O)—, =N—, and a combination of any of these "groups" with a divalent hydrocarbon group.

As the divalent hydrocarbon group, the same groups as those described above for the hydrocarbon group which may have a substituent can be used, and a linear or branched aliphatic hydrocarbon group is preferable.

Among the above-mentioned examples, as the group containing a hetero atom, a combination of any of the aforementioned "groups" with a divalent hydrocarbon group is preferable. More specifically, it is particularly desirable to use a combination of any of the aforementioned "groups" with the aforementioned aliphatic hydrocarbon group, or a combination of the aforementioned aliphatic hydrocarbon group, any of the aforementioned "groups" and the aforementioned aliphatic hydrocarbon group. In general formula (c-1) above, R$^2$ represents an organic group having a fluorine atom.

An "organic group having a fluorine atom" refers to an organic group in which a part or all of the hydrogen atoms have been substituted with fluorine atoms.

As R$^2$, for example, a fluorinated hydrocarbon group which may or may not have a substituent can be preferably used. As R$^2$, a fluorinated, saturated hydrocarbon group or a fluorinated, unsaturated hydrocarbon group is more preferable, and a fluorinated, saturated hydrocarbon group is particularly desirable.

R$^2$ may be linear, branched or cyclic, and is preferably linear or branched.

Further, R$^2$ preferably has 1 to 20 carbon atoms, more preferably 1 to 15, still more preferably 1 to 10, and most preferably 1 to 5.

It is preferable that the organic group having a fluorine atom for R$^2$ has 25% or more of the hydrogen atoms within the organic group fluorinated, more preferably 50% or more, and most preferably 60% or more, as the hydrophobicity of the resist film during immersion exposure is enhanced.

Among the above-mentioned examples, as the fluorine-containing compound (C1), a compound represented by general formula (c-1-1) or (c-1-2) shown below can be preferably used (hereafter, this compound is referred to as "compound (C1-1)").

[Chemical Formula 41.]

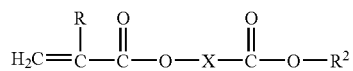

(c-1-1)

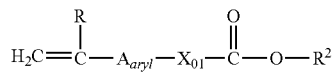

(c-1-2)

wherein each R independently represents a hydrogen atom, a lower alkyl group or a halogenated lower alkyl group; X represents a divalent organic group having no acid dissociable portion; A$_{aryl}$ represents an aromatic cyclic group which may have a substituent; X$_{01}$ represents a single bond or a divalent linkage group; and each R$^2$ independently represents an organic group having a fluorine atom.

In general formulas (c-1-1) and (c-1-2) above, R and R$^2$ are as defined above.

R is preferably a hydrogen atom or a methyl group.

R$^2$ is preferably a fluorinated hydrocarbon group, more preferably a fluorinated hydrocarbon group of 1 to 5 carbon atoms, and most preferably —CH$_2$—CF$_3$, —CH$_2$—CF$_2$—CF$_3$, —CH(CF$_3$)$_2$, —CH$_2$—CF$_2$—CF$_2$—CF$_3$ or —CH$_2$—CH$_2$—CF$_2$—CF$_2$—CF$_2$—CF$_3$.

In general formula (c-1-1) above, X represents a divalent organic group having no acid dissociable portion.

As X, the aforementioned hydrocarbon group which may have a substituent, or the aforementioned group containing a hetero atom can be preferably used.

In general formula (c-1-2), A$_{aryl}$ is as defined above.

In general formula (c-1-2), X$_{01}$ represents a single bond or a divalent linkage group. Examples of divalent linkage groups include an alkylene group of 1 to 10 carbon atoms, —O—, —C(=O)—, —C(=O)—O—, a carbonate bond (—O—C(=O)—O—), —NH—C(=O)—, and a combination of these groups, and a combination of —O— with an alkylene group of 1 to 12 carbon atoms is particularly desirable.

Examples of alkylene groups of 1 to 12 carbon atoms include linear, branched or cyclic alkylene groups, and a linear or branched alkylene group of 1 to 5 carbon atoms and a cyclic alkylene group of 4 to 12 carbon atoms are preferable.

Among the above-mentioned examples, as the compound (C1-1), a compound represented by general formula (c-1-10) or (c-1-11) shown below can be preferably used.

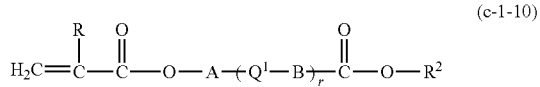
(c-1-10)

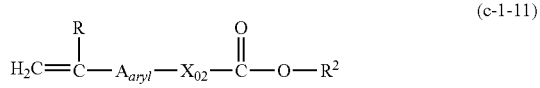
(c-1-11)

wherein R and $R^2$ are as defined above; each of A and B independently represents a divalent hydrocarbon group which may have a substituent; $Q^1$ represents a divalent linkage group containing an oxygen atom; r represents 0 or 1; $A_{aryl}$ represents an aromatic cyclic group which may have a substituent; and $X_{02}$ represents a single bond, $-(R^7)_{a0}-O-[C(=O)]_{b0}-R^8-$ or $-C(=O)-O-R^9-$.

In general formula (c-1-10) above, R and $R^2$ are as defined above.

In general formula (c-1-10) above, A represents a divalent hydrocarbon group which may have a substituent, preferably a linear alkylene group, a branched alkylene group, a cyclic alkylene group or the aromatic hydrocarbon group described above in the explanation of $R^1$ above, and most preferably an ethylene group, $-CH(CH_3)-$, a tetracyclododecanyl group in which one hydrogen atom have been removed therefrom, or a phenyl group in which one hydrogen atom has been removed therefrom.

In general formula (c-1-10) above, B represents a divalent hydrocarbon group which may have a substituent, preferably a linear alkylene group or a branched alkylene, and most preferably a methylene group or an ethylene group.

In general formula (c-1-10) above, $Q^1$ represents a divalent linkage group containing an oxygen atom, preferably $-O-$, $-C(=O)-$, $-C(=O)-O-$, $-O-C(=O)-$, a carbonate bond ($-O-C(=O)-O-$) or $-NH-C(=O)-$, and most preferably $-O-$, $-C(=O)-O-$ or $-O-C(=O)-$.

In general formula (c-1-10) above, r represents 0 or 1.

In general formula (c-1-11) above, R, $R^2$ and $A_{aryl}$ are as defined above.

$X_{02}$ represents a single bond, $-(R^7)_{a0}-O-[C(=O)]_{b0}-R^8-$ or $-C(=O)-O-R^9-$.

Each of $R^7$, $R^8$ and $R^9$ independently represents a linear, branched or cyclic alkylene group of 1 to 10 carbon atoms, and preferably a linear or branched alkylene group of 1 to 5 carbon atoms or a cyclic alkylene group of 4 to 10 carbon atoms.

a0 represents 0 or an integer of 1 to 5. b0 represents 0 or 1.

As the compound (C1-1), a compound represented by any one of general formulas (c-1-12) to (c-1-20) is particularly desirable.

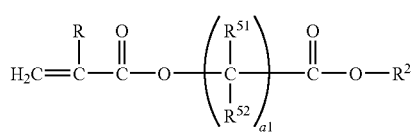
(c-1-12)

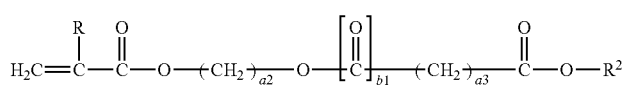
(c-1-13)

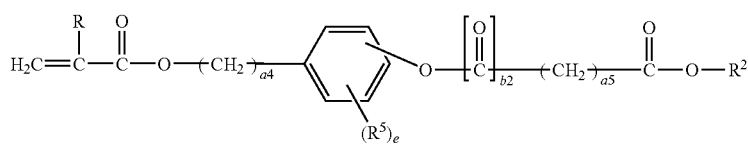
(c-1-14)

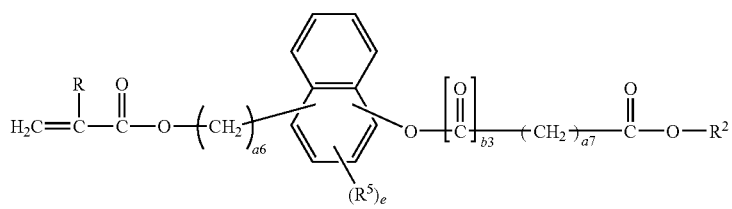
(c-1-15)

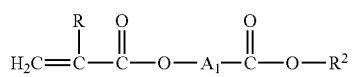
(c-1-16)

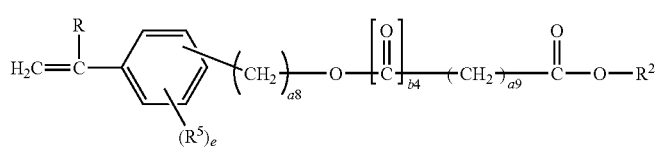
(c-1-17)

-continued

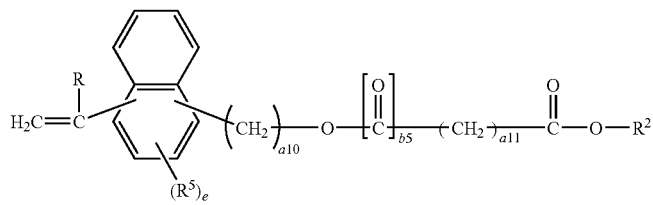
(c-1-18)

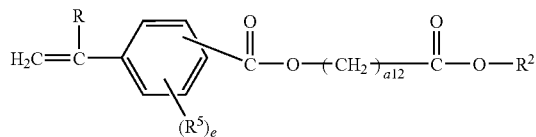
(c-1-19)

(c-1-20)

In general formulas (c-1-12) to (c-1-20) above, R and $R^2$ are as defined above; each of $R^{51}$ and $R^{52}$ independently represents a hydrogen atom or a lower alkyl group; each of a1, a2, a3, a5, a7 a9 and a11 to a13 independently represents an integer of 1 to 5; each of a4, a6, a8 and a10 independently represents 0 or an integer of 1 to 5; each of b1 to b5 independently represents 0 or 1; $R^5$ represents a substituent; e represents an integer of 0 to 2; and $A_1$ represents a cyclic alkylene group of 4 to 20 carbon atoms.

In general formula (c-1-12) above, as the lower alkyl group for $R^{51}$ and $R^{52}$, the same lower alkyl groups as those for R above can be used, preferably a methyl group or an ethyl group, and most preferably a methyl group. In the present invention, it is preferable that at least one of $R^{51}$ and $R^{52}$ be a hydrogen atom.

In general formula (c-1-12) above, a1 is preferably 1 to 3, more preferably 1 or 2.

In general formula (c-1-13) above, it is preferable that each of a2 and a3 independently represent 1 to 3, more preferably 1 or 2. b1 represents 0 or 1.

In general formula (c-1-14) above, a4 is preferably 0 or 1 to 3, more preferably 0, 1 or 2, and most preferably 0 or 1. a5 is preferably 1 to 3, more preferably 1 or 2. As the substituent for $R^5$, for example, a halogen atom, a lower alkyl group, an alkoxy group of 1 to 5 carbon atoms, a halogenated lower alkyl group, or an oxygen atom (=O) can be used. Examples of halogen atoms include a fluorine atom, a chlorine atom, an iodine atom and a bromine atom. e is preferably 0 or 1, and most preferably 0 from industrial viewpoint. b2 is preferably 0.

In general formula (c-1-15) above, a6 is preferably 0 or 1 to 3, more preferably 0, 1 or 2, and most preferably 0 or 1. a7 is preferably 1 to 3, more preferably 1 or 2. b3 is preferably 0. $R^5$ and e are as defined above.

In general formula (c-1-16) above, $A_1$ represents a cyclic alkylene group of 4 to 20 carbon atoms, preferably a cyclic alkylene group of 5 to 15 carbon atoms, and more preferably a cyclic alkylene group of 6 to 12 carbon atoms. Specific examples cyclic alkylene groups include those described above as the "cyclic aliphatic hydrocarbon group" for the aforementioned hydrocarbon group which may have as substituent.

In general formula (c-1-17) above, a8 is preferably 0 or 1 to 3, more preferably 0, 1 or 2, and most preferably 0 or 1. a9 is preferably 1 to 3, more preferably 1 or 2. b4 is preferably 0. $R^5$ and e are as defined above.

In general formula (c-1-18) above, a10 is preferably 0 or 1 to 3, more preferably 0, 1 or 2, and most preferably 0 or 1. a11 is preferably 1 to 3, more preferably 1 or 2. b5 is preferably 0. $R^5$ and e are as defined above.

In general formula (c-1-19) above, a12 is preferably 1 to 3, more preferably 1 or 2. $R^5$ and e are as defined above.

In general formula (c-1-20) above, a13 is preferably 1 to 3, more preferably 1 or 2. $R^5$ and e are as defined above.

Specific examples of compounds represented by general formulas (c-1-12) to (c-1-20) are shown below.

[Chemical Formula 45.]

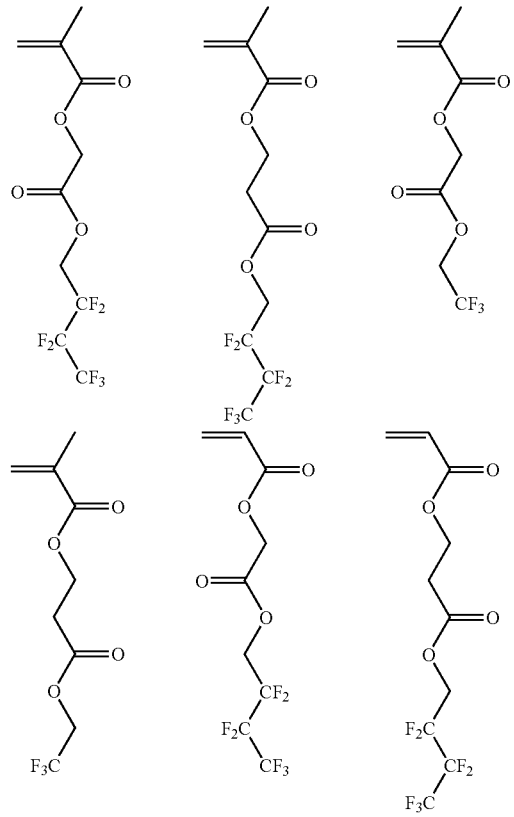

-continued

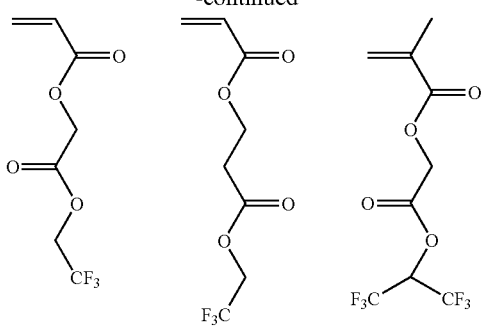
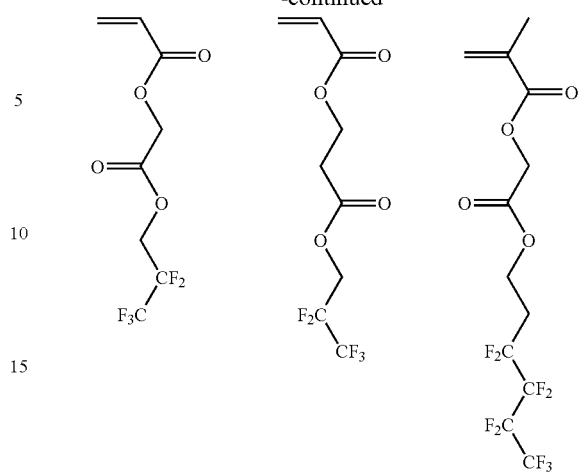
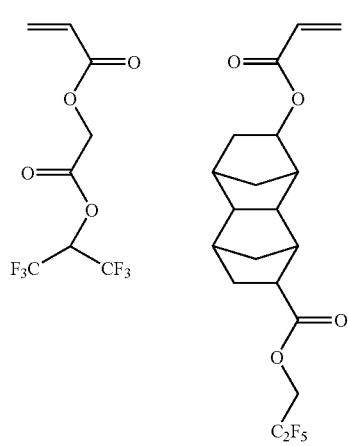
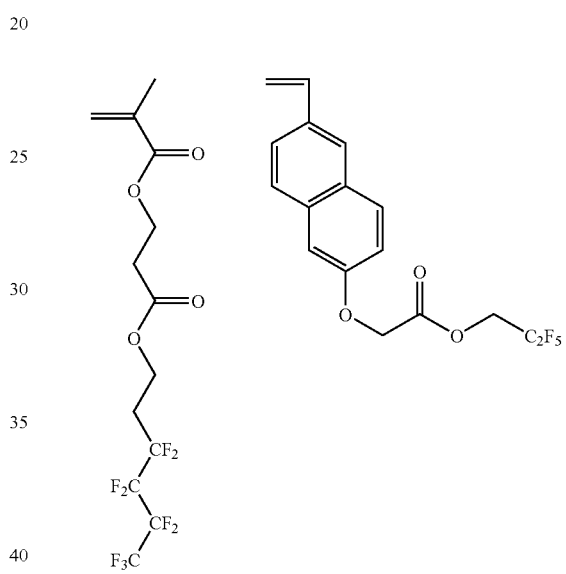
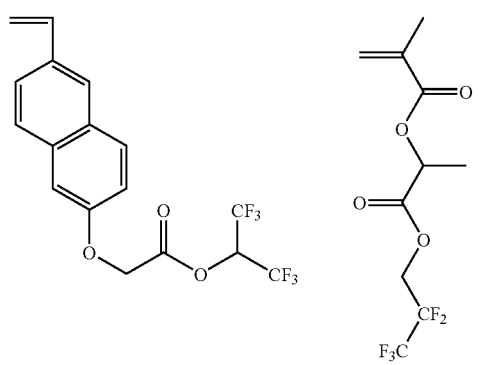
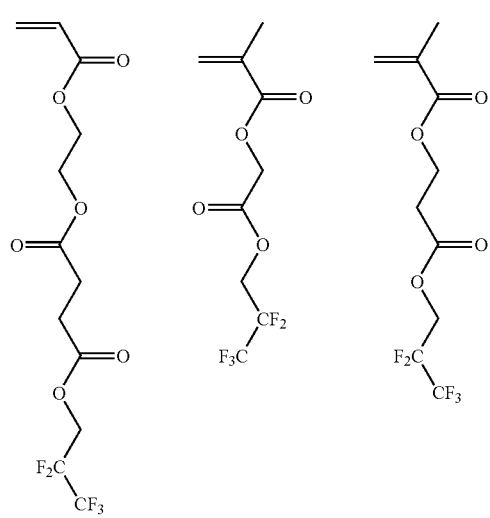

The fluorine-containing compound (C1) described above per se can be preferably used as an additive for a resist composition for immersion exposure.

When the fluorine-containing compound (C1) is a compound containing a polymerizable group such as the aforementioned compound (C1-1), the fluorine-containing compound (C1) can be either polymerized alone, or copolymerized with another polymerizable compound to obtain a polymeric compound. Such a polymeric compound, like the fluorine-containing compound (C1), can be preferably used as an additive for a resist composition for immersion exposure.

The compound (C1-1) can be used as a monomer for producing a fluorine-containing compound (C2) described below.

[Fluorine-Containing Compound (C2)]

As the fluorine-containing compound (C2), a polymeric compound having a structural unit derived from a fluorine-containing compound (C1) in which $R^1$ represents an organic group containing a polymerizable group can be preferably used.

Specifically, a polymeric compound having a structural unit represented by general formula (c-1-3) or (c-1-4) shown below (hereafter, this structural unit is referred to as "structural unit (c1)") can be preferably used.

[Chemical Formula 46.]

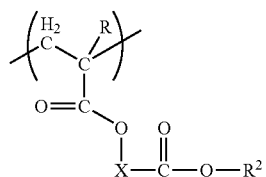
(c-1-3)

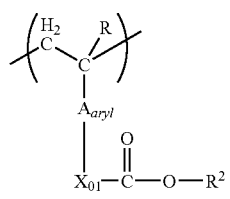
(c-1-4)

wherein each R independently represents a hydrogen atom, a lower alkyl group or a halogenated lower alkyl group; X represents a divalent organic group having no acid dissociable portion; $A_{aryl}$ represents an aromatic cyclic group which may have a substituent; $X_{01}$ represents a single bond or a divalent linkage group; and each $R^2$ independently represents an organic group having a fluorine atom.

In general formulas (c-1-3) and (c-1-4), $A_{aryl}$, R, $R^2$, X and $X_{01}$ are respectively as defined for $A_{aryl}$, R, $R^2$, X and $X_{01}$ in general formulas (c-1-1) and (c-1-2) above.

As the structural unit (c1), any one of the structural units represented by general formulas (c-1-31) to (c-1-35) and (c-1-41) to (c-1-44) can be preferably used.

[Chemical Formula 47.]

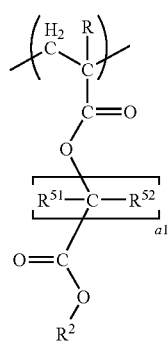
(c-1-31)

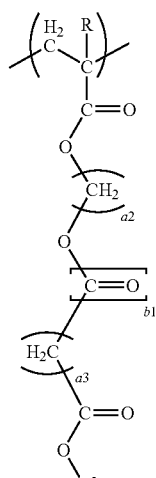
(c-1-32)

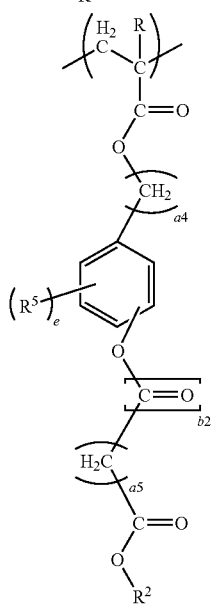
(c-1-33)

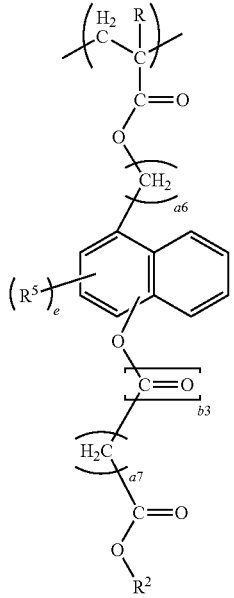
(c-1-34)

(c-1-35)

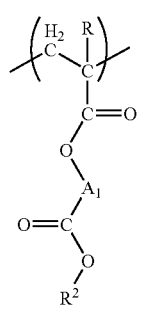

[Chemical Formula 48.]

(c-1-41)

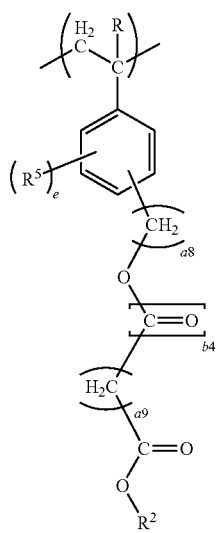

(c-1-42)

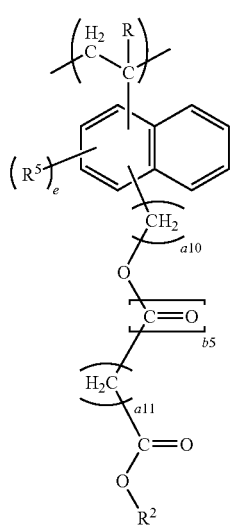

(c-1-43)

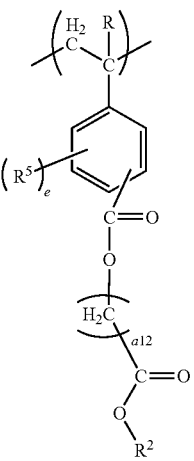

(c-1-44)

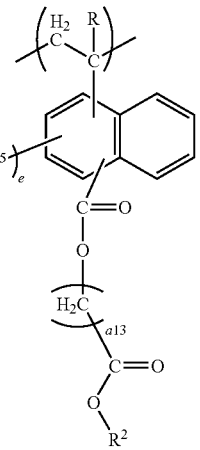

In general formulas (c-1-31) to (c-1-35), R, $R^2$, $R^{51}$, $R^{52}$, a1 to a7, b1 to b3, $R^5$, e and $A_1$ are respectively as defined for R, $R^2$, $R^{51}$, $R^{52}$, a1 to a7, b1 to b3, $R^5$, e and $A_1$ described above in the explanation of the fluorine-containing compound (C1).

In general formulas (c-1-41) to (c-1-44), R, $R^2$, a8 to a13, b4, b5, $R^5$ and e are respectively as defined for R, $R^2$, a8 to a13, b4, b5, $R^5$ and e described above in the explanation of the fluorine-containing compound (C1).

Specific examples of structural units represented by general formulas (c-1-31) to (c-1-35) and (c-1-41) to (c-1-44) are shown below.

[Chemical Formula 49.]
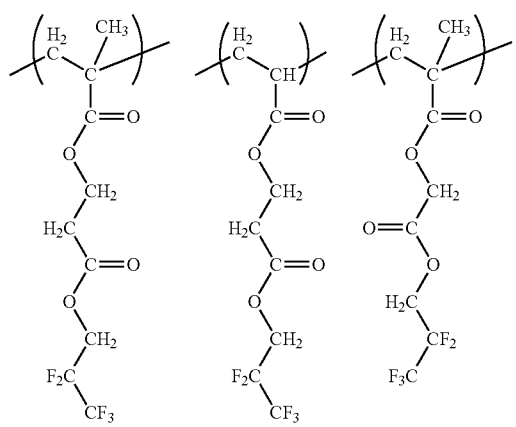
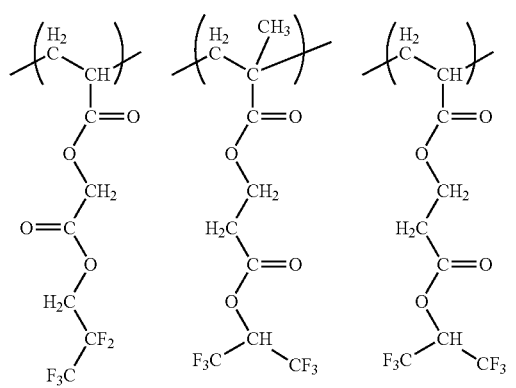
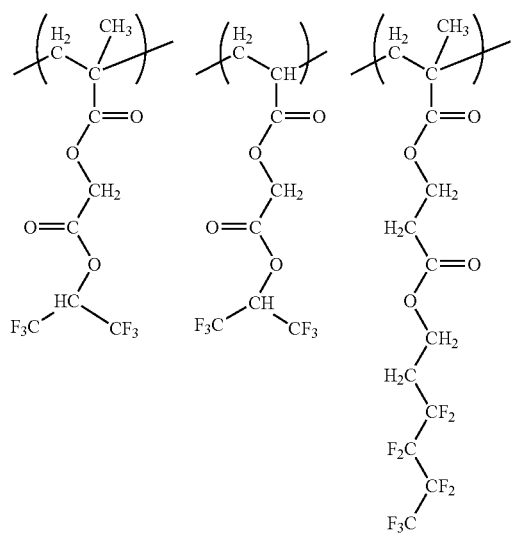
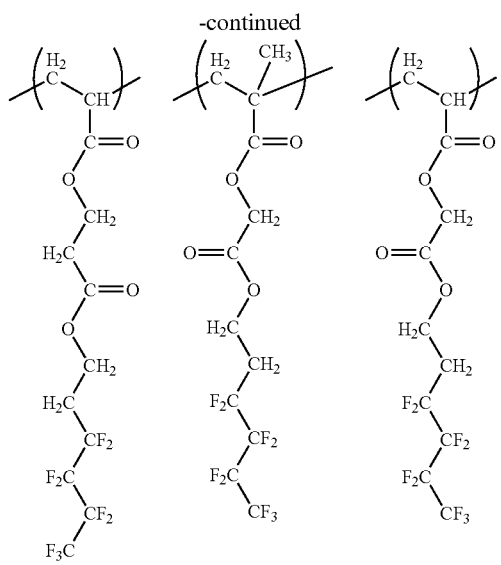
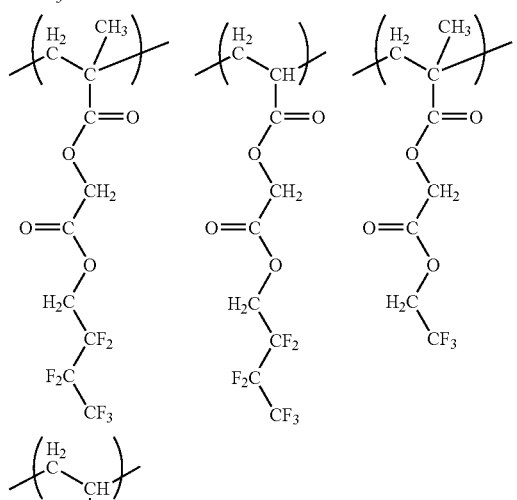
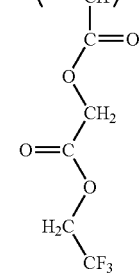
[Chemical Formula 50.]
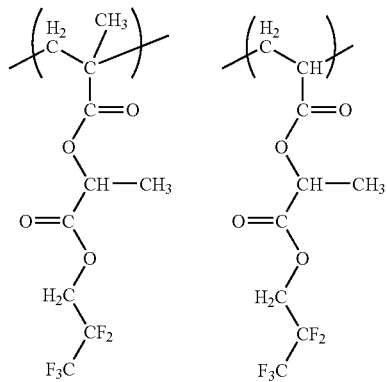

93
-continued
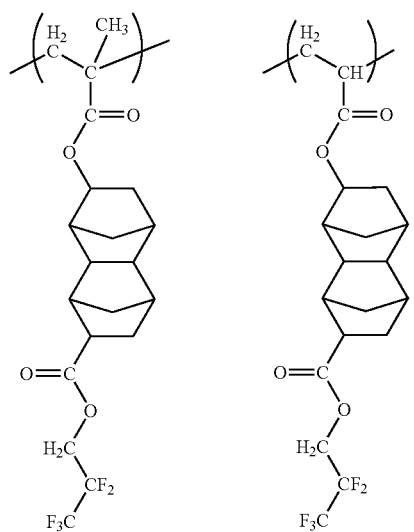
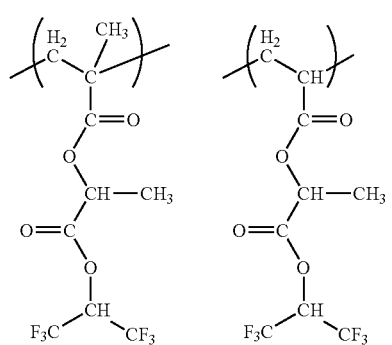
[Chemical Formula 51.]
94
-continued
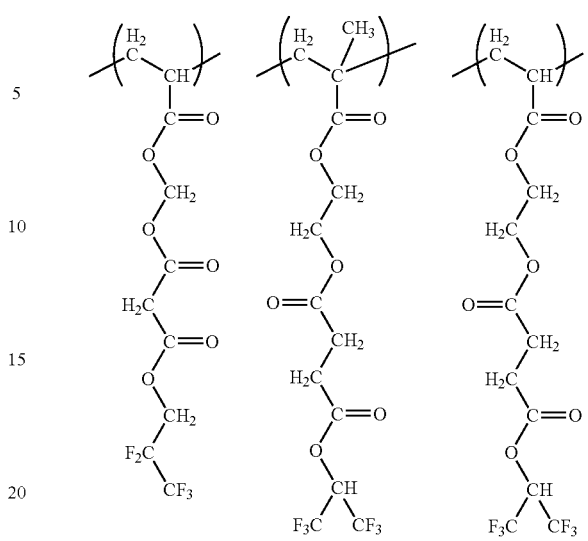
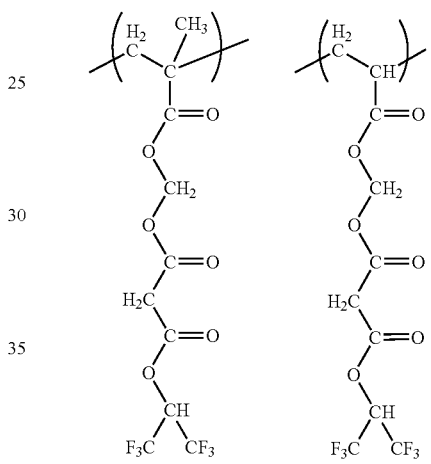
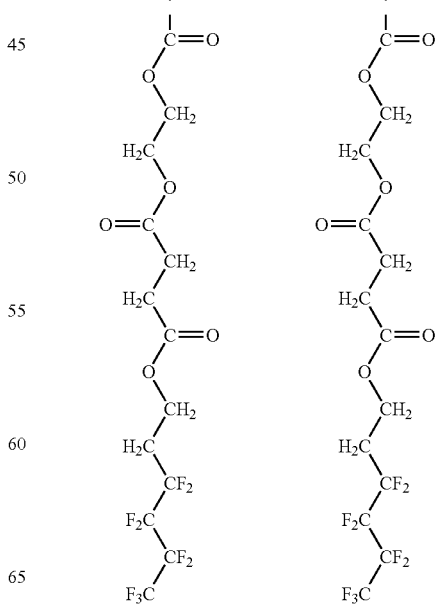

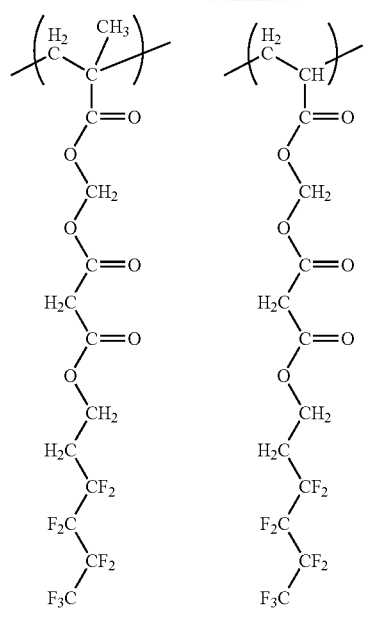
[Chemical Formula 52.]
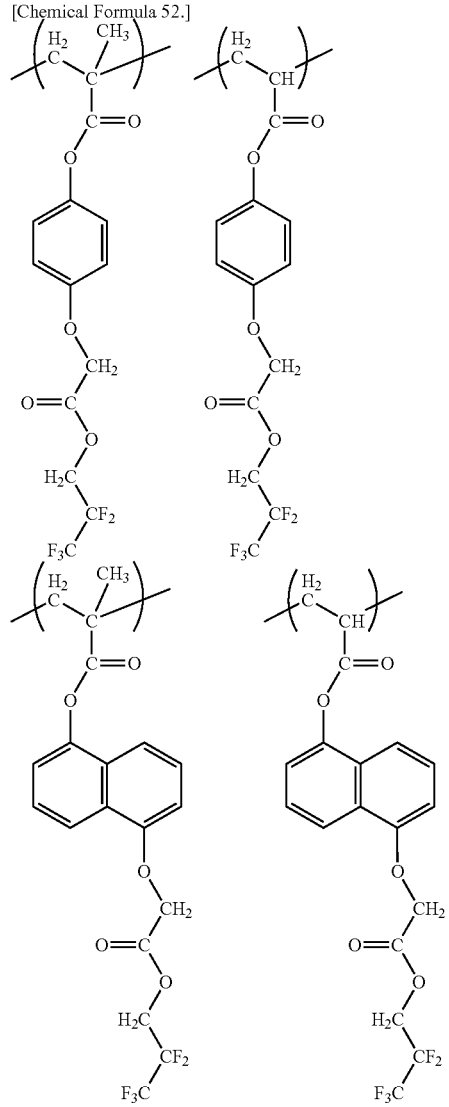
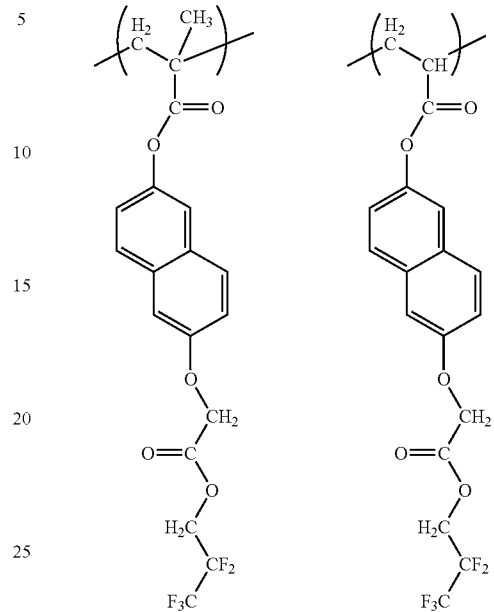
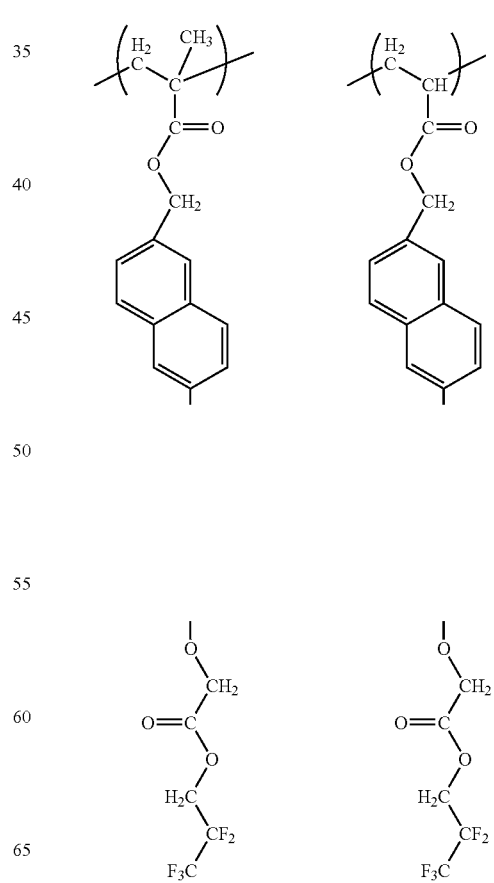

-continued
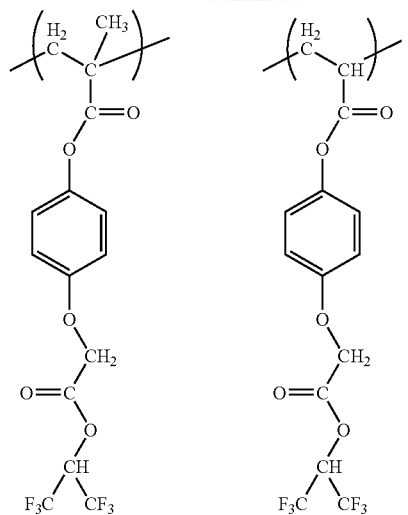
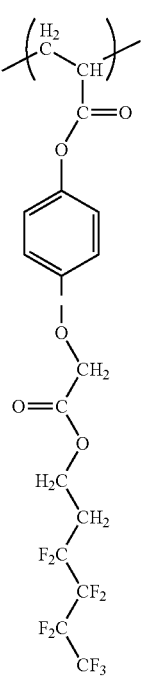
[Chemical Formula 53.]
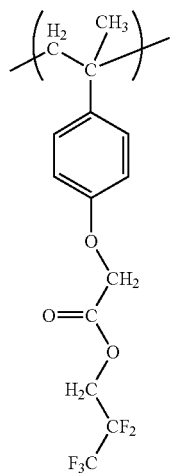 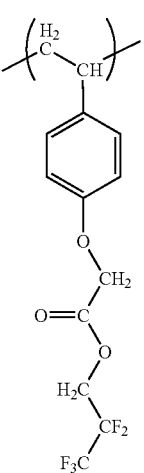
-continued
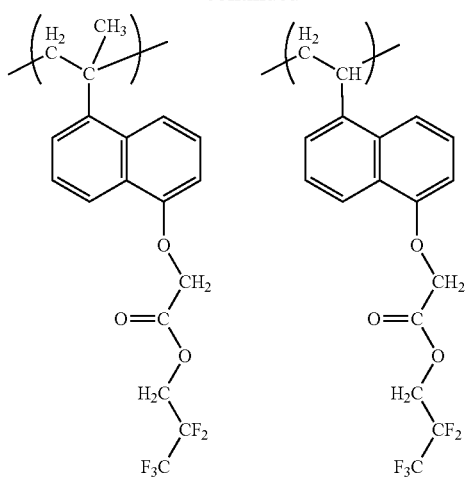
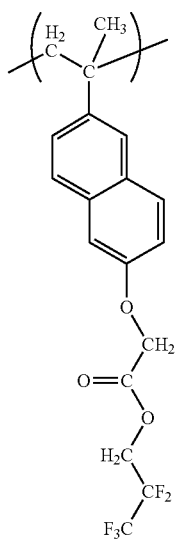
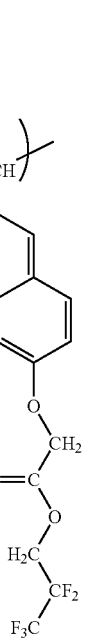
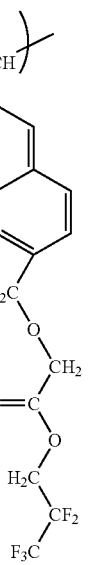

-continued

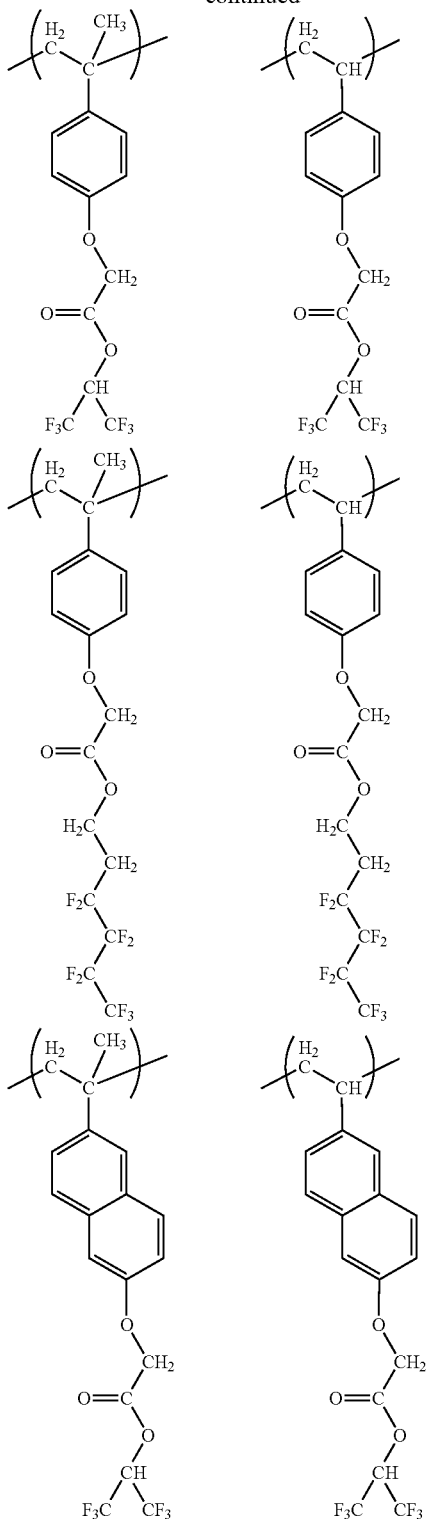

As the structural unit (c1), at least one structural unit selected from the group consisting of structural units represented by general formulas (c-1-31) to (c-1-35) and (c-1-41) to (c-1-44) is preferable, more preferably at least one structural unit selected from the group consisting of structural units represented by general formulas (c-1-31) to (c-1-35), (c-1-41) and (c-1-42), and most preferably at least one structural unit selected from the group consisting of structural units represented by general formulas (c-1-31), (c-1-35) and (c-1-42).

In the fluorine-containing compound (C2), as the structural unit (c1), one type of structural unit may be used, or two or more types may be used in combination.

In the fluorine-containing compound (C2), the amount of the structural unit (c1) based on the combined total of all structural units constituting the fluorine-containing compound (C2) is preferably 10 to 100 mol %, more preferably 30 to 100 mol %, still more preferably 40 to 100 mol %, still more preferably 50 to 100 mol %, and may be even 100 mol %. When the amount of the structural unit (c1) is at least as large as the lower limit of the above-mentioned range, the characteristic feature of exhibiting hydrophobicity during immersion exposure, and becoming hydrophilic during alkali developing is improved.

The fluorine-containing compound (C2) may also include a structural unit other than the structural unit (c1), as long as the effects of the present invention are not impaired.

Such a structural unit is not particularly limited, but a structural unit derived from a compound copolymerizable with the compound from which the structural unit is derived (e.g., the aforementioned compound (C1-1) or a precursor thereof) is preferable. Examples of such structural units include the aforementioned structural units (a1) to (a4) which the resin component (A1) may have, a structural unit derived from hydroxystyrene, a structural unit derived from styrene, and a structural unit containing a carboxy group.

As a precursor of the compound (C1-1), for example, a compound in which —O—$R^2$ within the compound (C1-1) has been replaced with —O—H (i.e., a carboxylic acid compound) can be used.

As the structural unit other than the structural unit (c1) which the fluorine-containing compound (C2) may have, a structural unit containing an acid dissociable group (hereafter, referred to as "structural unit (c2)") and/or a structural unit containing a carboxy group (hereafter, referred to as "structural unit (c3)") is preferable.

Structural Unit (c2):

In the fluorine-containing compound (C2), the structural unit (c2) refers to a structural unit containing an acid dissociable group.

In the present description and claims, an "acid dissociable group" is an organic group which is dissociable by action of acid.

The acid dissociable group within the structural unit (c2) is not particularly limited, as long as it is an organic group which is dissociable by action of acid. For example, any of the groups that have been proposed as acid dissociable, dissolution inhibiting groups for the base resins of chemically amplified resists can be used. Specific examples include the same acid dissociable, dissolution inhibiting groups as those described above for the structural unit (a1). The structure of the main chain of the structural unit (a2) is not particularly limited. For example, a structural unit derived from styrene or a structural unit derived from (meth)acrylic acid can be used.

In the fluorine-containing compound (C2), the structural unit (c2) is preferably a structural unit represented by general formula (c2-1) shown below.

[Chemical Formula 54.]

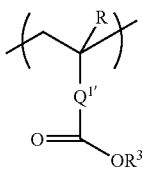

(c2-1)

wherein R represents a hydrogen atom, a lower alkyl group or a halogenated lower alkyl group; $Q^{1'}$ represents a single bond or a divalent linkage group; and $R^3$ represents an acid dissociable group.

In general formula (c2-1) above, R represents a hydrogen atom, a lower alkyl group or a halogenated lower alkyl group. As the lower alkyl group and halogenated lower alkyl group for R, the same groups as those for R above can be used.

In general formula (c2-1) above, $Q^{1'}$ represents a single bond or a divalent linkage group. As the divalent linkage group for $Q^{1'}$, the same groups as those for $X_{01}$ in general formula (c-1-4) above or divalent aromatic hydrocarbon groups can be used. Examples of divalent aromatic hydrocarbon groups include aromatic hydrocarbon groups of 6 to 20 carbon atoms, such as groups in which two hydrogen atoms have been removed from benzene, naphthalene or anthracene.

In the structural unit (c2), $Q^{1'}$ is preferably a single bond or a group represented by the formula —C(=O)—O—$R^c$— (wherein $R^c$ represents a linear or branched alkylene group of 1 to 10 carbon atoms which may contain an oxygen atom, and the alkylene group may be fluorinated), and more preferably a single bond.

In general formula (c2-1) above, $R^3$ represents an acid dissociable group.

As the acid dissociable group for $R^3$, there is no particular limitation as long as it is an organic group which is dissociable by action of acid. Examples of acid dissociable groups include a cyclic or chain-like tertiary alkyl ester-type acid dissociable group and an acetal-type acid dissociable group such as an alkoxyalkyl group. Among these, as $R^3$, a tertiary alkyl ester-type acid dissociable group is preferable, and a group represented by general formula (IV-1) shown below is more preferable.

[Chemical Formula 55.]

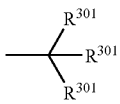

(IV-1)

wherein at least one $R^{301}$ represents a linear or branched alkyl group of 1 to 4 carbon atoms, and the or each remaining $R^{301}$ independently represents a linear or branched alkyl group of 1 to 4 carbon atoms or a monovalent aliphatic cyclic group of 4 to 20 carbon atoms, or the remaining two $R^{301}$ may be mutually bonded to form a divalent aliphatic cyclic group of 4 to 20 carbon atoms together with the carbon atom to which the two $R^{301}$ are bonded; wherein the plurality of $R^{301}$ may be the same or different.

As the aliphatic cyclic group, for example, a group in which one or more hydrogen atoms have been removed from a monocycloalkane or a polycycloalkane such as a bicycloalkane, tricycloalkane or tetracycloalkane can be used. Examples of such groups include groups in which one or more hydrogen atoms have been removed from a monocycloalkane such as cyclopentane, cyclohexane, cycloheptane, cyclooctane or cyclodecane; and groups in which one or more hydrogen atoms have been removed from a polycycloalkane such as adamantane, norbornane, isobornane, tricyclodecane or tetracyclododecane. Specific examples of such groups include a cyclopentyl group, a cyclohexyl group, a norbornyl group and an adamantyl group.

Examples of linear or branched alkyl groups of 1 to 4 carbon atoms include a methyl group, an ethyl group, a propyl group, an isopropyl group, an n-butyl group, an isobutyl group and a tert-butyl group.

Examples of acid dissociable groups represented by general formula (IV-1) above in which the plurality of $R^{301}$ independently represents a linear or branched alkyl group of 1 to 4 carbon atoms include a tert-butyl group, a tert-pentyl group and a tert-hexyl group.

Examples of acid dissociable groups represented by general formula (IV-1) above in which at least one $R^{301}$ represents a linear or branched alkyl group of 1 to 4 carbon atoms, and the or each remaining $R^{301}$ independently represents a linear or branched alkyl group of 1 to 4 carbon atoms or a monovalent aliphatic cyclic group of 4 to 20 carbon atoms include a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group and a 1-(1-cyclohexyl)-1-methylpentyl group.

Examples of acid dissociable groups represented by general formula (IV-1) above in which one $R^{301}$ represents a linear or branched alkyl group of 1 to 4 carbon atoms, and the remaining two $R^{301}$ are mutually bonded to form a divalent aliphatic cyclic group of 4 to 20 carbon atoms together with the carbon atom to which the two $R^{301}$ are bonded include a 2-alkyl-2-adamantyl group such as a 2-methyl-2-adamantyl group, a 2-ethyl-2-adamantyl group or a 2-propyl-2-adamantyl group; and a 1-alkyl-1-cycloalkyl group such as a 1-methyl-1-cyclopentyl group, a 1-ethyl-1-cyclopentyl group, a 1-methyl-1-cyclohexyl group, a 1-ethyl-1-cyclohexyl group, a 1-methyl-1-cyclooctyl group or a 1-ethyl-1-cyclooctyl group.

Among the above-mentioned examples, as an acid dissociable group represented by general formula (IV-1) above, a group in which one $R^{301}$ represents a linear or branched alkyl group of 1 to 4 carbon atoms, and the remaining two $R^{301}$ are mutually bonded to form a divalent aliphatic cyclic group of 4 to 20 carbon atoms together with the carbon atom to which the two $R^{301}$ are bonded is preferable, and a 2-methyl-2-adamantyl group or a 2-isopropyl-2-adamantyl group is particularly desirable.

$R^{301}$ may have a substituent, as long as the group represented by general formula (IV-1) functions as an acid dissociable group. An example of the substituent includes a halogen atom such as a fluorine atom.

Preferable examples of structural units in which $Q^{1'}$ in general formula (c2-1) represents a single bond include structural units represented by general formulas (c2-1-1) to (c2-1-14) shown below.

Preferable examples of structural units in which $Q^{1'}$ in general formula (c2-1) represents —C(=O)—O—$R^c$— include structural units represented by general formulas (c2-1-15) to (c2-1-28) shown below. In the general formulas shown below, R is as defined above, and is preferably a hydrogen atom or a methyl group.
[Chemical Formula 56.]
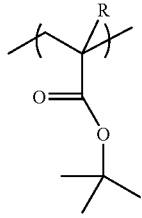
(c2-1-1)
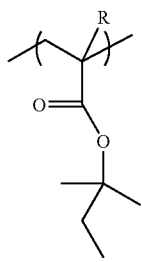
(c2-1-2)
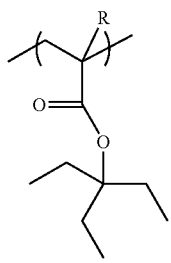
(c2-1-3)
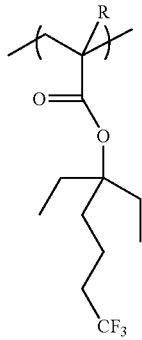
(c2-1-4)
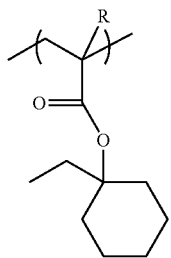
(c2-1-5)
-continued
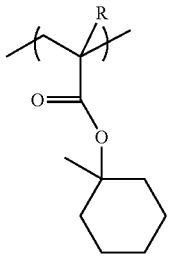
(c2-1-6)
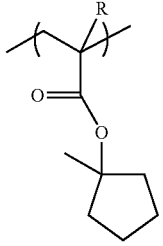
(c2-1-7)
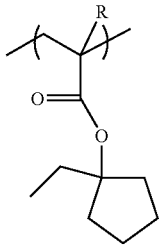
(c2-1-8)
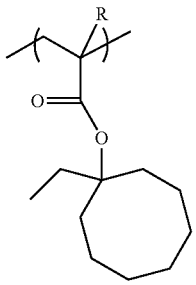
(c2-1-9)
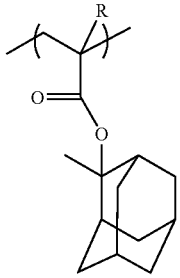
(c2-1-10)
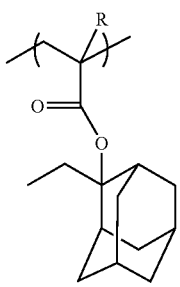
(c2-1-11)

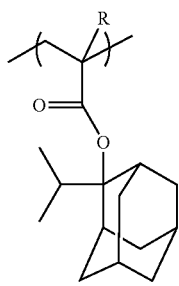 (c2-1-12)
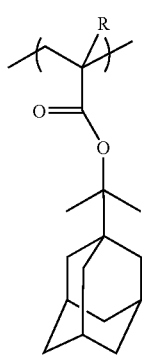 (c2-1-13)
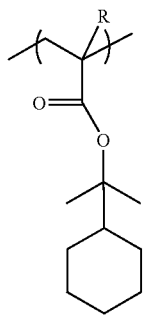 (c2-1-14)
[Chemical Formula 57.]
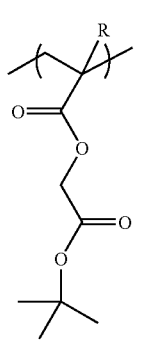 (c2-1-15)
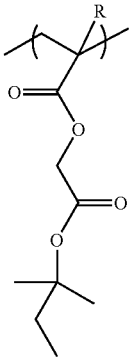 (c2-1-16)
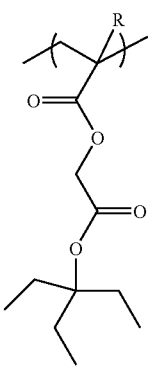 (c2-1-17)
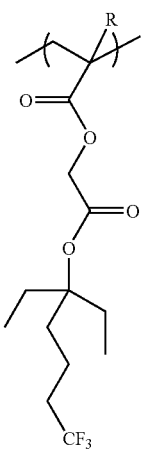 (c2-1-18)
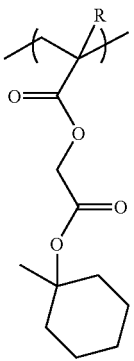 (c2-1-19)

-continued
(c2-1-20)
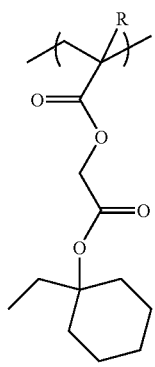
(c2-1-21)
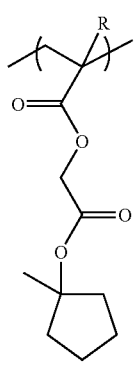
(c2-1-22)
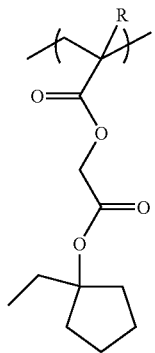
(c2-1-23)
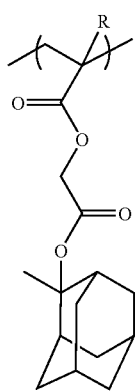
-continued
[Chemical Formula 58.]
(c2-1-24)
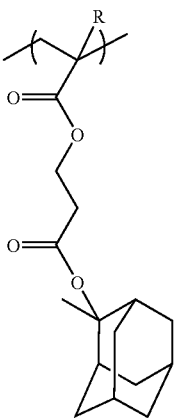
(c2-1-25)
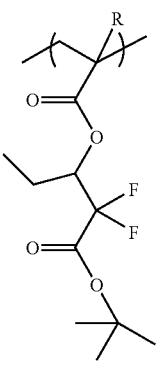
(c2-1-26)
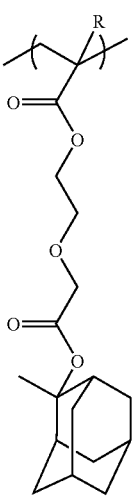

-continued (c2-1-27)

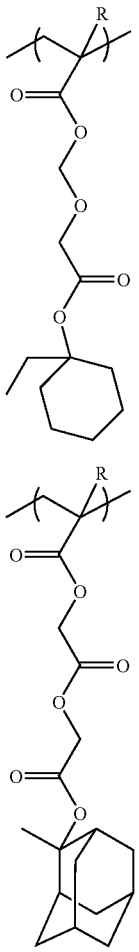

(c2-1-28)

As the structural unit (c2), at least one structural unit selected from the group consisting of structural units represented by general formulas (c2-1-1) to (c2-1-28) is preferable, at least one structural unit selected from the group consisting of general formulas (c2-1-1) to (c2-1-14) and (c2-1-25) is more preferable, and at least one structural unit selected from the group consisting of structural units represented by general formulas (c2-1-1) to (c2-1-3), (c2-1-9), (c2-1-12) and (c2-1-25) is particularly desirable.

In the fluorine-containing compound (C2), as the structural unit (c2), one type of structural unit may be used, or two or more types may be used in combination.

In the fluorine-containing compound (C2), the amount of the structural unit (c2) is preferably smaller than the amount of the structural unit (c1). For example, the amount of the structural unit (c2) based on the combined total of all structural units constituting the fluorine-containing compound (C2) is preferably 1 to less than 80 mol %, more preferably 5 to 70 mol %, and still more preferably 10 to 60 mol %.

When the fluorine-containing compound (C2) is a copolymer, the amount of the structural unit (c1) within fluorine-containing compound (C2), based on the combined total of all structural units constituting the fluorine-containing compound (C2) is preferably 10 to 90 mol %, more preferably 20 to 90 mol %, still more preferably 30 to 80 mol %, and most preferably 40 to 70 mol %.

Structural Unit (c3):

In the fluorine-containing compound (C2), the structural unit (c3) refers to a structural unit containing a carboxy group.

As the structural unit (c3), a structural unit represented by general formula (c3-1), (c3-2) or (c3-3) shown below can be preferably used.

[Chemical Formula 59.]

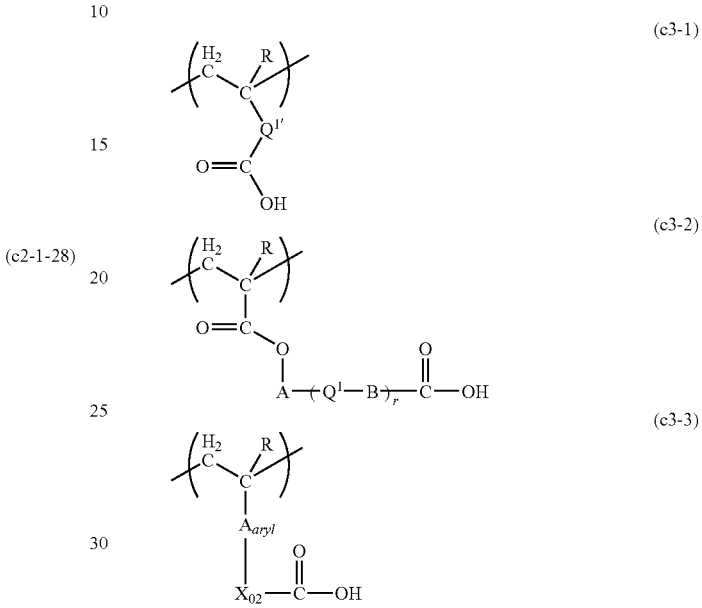

wherein each R independently represents a hydrogen atom, a lower alkyl group or a halogenated lower alkyl group; $Q^{1'}$ represents a single bond or a divalent linkage group; each of A and B independently represents a divalent hydrocarbon group which may have a substituent; $Q^1$ represents a divalent linkage group containing an oxygen atom; r represents 0 or 1; $A_{aryl}$ represents an aromatic cyclic group which may have a substituent; and $X_{02}$ represents a single bond, $-(R^7)_{a0}-O-[C(=O)]_{b0}-R^8-$ or $-C(=O)-O-R^9-$.

In general formula (c3-1) above, R and $Q^{1'}$ are respectively as defined for R and $Q^{1'}$ in general formula (c2-1) above.

In general formula (c3-2) above, R, A, B, $Q^1$ and r are respectively as defined for R, A, B, $Q^1$ and r in general formula (c-1-10) above.

In general formula (c3-3) above, R, $A_{aryl}$ and $X_{02}$ are respectively as defined for R, $A_{aryl}$ and $X_{02}$ in general formula (c-1-11) above.

Specific examples of structural units represented by general formulas (c3-1) to (c3-3) are shown below.

In the general formulas shown below, R is as defined above, and is preferably a hydrogen atom or a methyl group.

[Chemical Formula 60.]

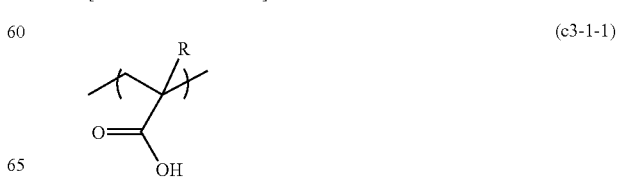

(c3-1-1)

[Chemical Formula 61.]
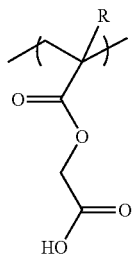 (c3-2-1)
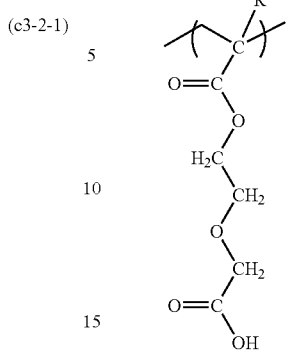 (c3-2-5)
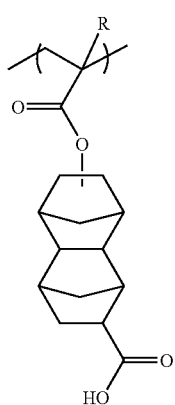 (c3-2-2)
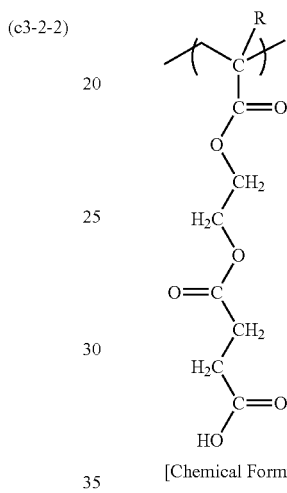 (c3-2-6)
[Chemical Formula 62.]
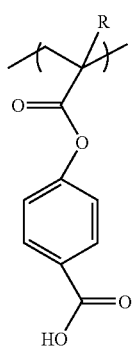 (c3-2-3)
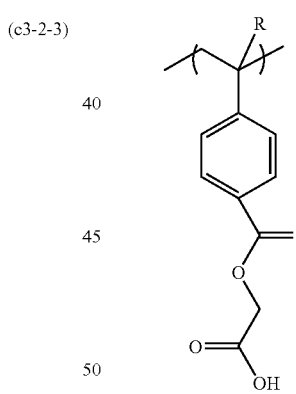 (c3-3-1)
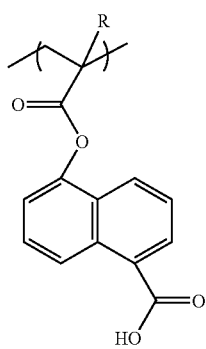 (c3-2-4)
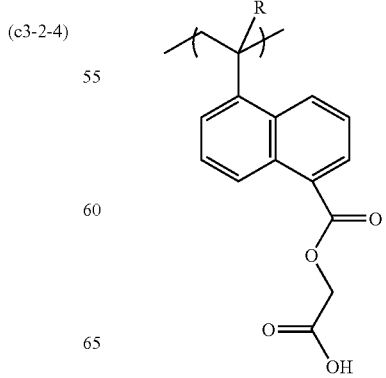 (c3-3-2)

-continued (c3-3-3)

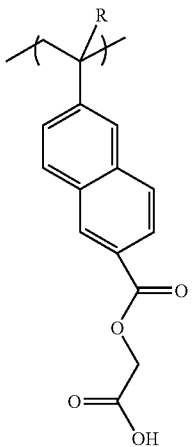

As the structural unit (c3), at least one structural unit selected from the group consisting of structural units represented by general formulas (c3-1), (c3-2) and (c3-3) is preferable, and a structural unit represented by general formula (c3-1) is particularly desirable.

More specifically, as the structural unit (c3), at least one structural unit selected from the group consisting of structural units represented by general formulas (c3-1-1), (c3-2-1) to (c3-2-6) and (c3-3-1) to (c3-3-3) is preferable, and a structural unit represented by general formula (c3-1-1) is particularly desirable.

In the fluorine-containing compound (C2), as the structural unit (c3), one type of structural unit may be used, or two or more types may be used in combination.

In the fluorine-containing compound (C2), the amount of the structural unit (c3) based on the combined total of all structural units constituting the fluorine-containing compound (C2) is preferably 1 to 25 mol %, more preferably 5 to 20 mol %, and most preferably 10 to 20 mol %.

In the present invention, the fluorine-containing compound (C2) is preferably a polymer including the structural unit (c1).

Examples of such polymers include a polymer consisting of the structural unit (c1); a copolymer consisting of the structural units (c1) and (c2); and a copolymer consisting of the structural units (c1), (c2) and (c3).

The weight average molecular weight (Mw) (the polystyrene equivalent value determined by gel permeation chromatography) of the fluorine-containing compound (C2) is not particularly limited, but is preferably 2,000 to 100,000, more preferably 3,000 to 100,000, still more preferably 4,000 to 50,000, and most preferably 5,000 to 50,000. By making the weight average molecular weight no more than the upper limit of the above-mentioned range, the fluorine-containing compound (C2) exhibits satisfactory solubility in a resist solvent when used for a resist. On the other hand, by making the weight average molecular weight at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

The fluorine-containing compound (C2) described hereinabove can be preferably used as an additive for a resist composition for immersion exposure.

As the component (C), any one of the fluorine-containing compounds described above can be used alone, or two or more of the fluorine-containing compounds can be used in combination.

In the resist composition for immersion exposure according to the present invention, as the component (C), it is preferable to use the fluorine-containing compound (C1) and/or the fluorine-containing compound (C2), more preferably the fluorine-containing compound (C2), and it is particularly desirable to use a polymeric compound including a structural unit represented by general formula (c-1-3) or (c-1-4) above (structural unit (c1)).

In the resist composition for immersion exposure according to the present invention, the amount of the component (C) relative to 100 parts by weight of the component (A) is preferably 0.1 to 50 parts by weight, more preferably 0.1 to 40 parts by weight, still more preferably 0.5 to 30 parts by weight, and most preferably 1 to 15 parts by weight. By making the amount of the component (C) at least as large as the lower limit of the above-mentioned range, the hydrophobicity of a resist film formed using the resist composition for immersion exposure is enhanced, which is preferable in immersion exposure. Further, improvement in hydrophilicity of the resist film when the resist film comes in contact with an alkali developing solution becomes significant. On the other hand, by making the amount of the component (C) no more than the upper limit of the above-mentioned range, the lithography properties of the resist composition are improved.

[Production Method of Fluorine-Containing Compound (C)]

The fluorine-containing compound (C) according to the present invention can be produced, for example, by introducing a group $R^2$ into the —O—H group within a compound represented by the formula $R^1$—C(=O)—O—H (substituting the hydrogen atom of the —O—H group with $R^2$).

The introduction of the group $R^2$ can be performed by a conventional method. For example, a method in which a compound (I) represented by general formula (I) shown below is reacted with a compound (II) represented by general formula (II) shown below can be used.

[Chemical Formula 63.]

(I)

(II)

wherein $R^1$ and $R^2$ are as defined above.

The method of reacting the compound (I) with the compound (II) is not particularly limited. For example, a method in which the compound (I) comes in contact with the compound (II) in a reaction solvent in the presence of a base can be used.

As the compound (I) and the compound (II), commercially available compounds can be used. Alternatively, the compound (I) and the compound (II) can be synthesized.

As the compound (I), for example, a low molecular weight compound derived from an acrylate ester such as a carboxyalkyl(meth)acrylate or a mono((meth)acryloyloxyalkyl)succinate, or a polymeric compound including a structural unit derived from an acrylate ester can be used.

As the compound (II), for example, a fluorinated alkylalcohol or the like can be used.

As the reaction solvent, any solvent capable of dissolving the compound (I) and the compound (II) (which are raw materials) can be used. Specific examples include tetrahydrofuran (THF), acetone, dimethylformamide (DMF), dimethylacetamide, dimethylsulfoxide (DMSO) and acetonitrile.

Examples of the base include organic bases such as triethylamine, 4-dimethylaminopyridine (DMAP) and pyridine; and inorganic bases such as sodium hydride, $K_2CO_3$ and $Cs_2CO_3$.

Examples of the condensing agent include carbodiimide reagents such as ethyldiisopropylaminocarbodiimide hydrochloride (EDCl), dicyclohexylcarboxyimide (DCC), diisopropylcarbodiimide and carbodiimidazole; tetraethyl pyrophosphate; and benzotriazole-N-hydroxytrisdimethylaminophosphonium hexafluorophosphide (Bop reagent).

If desired, an acid may be used. As the acid, any acid generally used for dehydration/condensation may be used. Specific examples include inorganic acids such as hydrochloric acid, sulfuric acid and phosphoric acid; and organic acids such as methanesulfonic acid, trifluoromethanesulfonic acid, benzenesulfonic acid and p-toluenesulfonic acid. These acids may be used alone, or in a combination of two or more.

The amount of the compound (II) added is preferably 1 to 3 times the molar amount of the compound (I), more preferably 1 to 2 times the molar amount of the compound (I).

The reaction temperature is preferably −20 to 40° C., more preferably 0 to 30° C.

The reaction time varies, depending on the reactivity of the compound (I) and the compound (II), the reaction temperature, and the like. However, in general, the reaction time is preferably 30 to 480 minutes, more preferably 60 to 360 minutes.

Further, when the component (C) is a polymeric compound (e.g., the fluorine-containing compound (C2)), the component (C) can be obtained, for example, by a conventional radical polymerization or the like of the monomers corresponding with each of the desired structural units (e.g., the aforementioned compound (C1-1)), using a radical polymerization initiator such as azobisisobutyronitrile (AIBN) or dimethyl 2,2'-azobis(isobutyrate).

<Optional Component>

In the resist composition for immersion exposure according to the present invention, for improving the resist pattern shape and the post exposure stability of the latent image formed by the pattern-wise exposure of the resist layer, it is preferable to add a nitrogen-containing organic compound (D) (hereafter referred to as the component (D)) as an optional component.

A multitude of these components (D) have already been proposed, and any of these known compounds may be used, although a cyclic amine, an aliphatic amine, and particularly a secondary aliphatic amine or tertiary aliphatic amine is preferable. An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine is more preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

As the component (D), one type of acid generator may be used, or two or more types may be used in combination.

In the present invention, as the component (D), it is preferable to use an alkylamine, and it is particularly desirable to use tri-n-pentylamine.

The component (D) is typically used in an amount within a range from 0.01 to 5.0 parts by weight, relative to 100 parts by weight of the component (A).

Furthermore, in the resist composition for immersion exposure according to the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

In the present invention, as the component (E), it is preferable to use an organic carboxylic acid, and it is particularly desirable to use salicylic acid.

The component (E) is typically used in an amount within a range from 0.01 to 5.0 parts by weight, relative to 100 parts by weight of the component (A).

If desired, other miscible additives can also be added to the positive resist composition for immersion exposure according to the present invention. Examples of such miscible additives include additive resins for improving the performance of the resist film, surfactants for improving the applicability, dissolution inhibitors, plasticizers, stabilizers, colorants, halation prevention agents, and dyes.

<Organic Solvent (S)>

The resist composition for immersion exposure according to the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME), ethyl lactate (EL) and γ-butyrolactone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 5 to 15% by weight.

Dissolving of the materials for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, a membrane filter or the like.

<<Method of Forming a Resist Pattern>>

The method of forming a resist pattern according to the present invention includes: applying a resist composition for immersion exposure according to the first aspect of the present invention to a substrate to form a resist film on the substrate; subjecting the resist film to immersion exposure; and alkali developing the resist film to form a resist pattern.

A preferable example of the method for forming a resist pattern according to the second aspect of the present invention will be described below.

Firstly, a resist composition for immersion exposure according to the present invention is applied onto a substrate using a spinner or the like, and a prebake (post applied bake (PAB)) is conducted to form a resist film.

The substrate is not specifically limited and a conventionally known substrate can be used. For example, substrates for electronic components, and such substrates having wiring patterns formed thereon can be exemplified. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-exemplified substrates provided with an inorganic and/or organic film on the surface thereof may be used. As the inorganic film, an inorganic antireflection film (inorganic BARC) can be exemplified. As the organic film, an organic antireflection film (organic BARC) and an organic film such as a lower-layer organic film used in a multilayer resist method can be exemplified.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film.

After formation of a resist film, an organic antireflection film may be provided on the resist film, thereby forming a triple layer laminate consisting of the substrate, the resist film and the antireflection film. The anti-reflection film provided on top of the resist film is preferably soluble in an alkali developing solution.

The steps up until this point can be conducted by using conventional techniques. The operating conditions and the like are appropriately selected depending on the formulation and the characteristics of the resist composition for immersion exposure being used.

Subsequently, the obtained resist film is subjected to selective immersion exposure (liquid immersion lithography) through a desired mask pattern. At this time, the region between the resist film and the lens at the lowermost point of the exposure apparatus is pre-filled with a solvent (immersion medium) that has a larger refractive index than the refractive index of air, and the exposure (immersion exposure) is conducted in this state.

There are no particular limitations on the wavelength used for the exposure, and an ArF excimer laser, KrF excimer laser or $F_2$ excimer laser or the like can be used. The resist composition according to the present invention is effective for KrF or ArF excimer lasers, and is particularly effective for ArF excimer lasers.

The immersion medium preferably exhibits a refractive index larger than the refractive index of air but smaller than the refractive index of the resist film formed from the resist composition for immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

A resist composition for immersion exposure according to the present invention is particularly resistant to any adverse effects caused by water, and because the resulting lithography properties such as sensitivity and shape of the resist pattern are excellent, water is preferably used as the immersion medium which exhibits a refractive index that is larger than the refractive index of air. Furthermore, water is also preferred in terms of cost, safety, environmental friendliness, and versatility.

Subsequently, following completion of the immersion exposure step, post exposure baking (PEB) is conducted, followed by a developing treatment using an alkali developing solution containing an alkali aqueous solution. Thereafter, water rinse is preferably conducted with pure water. This water rinse can be conducted by dripping or spraying water onto the surface of the substrate while rotating the substrate, and washes away the developing solution and those portions of the resist composition for immersion exposure that have been dissolved by the developing solution. Further, by drying, a resist pattern is obtained in which the resist film (coating of the resist composition for immersion exposure) has been patterned into a shape corresponding to the mask pattern.

<<Fluorine-Containing Compound>>

The fluorine-containing compound of the present invention is a compound represented by general formula (c-1) shown below, and is the same as the component (C) described above in connection with the resist composition for immersion exposure according to the first aspect of the present invention.

[Chemical Formula 64.]

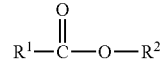

(c-1)

wherein $R^1$ represents an organic group which may contain a polymerizable group, with the proviso that said polymerizable group has a carbon-carbon multiple bond, and the carbon atoms forming the multiple bond are not directly bonded to the carbon atom within the —C(=O)— group in general formula (c-1); and $R^2$ represents an organic group having a fluorine atom.

In general formula (c-1) above, $R^1$ and $R^2$ are respectively as defined for $R^1$ and $R^2$ described above in connection with the component (C).

As the fluorine-containing compound represented by general formula (c-1) above, a compound represented by general formula (c-1-1) or (c-1-2) shown below is preferable.

Further, as the fluorine-containing compound represented by general formula (c-1) above, a polymeric compound including a structural unit represented by general formula (c-1-3) or (c-1-4) shown below is also preferable.

[Chemical Formula 65.]

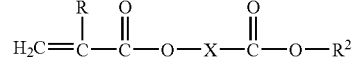

(c-1-1)

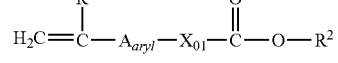

(c-1-2)

wherein each R independently represents a hydrogen atom, a lower alkyl group or a halogenated lower alkyl group; X represents a divalent organic group having no acid dissociable portion; $A_{aryl}$ represents an aromatic cyclic group which may have a substituent; $X_{01}$ represents a single bond or a divalent linkage group; and each $R^2$ independently represents an organic group having a fluorine atom.

[Chemical Formula 66.]

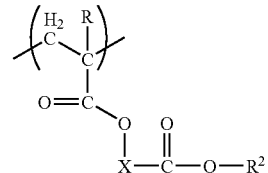

(c-1-3)

-continued

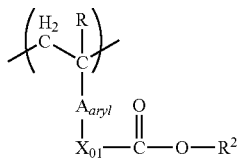
(c-1-4)

wherein each R independently represents a hydrogen atom, a lower alkyl group or a halogenated lower alkyl group; X represents a divalent organic group having no acid dissociable portion; $A_{aryl}$ represents an aromatic cyclic group which may have a substituent; $X_{01}$ represents a single bond or a divalent linkage group; and each $R^2$ independently represents an organic group having a fluorine atom.

In general formulas (c-1-1) to (c-1-4), R, $R^2$, $A_{aryl}$, X and $X_{01}$ are respectively as defined for R, $R^2$, $A_{aryl}$, X and $X_{01}$ described above in connection with the component (C).

The aforementioned fluorine-containing compound according to the third aspect of the present invention is a novel compound which was essentially unknown.

The fluorine-containing compound is useful as an additive for a resist composition, and such a resist composition having the fluorine-containing compound added thereto is preferable for immersion exposure.

As the resist composition to which the fluorine-containing compound is added, there is no particular limitation, and it is preferable to use a chemically amplified resist composition including a base component that exhibits changed solubility in an alkali developing solution under action of acid, and an acid generator component that generates acid upon exposure.

Especially, the fluorine-containing compound is useful as an additive for the resist composition for immersion exposure according to the present invention.

The resist composition for immersion exposure according to the first aspect of the present invention exhibits excellent lithography properties and other properties favorable for immersion exposure (both of hydrophobicity and hydrophilicity), which are properties required for a resist composition for immersion exposure. Therefore, the resist composition of the present invention can be preferably used for immersion exposure.

A resist film formed using the resist composition for immersion exposure according to the present invention contains the component (C) (the fluorine-containing compound according to the third aspect of the present invention).

By virtue of containing a fluorine compound, the component (C) exhibits high hydrophobicity. Further, by virtue of containing the —C(=O)—O—$R^2$ group, the component (C) exhibits increased hydrophilicity under basic conditions. The reason for this is that the ester bond [—C(=O)—O—] is decomposed (hydrolyzed) by action of a base (alkali developing solution), thereby generating a hydrophilic group [—C(=O)—OH].

Therefore, a resist film formed using the resist composition for immersion exposure according to the present invention in which the component (C) is blended with the component (A) and the component (B) exhibits high hydrophobicity prior to coming in contact with an alkali developing solution (e.g., during immersion exposure), and the hydrophilicity thereof is enhanced by coming in contact with an alkali developing solution.

As described above, a resist film formed using the resist composition for immersion exposure according to the present invention exhibits high hydrophobicity during immersion exposure. Therefore, the resist film exhibits an excellent water tracking ability (tracking ability of water with respect to the movement of the lens) which is required when immersion exposure is conducted using a scanning-type immersion exposure apparatus as disclosed in Non-Patent Document 1.

Further, as hydrophilicity is enhanced during alkali developing, the resist composition for immersion exposure according to the present invention is capable of effectively reducing defects caused by immersion exposure. More specifically, in liquid immersion lithography, when immersion exposure of a resist film is conducted, the solubility of the exposed portions in an alkali developing solution changes. For example, in the case of a positive resist composition, the solubility of the exposed portions in an alkali developing is increased, whereas in the case of a negative resist composition, the solubility of the exposed portions in an alkali developing is decreased. By conducting alkali developing, the exposed portions are removed in the case of a positive resist composition, whereas the unexposed portions are removed in the case of a negative resist composition, and as a result, a resist pattern is formed.

On the surface of the resist film at portions which were not irradiated with radial rays by immersion exposure (e.g., unexposed portions in the case of a positive resist composition), defects (water mark defects, and the like) caused by the influence of the immersion medium such as water are likely to be generated following alkali developing. However, since the hydrophilicity of a resist film formed using the resist composition for immersion exposure according to the present invention is enhanced during alkali developing, generation of such defects can be reduced.

Further, by using the resist composition for immersion exposure according to the present invention, elution of a substance from the resist film during immersion exposure can be suppressed.

As described above, immersion exposure is a method in which exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air. In immersion exposure, when the resist film comes into contact with the immersion medium, elution of substances within the resist film (component (B), component (D), and the like) into the immersion medium occurs. This elution of a substance causes phenomenons such as degeneration of the resist film and change in the refractive index of the immersion medium, thereby adversely affecting the lithography properties.

The amount of the eluted substance is affected by the properties of the resist film surface (e.g., hydrophilicity, hydrophobicity, and the like). Therefore, it is presumed that the amount of eluted substance can be reduced by enhancing the hydrophobicity of the resist film surface.

As the resist composition for immersion exposure according to the present invention includes the component (C) containing a fluorine atom, the resist composition exhibits high hydrophobicity prior to conducting exposure and alkali developing, as compared to a resist composition containing no component (C). Therefore, it is presumed that the resist composition for immersion exposure according to the present invention can suppress elution of a substance during immersion exposure.

As elution of a substance can be suppressed, by using the resist composition for immersion exposure according to the present invention, phenomenons such as degeneration of the resist film and change in the refractive index of the immersion medium, which occur during immersion exposure, can be suppressed. Further, as variation in the refractive index of the immersion medium can be suppressed, a resist pattern having an excellent shape can be formed. Furthermore, the level of contamination of the lens within the exposure apparatus can be lowered. Therefore, there is no need for protection against these disadvantages, and hence, the present invention can contribute to simplifying the process and the exposure apparatus.

In addition, a resist film formed using the resist composition for immersion exposure according to the present invention hardly swells by water. Therefore, a very fine resist pattern can be formed with a high precision.

Also, the resist composition for immersion exposure according to the present invention exhibits excellent lithography properties with respect to sensitivity, resolution, etching resistance and the like, and is capable of forming a resist pattern without any practical problems when used as a resist for immersion exposure. For example, by using the resist composition for immersion exposure according to the present invention, a very fine resist pattern with a size of no more than 100 nm can be formed.

The hydrophobicity of a resist film can be evaluated by measuring the contact angle thereof against water, for example, the static contact angle (the contact angle between the surface of a water droplet on the resist film in a horizontal state and the resist film surface), the dynamic contact angle (the contact angle at which a water droplet starts to slide when the resist film is inclined (sliding angle), the contact angle at the front-end point of the water droplet in the sliding direction (advancing angle) and the contact angle at the rear-end point of the water droplet in the sliding direction (receding angle)). For example, the higher the hydrophobicity of a resist film, the higher the static angle, advancing angle and receding angle, and smaller the sliding angle.

As shown in FIG. 1, when a droplet 1 is placed on a plane 2 and the plane 2 is gradually inclined, the advancing angle is the angle $\theta_1$ formed between the lower end 1a of the droplet 1 and the plane 2 as the droplet 1 starts to move (slide) on the plane 2. Further, at this time (when the droplet 1 starts to move (slide) on the plane 2), the receding angle is the angle $\theta_2$ formed between the upper end 1b of the droplet 1 and the plane 2, and the sliding angle is the inclination angle $\theta_3$ of the plane 2.

In the present description, the advancing angle, receding angle and sliding angle are measured in the following manner.

First, a resist composition solution is spin-coated onto a silicon substrate, and then heated at a temperature of 110° C. for 60 seconds to form a resist film.

Subsequently, the contact angles can be measured using commercially available measurement apparatuses such as DROP MASTER-700 (product name; manufactured by Kyowa Interface Science Co. Ltd.), AUTO SLIDING ANGLE: SA-30 DM (product name; manufactured by Kyowa Interface Science Co. Ltd.), and AUTO DISPENSER: AD-31 (product name; manufactured by Kyowa Interface Science Co. Ltd.).

With respect to a resist film formed using the resist composition for immersion exposure according to the present invention, it is preferable that the receding angle as measured prior to conducting immersion exposure and alkali developing be 50 degrees or more, more preferably 50 to 150 degrees, still more preferably 50 to 130 degrees, and most preferably 53 to 100 degrees. When the receding angle is at least as large as the lower limit of the above-mentioned range, the effect of suppressing the elution of a substance during immersion exposure is enhanced. The reason for this has not been elucidated yet, but it is presumed that one of the main reasons is related to the hydrophobicity of the resist film. More specifically, it is presumed that since an aqueous substance such as water is used as the immersion medium, higher hydrophobicity has an influence on the swift removal of the immersion medium from the surface of the resist film after the immersion exposure. On the other hand, when the receding angle is no more than the upper limit of the above-mentioned range, the lithography properties become satisfactory.

For the same reasons as described above, with respect to a resist film formed using the resist composition for immersion exposure according to the present invention, it is preferable that the static contact angle as measured prior to conducting immersion exposure and alkali developing be 60 degrees or more, more preferably 63 to 99 degrees, and most preferably 65 to 98 degrees.

Further, with respect to a resist film formed using the resist composition for immersion exposure according to the present invention, it is preferable that the sliding angle as measured prior to conducting immersion exposure and alkali developing be 36 degrees or lower, more preferably 10 to 36 degrees, still more preferably 7 to 30 degrees, and most preferably 14 to 27 degrees. When the receding angle is no more than the upper limit of the above-mentioned range, the effect of suppressing the elution of a substance during immersion exposure is enhanced. On the other hand, when the sliding angle is at least as large as the lower limit of the above-mentioned range, the lithography properties become satisfactory.

The level of the above-mentioned various angles (dynamic contact angle (advancing angle, receding angle and sliding angle) and static contact angle) can be adjusted by the formulation of the resist composition for immersion exposure, for example, the type and amount of the component (C), and the type of the component (A). For example, by increasing the amount of the component (C), the hydrophobicity of the obtained resist composition can be enhanced, and the advancing angle, receding angle and static contact angle becomes large, whereas the sliding angle becomes small.

As described above, the resist composition for immersion exposure according to the present invention exhibits various properties required for a resist material for use in immersion exposure. Therefore, the resist composition of the present invention can be preferably used for immersion exposure.

Further, the component (C) is useful as an additive for a resist composition for immersion exposure.

EXAMPLES

As follows is a description of examples of the present invention, although the scope of the present invention is by no way limited by these examples.

<Synthesis of Fluorine-Containing Compound (C)>

As shown in Examples 1 to 42 below, fluorine-containing compounds were produced as follows.

Example 1

Synthesis Example of Compound (1)

200 ml of a THF solution containing 11.5 g (76.4 mmol) of a fluorinated alcohol ($C_2F_5CH_2OH$), 16 g (83.3 mmol) of ethyldiisopropylaminocarbodiimide hydrochloride (EDCl) and 0.4 g (3.5 mmol) of dimethylaminopyridine (DMAP) was charged into a 500 ml three-necked flask in a nitrogen atmosphere, and 16.0 g (83.3 mmol) of 2-carboxyethyl acrylate was added thereto, followed by stirring for 4 hours to effect a reaction.

After conducting thin-layer chromatography to confirm that the raw materials had been consumed, water was added to stop the reaction. Then, the reaction solvent was concentrated under reduced pressure, and extraction was conducted with ethyl acetate three times. The obtained organic phase was washed with water three times. Thereafter, the solvent was distilled off under reduced pressure, and the resulting product was dried, thereby obtaining 12.5 g of a compound (1) which was an ester compound.

[Chemical Formula 67.]

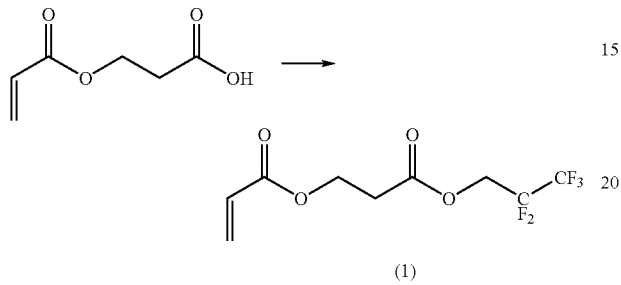

(1)

The obtained compound (1) was analyzed by $^1$H-NMR. The results are shown below.

$^1$H-NMR data(1) (solvent: CDCl$_3$, 400 MHz, internal standard: tetramethylsilane)

δ6.40 d 1H Ha, 6.12 dd 1H Hb, 5.74 d 1H Hc, 4.59 t 2H Hd, 4.42 t 2H He, 2.77 t 2H Hf

From the results shown above, it was confirmed that the compound (1) had a structure shown below.

[Chemical Formula 68.]

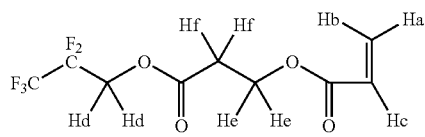

Example 2

Synthesis Example of Compound (2)

200 ml of a THF solution containing 11.5 g (76.4 mmol) of a fluorinated alcohol (C$_2$F$_5$CH$_2$OH), 16 g (83.3 mmol) of ethyldiisopropylaminocarbodiimide hydrochloride (EDCl) and 0.4 g (3.5 mmol) of dimethylaminopyridine (DMAP) was charged into a 500 ml three-necked flask in a nitrogen atmosphere, and 15.0 g (69.4 mmol) of mono(2-acryloyloxyethyl) succinate was added thereto, followed by stirring for 4 hours to effect a reaction.

After conducting thin-layer chromatography to confirm that the raw materials had been consumed, water was added to stop the reaction. Then, the reaction solvent was concentrated under reduced pressure, and extraction was conducted with ethyl acetate three times. The obtained organic phase was washed with water three times. Thereafter, the solvent was distilled off under reduced pressure, and the resulting product was dried, thereby obtaining 21.24 g of a compound (2).

[Chemical Formula 69.]

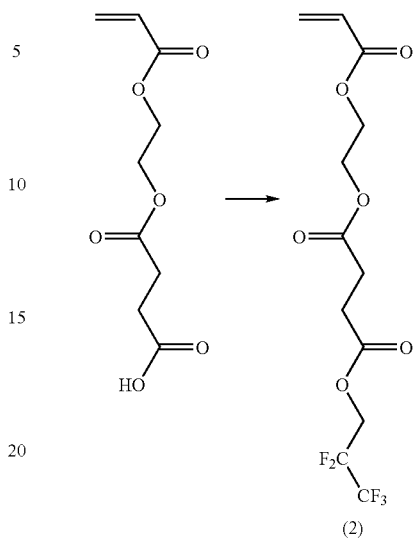

(2)

The obtained compound (2) was analyzed by $^1$H-NMR. The results are shown below.

$^1$H-NMR(CDCl$_3$)6.48-6.43(d, 1H,Ha), 6.20-6.12(dd, 1H,Hb), 5.90-5.87(d,1H,Ha), 4.57(m, 2H,Hg), 4.38-4.33 (m, 4H,He,Hf), 2.76-2.69(m, 4H,Hc,Hd)

From the results shown above, it was confirmed that the compound (2) had a structure shown below.

[Chemical Formula 70.]

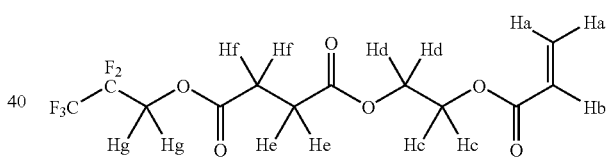

Example 3

Synthesis Example of Polymeric Compound (3)

4.00 g (14.49 mmol) of the compound (1) obtained in Example 1 was charged into a 100 ml three-necked flask equipped with a thermometer and a reflux tube, and 22.67 g of tetrahydrofuran was added thereto and dissolved. Then, 0.58 mmol of dimethyl 2,2'-azobis(isobutyrate) (product name: V-601) as a polymerization initiator was added and dissolved in the resulting solution.

Subsequently, the solution was stirred while heating at 80° C. for 6 hours in a nitrogen atmosphere, and was then cooled to room temperature. The resulting polymer solution was concentrated under reduced pressure, and dropwise added to an excess amount of a methanol/water mixed solvent to thereby precipitate a polymer. Then, the precipitated polymer was separated by filtration, followed by washing and drying, thereby obtaining, as an objective compound, 1.5 g of a polymeric compound (3) represented by formula (3) shown below.

127

With respect to the compound (3), the weight average molecular weight and the dispersity were determined by the polystyrene equivalent value as measured by gel permeation chromatography (GPC). As a result, it was found that the weight average molecular weight was 4,500, and the dispersity was 1.31.

[Chemical Formula 71.]

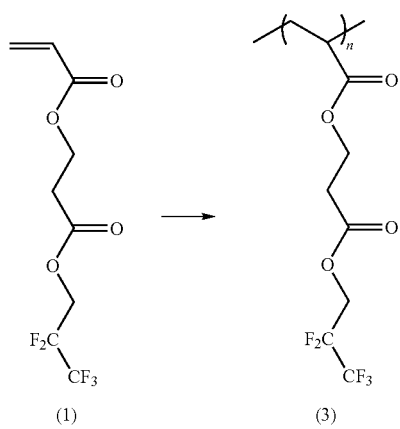

(1)  (3)

Example 4

Synthesis Example of Polymeric Compound (4)

9.00 g (25.86 mmol) of the compound (2) obtained in Example 2 was charged into a 300 ml three-necked flask equipped with a thermometer and a reflux tube, and 51.00 g of tetrahydrofuran was added thereto and dissolved. Then, 0.52 mmol of dimethyl 2,2'-azobis(isobutyrate) (product name: V-601) as a polymerization initiator was added and dissolved in the resulting solution.

Subsequently, the solution was stirred while heating at 80° C. for 6 hours in a nitrogen atmosphere, and was then cooled to room temperature. The resulting polymer solution was concentrated under reduced pressure, and dropwise added to an excess amount of a methanol/water mixed solvent to thereby precipitate a polymer. Then, the precipitated polymer was separated by filtration, followed by washing and drying, thereby obtaining, as an objective compound, 7.2 g of a polymeric compound (4) represented by formula (4) shown below.

With respect to the compound (4), the weight average molecular weight and the dispersity were determined by the polystyrene equivalent value as measured by gel permeation chromatography (GPC). As a result, it was found that the weight average molecular weight was 5,300, and the dispersity was 1.41.

128

[Chemical Formula 72.]

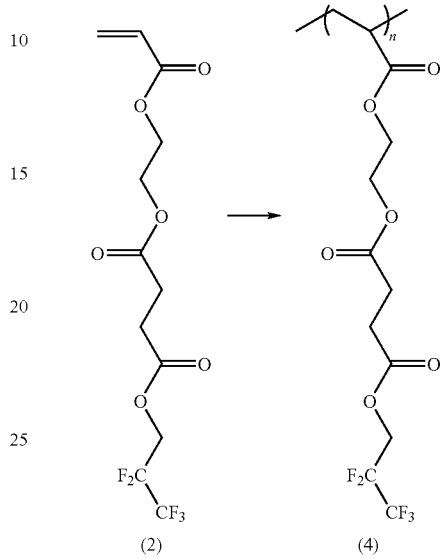

(2)  (4)

Example 5

Synthesis Example of Polymeric Compound (5)

A compound (5) was obtained by performing the following steps 1 to 4.

[Step 1]

16.04 g (90 mmol) of 4-hydroxyphenyl methacrylate, 15.20 g (110 mmol) of potassium carbonate and 100 ml of acetone were charged into a 500 ml three-necked flask in a nitrogen atmosphere, and 20 g (102.53 mmol) of t-butyl bromoacetate was added thereto while maintaining the temperature at 0° C. Then, the resultant was subjected to a reaction at room temperature for 10 hours. After the completion of the reaction, the reaction mixture was subjected to suction filtration, and the filtrate was concentrated under reduced pressure. Then, acetone was removed from the resultant, and extraction was conducted with a mixture of water and ethyl acetate. The resulting organic phase was washed with water three times, followed by concentration under reduced pressure, thereby obtaining 20.1 g of a compound (5-1).

[Chemical Formula 73.]

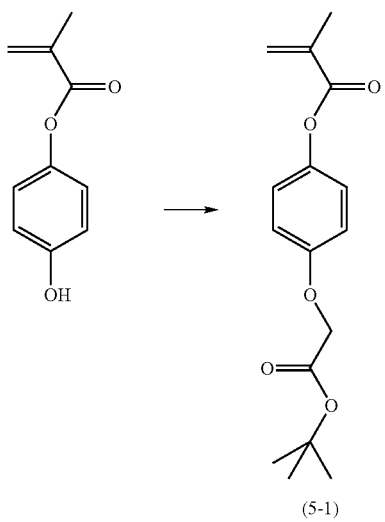

(5-1)

The obtained compound (5-1) was analyzed by $^1$H-NMR. The results are shown below.

$^1$H-NMR data (6) (solvent: CDCl$_3$, 400 MHz, internal standard: tetramethylsilane)

δ7.04 d 2H Ha, 6.90 d 2H Hb, 6.32 s 1H Hc, 5.73 s 1H Hd, 4.50 s 2H He, 2.05 s 3H Hf, 1.49 s 9H Hg

From the results shown above, it was confirmed that the compound (5-1) had a structure shown below.

[Chemical Formula 74.]

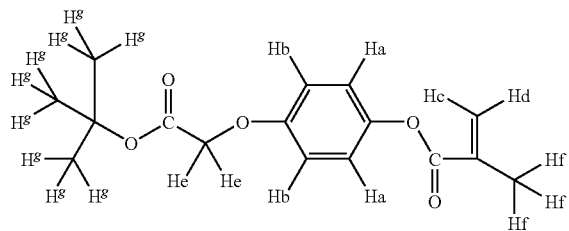

[Step 2]
15.00 g (51.37 mmol) of the compound (5-1) was charged into a 300 ml three-necked flask in a nitrogen atmosphere, and 85.00 g of tetrahydrofuran was added thereto and dissolved. Then, 7.70 mmol of 2,2'-azobis(isobutyrate) (product name: V-601) as a polymerization initiator was added and dissolved in the resulting solution.

Subsequently, the solution was stirred while heating at 80° C. for 6 hours in a nitrogen atmosphere, and was then cooled to room temperature. The resulting polymer solution was concentrated under reduced pressure, and dropwise added to an excess amount of a methanol/water mixed solvent to thereby precipitate a polymer. Then, the precipitated polymer was separated by filtration, followed by washing and drying, thereby obtaining 6.5 g of a polymeric compound (5-2) represented by formula (5-2) shown below.

With respect to the polymeric compound (5-2), the weight average molecular weight and the dispersity were determined by the polystyrene equivalent value as measured by gel permeation chromatography (GPC). As a result, it was found that the weight average molecular weight was 17,300, and the dispersity was 1.68.

[Chemical Formula 75.]

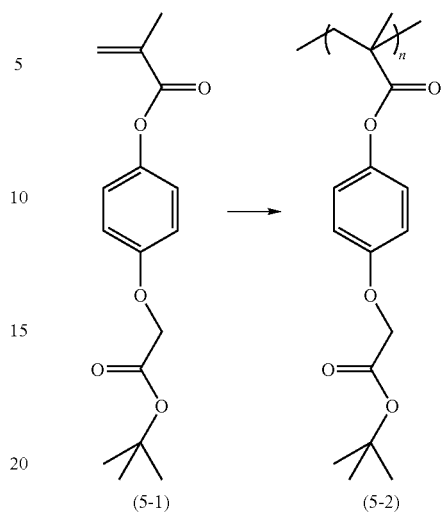

(5-1)            (5-2)

[Step 3]
6.17 g of the polymeric compound (5-2) was dissolved in 100 g of THF, and the resulting solution was charged into a 500 ml three-necked flask in a nitrogen atmosphere. Then, 9.5 g (50 mmol) of p-toluenesulfonic acid hydrate was added thereto, and the resultant was refluxed while heating for 24 hours. After the completion of the reaction, the reaction solution was cooled to room temperature, and THF was removed by concentration under reduced pressure, followed by extraction with a water/ethyl acetate mixed solvent and washing with water three times.

Thereafter, the obtained organic phase was concentrated under reduced pressure, thereby obtaining 3.0 g of a polymeric compound (5-3) represented by formula (5-3) shown below.

With respect to the compound (5-3), the weight average molecular weight and the dispersity were determined by the polystyrene equivalent value as measured by gel permeation chromatography (GPC). As a result, it was found that the weight average molecular weight was 12,500, and the dispersity was 1.70.

[Step 4]
100 ml of a THF solution containing 2.1 g (13.97 mmol) of a fluorinated alcohol (C$_2$F$_5$CH$_2$OH), 2.68 g (13.97 mmol) of ethyldiisopropylaminocarbodiimide hydrochloride (EDCl) and 0.08 g (0.64 mmol) of dimethylaminopyridine (DMAP) was charged into a 500 ml three-necked flask in a nitrogen atmosphere, and 3.0 g of the polymeric compound (5-3) was added thereto. Then, the resultant was stirred for 4 hours, and water was added to stop the reaction. The reaction solvent was concentrated under reduced pressure, and extraction was conducted with ethyl acetate three times. The resulting organic phase was washed with water three times, followed by concentration under reduced pressure. Thereafter, the resulting solid was washed by dispersing in 100 ml of heptane, followed by suction filtration. The solid obtained on the filter paper was dried, thereby obtaining 3.1 g of a polymeric compound (5) represented by formula (5) shown below.

With respect to the compound (5), the weight average molecular weight and the dispersity were determined by the polystyrene equivalent value as measured by gel permeation chromatography (GPC). As a result, it was found that the weight average molecular weight was 16,500, and the dispersity was 1.71.

[Chemical Formula 76.]

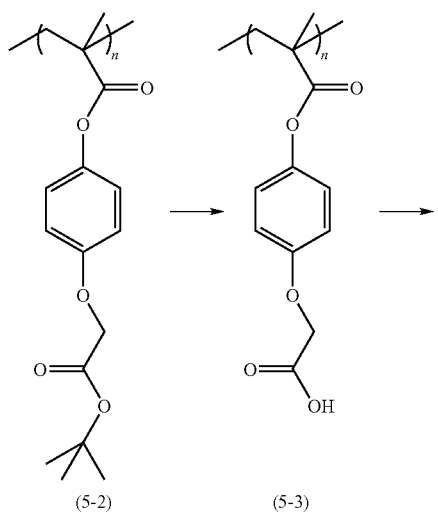

Example 6

Synthesis Example of Compound (6)

45 g (333 mmol) of potassium carbonate and 45 g (296 mmol) of methyl bromoacetate were added to 450 ml of an acetone solution containing 46 g (269 mmol) of 2-vinylnaphthol in a nitrogen atmosphere at 0° C., and then the temperature was elevated to room temperature, followed by stirring for 3 hours. After conducting thin-layer chromatography to confirm that the raw materials had been consumed, the reaction mixture was subjected to filtration, and the obtained filtrate was subjected to distillation under reduced pressure to remove the solvent. Then, water was added to the resultant, and extraction was conducted with ethyl acetate three times. The resulting organic phase was washed with water twice, and then subjected to distillation under reduced pressure to remove the solvent. The resulting crude product was purified by recrystallization (using an n-heptane/ethyl acetate mixture), thereby obtaining 54 g of a compound (6)-1 in the form of a colorless solid (yield: 83%).

Subsequently, 450 ml of a THF solution containing 54 g (222 mmol) of the compound (6)-1 was prepared, and 200 ml of a 25% by weight aqueous solution of TMAH was added thereto, followed by stirring at room temperature for 3 hours. After conducting thin-layer chromatography to confirm that the raw materials had been consumed, THF was distilled off under reduced pressure. Then, the resulting aqueous reaction solution was cooled to 0° C., and 55 ml of a 10N hydrochloric acid was added thereto to render the aqueous reaction solution acidic, followed by extraction with ethyl acetate three times. The resulting organic phase was washed with water twice, and the solvent was distilled off under reduced pressure, thereby obtaining 50 g of a compound (6)-2 in the form of a colorless solid (yield: 98%).

Subsequently, 50 g (222 mmol) of the compound (6)-2 was added to 400 ml of a THF solution containing 33 g (222 mmol) of 2,2,3,3,3-pentafluoro-1-propanol, 51 g (266 mmol) of ethyldiisopropylaminocarbodiimide hydrochloride (EDCl) and 1 g (11 mmol) of dimethylaminopyridine (DMAP) in a nitrogen atmosphere at 0° C., and the temperature was elevated to room temperature, followed by stirring for 3 hours. After conducting thin-layer chromatography to confirm that the raw materials had been consumed, the reaction solution was cooled to 0° C., and water was added thereto to stop the reaction. Then, extraction was conducted with ethyl acetate three times, and the obtained organic phase was washed with water twice. Thereafter, the solvent was distilled off under reduced pressure to obtain a crude product, and the obtained crude product was purified by recrystallization (using an n-heptane/ethyl acetate mixture), thereby obtaining 59 g of a compound (6) in the form of a colorless solid (yield: 74%).

[Chemical Formula 77.]

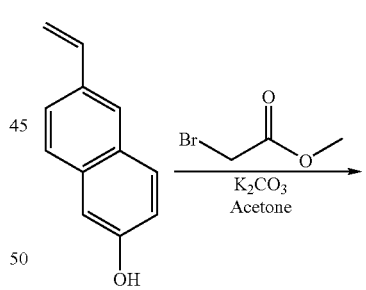

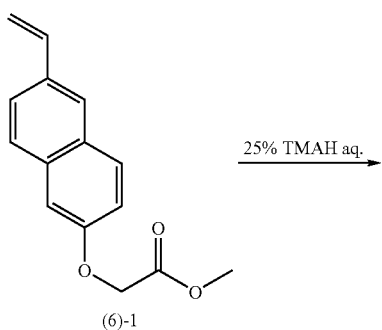

-continued

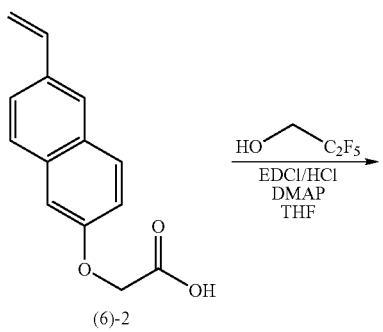
(6)-2

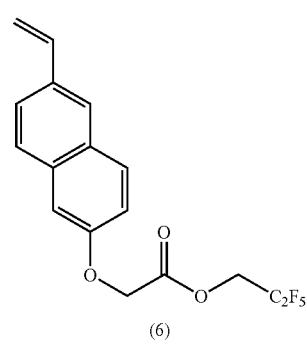
(6)

The obtained compounds (6)-1, (6)-2 and (6) were analyzed by $^1$H-NMR.

The results are shown below.

Spectrum Data of Compound (6)-1

$^1$H-NMR(CDCl$_3$) 7.75-7.60(m, 4H,Hc), 7.25-7.10(m, 2H,Hc), 6.85(dd, 1H,Hb), 5.80(d, 1H,Ha), 5.30(d, 1H,Ha), 4.75(s, 2H,Hd), 3.83(s, 3H,He)

[Chemical Formula 78.]

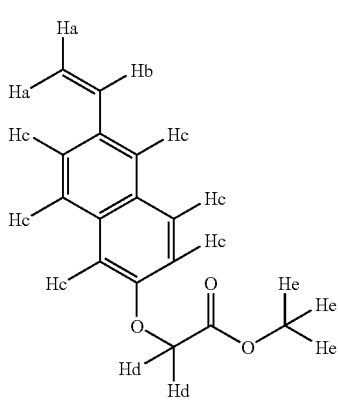
(6)-1

Spectrum Data of Compound (6)-2

$^1$H-NMR(DMSO-d6) 13.15(br, 1H,He), 7.95-7.75(m, 4H,Hc), 7.30-7.20(m, 2H,Hc), 6.85(dd, 1H,Hb), 5.90(d, 1H,Ha), 5.25(d, 1H,Ha), 4.75(s, 2H,Hd)

[Chemical Formula 79.]

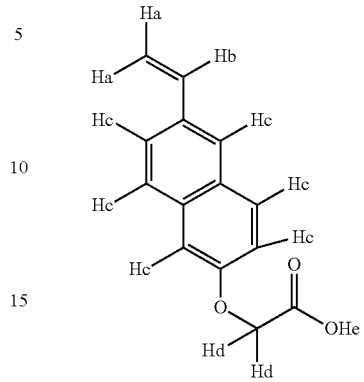
(6)-2

Spectrum Data of Compound (6)

$^1$H-NMR(DMSO-d6) 7.86-7.69(m, 4H,Hc), 7.32(d, 1H,Hc), 7.23(dd, 1H,Hc), 6.86(dd, 1H,Hb), 5.92(d, 1H,Ha), 5.33(d, 1H,Ha), 5.10(s, 2H,Hd), 5.97(t, 2H,He)

[Chemical Formula 80.]

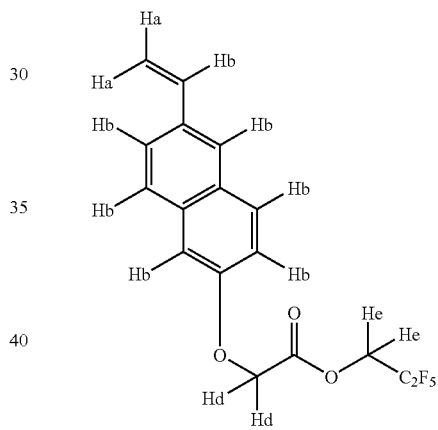
(6)

Example 7

Synthesis Example of Polymeric Compound (8)

3.50 g (9.71 mmol) of the compound (6) and 1.93 g (12.36 mmol) of a compound (7) were charged into a three-necked flask equipped with a thermometer and a reflux tube, and 30.77 g of tetrahydrofuran was added thereto and dissolved. Then, 0.88 mmol of dimethyl 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 2.10 g of a polymeric compound (8) as an objective compound.

With respect to the compound (8), the weight average molecular weight and the dispersity were determined by the polystyrene equivalent value as measured by gel permeation chromatography (GPC). As a result, it was found that the weight average molecular weight was 11,600, and the dispersity was 1.35. Further, the polymeric compound (8) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=56.7/43.3.

[Chemical Formula 81.]

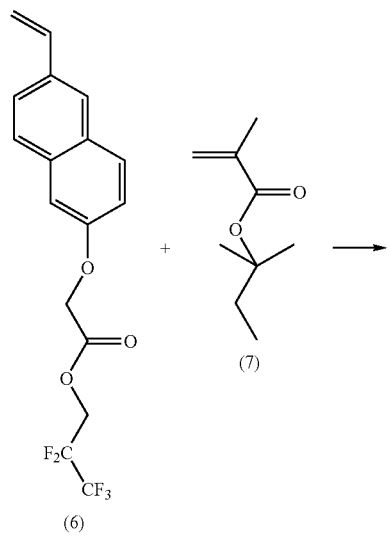

(6)    (7)

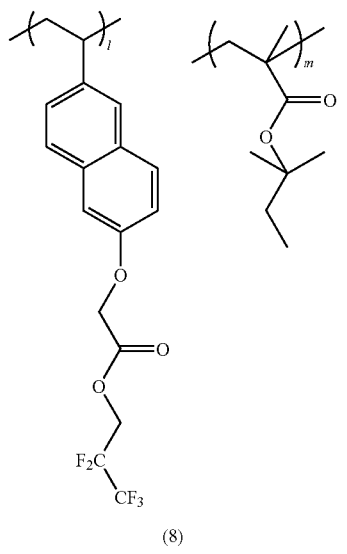

(8)

Example 8

Synthesis Example of Polymeric Compound (9)

5.25 g (14.57 mmol) of the compound (6) and 2.78 g (17.81 mmol) of the compound (7) were charged into a three-necked flask equipped with a thermometer and a reflux tube, and 45.50 g of tetrahydrofuran was added thereto and dissolved. Then, 4.86 mmol of dimethyl 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 3.20 g of a polymeric compound (9) as an objective compound.

With respect to the compound (9), the weight average molecular weight and the dispersity were determined by the polystyrene equivalent value as measured by gel permeation chromatography (GPC). As a result, it was found that the weight average molecular weight was 6,700, and the dispersity was 1.26. Further, the polymeric compound (9) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=57.8/42.2. The polymeric compound (9) is represented by the same chemical formula as that of the polymeric compound (8).

Example 9

Synthesis Example of Polymeric Compound (11)

5.25 g (14.57 mmol) of the compound (6) and 3.28 g (17.81 mmol) of a compound (10) were charged into a three-necked flask equipped with a thermometer and a reflux tube, and 48.34 g of tetrahydrofuran was added thereto and dissolved. Then, 1.29 mmol of dimethyl 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 1.70 g of a polymeric compound (11) as an objective compound.

With respect to the compound (11), the weight average molecular weight and the dispersity were determined by the polystyrene equivalent value as measured by gel permeation chromatography (GPC). As a result, it was found that the weight average molecular weight was 11,700, and the dispersity was 1.27. Further, the polymeric compound (11) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=63.0/37.0.

[Chemical Formula 82.]

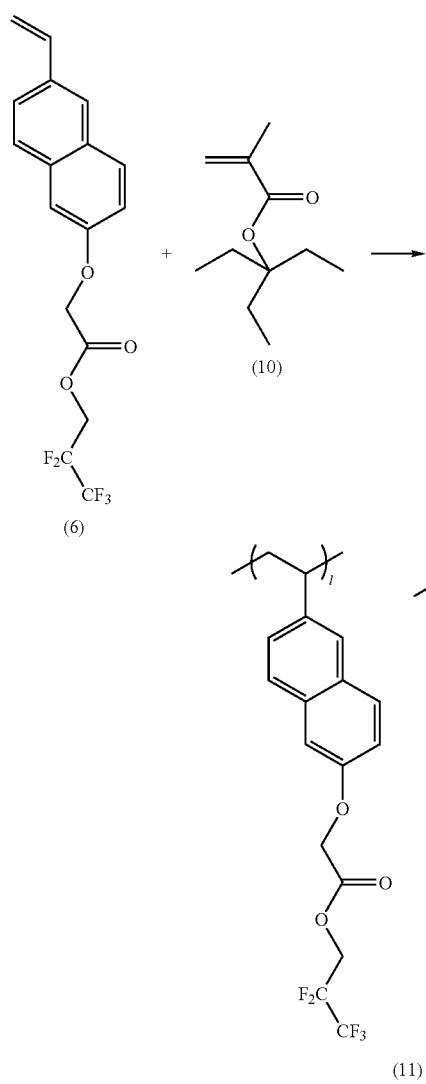

Example 10

Synthesis Example of Polymeric Compound (13)

3.00 g (8.33 mmol) of the compound (6) and 2.95 g (10.60 mmol) of a compound (12) were charged into a three-necked flask equipped with a thermometer and a reflux tube, and 40 g of tetrahydrofuran was added thereto and dissolved. Then, 1.14 mmol of dimethyl 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 2.57 g of a polymeric compound (13) as an objective compound.

With respect to the compound (13), the weight average molecular weight and the dispersity were determined by the polystyrene equivalent value as measured by gel permeation chromatography (GPC). As a result, it was found that the weight average molecular weight was 11,900, and the dispersity was 1.33. Further, the polymeric compound (13) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=59.0/41.0.

[Chemical Formula 83.]

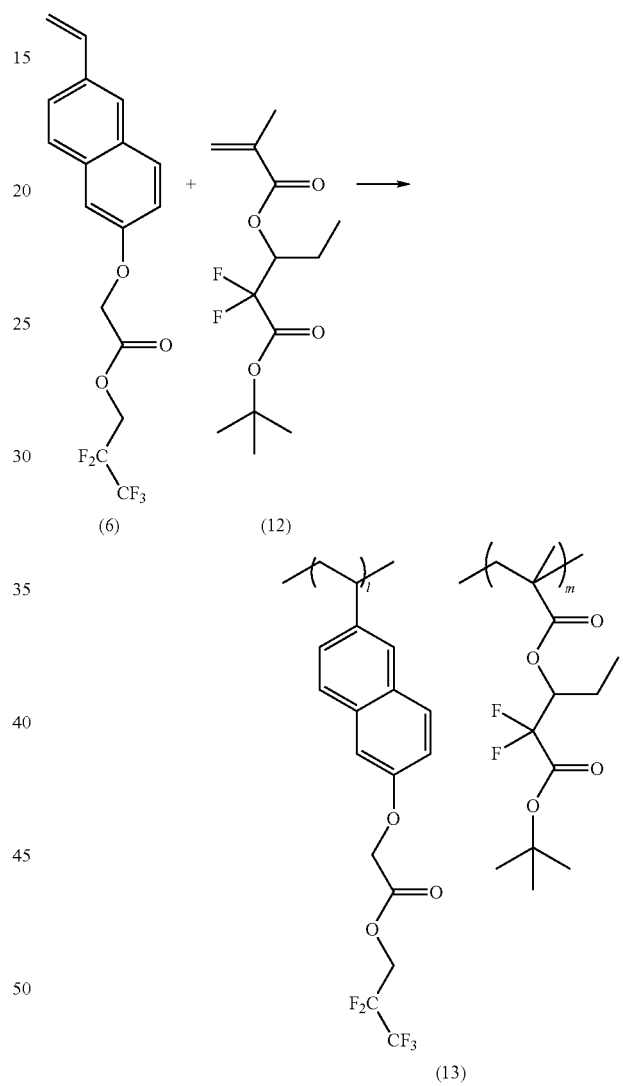

Example 11

Synthesis Example of Polymeric Compound (15)

5.00 g (13.88 mmol) of the compound (6), 1.84 g (11.80 mmol) of the compound (7) and 0.65 g (9.02 mmol) of a compound (14) were charged into a three-necked flask equipped with a thermometer and a reflux tube, and 42.44 g of tetrahydrofuran was added thereto and dissolved. Then, 1.73 mmol of dimethyl 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 2.57 g of a polymeric compound (15) as an objective compound.

With respect to the compound (15), the weight average molecular weight and the dispersity were determined by the polystyrene equivalent value as measured by gel permeation chromatography (GPC). As a result, it was found that the weight average molecular weight was 11,000, and the dispersity was 1.32. Further, the polymeric compound (13) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m/n=53.5/28.6/17.9.

[Chemical Formula 84.]

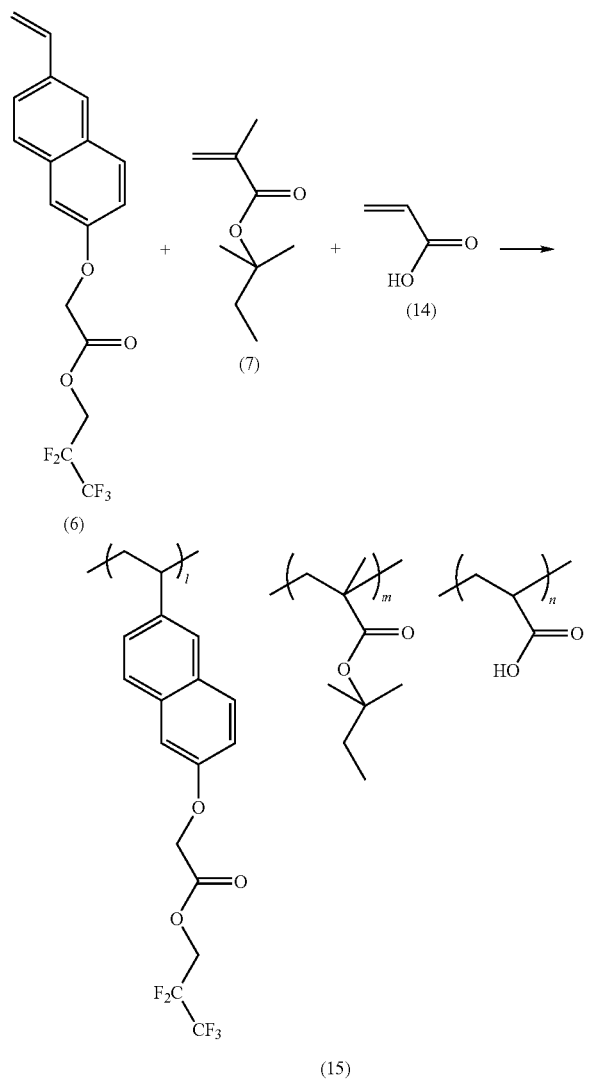

Example 12

Synthesis Example of Compound (16)

61 g (600 mmol) of triethylamine and 64 g (418 mmol) of methyl bromoacetate were added to 300 ml of a THF solution containing 30 g (348 mmol) of methacrylic acid in a nitrogen atmosphere at 0° C., and the temperature was elevated to room temperature, followed by stirring for 3 hours. After conducting thin-layer chromatography to confirm that the raw materials had been consumed, the reaction solution was subjected to distillation under reduced pressure to remove the solvent. Then, water was added to the resultant, and extraction was conducted with ethyl acetate three times. The resulting organic phase was washed with water twice, and then subjected to distillation under reduced pressure to remove the solvent, thereby obtaining 47 g of a compound (16)-1 in the form of a colorless liquid (yield: 85%).

Subsequently, 700 ml of a THF solution containing 30 g (190 mmol) of the compound (16)-1 was prepared, and 700 ml of a 2.38% by weight aqueous solution of TMAH was added thereto, followed by stirring at room temperature for 3 hours. After conducting thin-layer chromatography to confirm that the raw materials had been consumed, THF was distilled off under reduced pressure. Then, the resulting aqueous reaction solution was cooled to 0° C., and 50 ml of a 10N hydrochloric acid was added thereto to render the aqueous reaction solution acidic, followed by extraction with ethyl acetate three times. The resulting organic phase was washed with water twice, and the solvent was distilled off under reduced pressure, thereby obtaining 26 g of a compound (16)-2 in the form of a colorless liquid (yield: 95%).

Subsequently, 17 g (118 mmol) of the compound (16)-2 was added to 100 ml of a THF solution containing 27 g (177 mmol) of 2,2,3,3,3-pentafluoro-1-propanol, 37 g (195 mmol) of ethyldiisopropylaminocarbodiimide hydrochloride (EDCl) and 0.6 g (5 mmol) of dimethylaminopyridine (DMAP) in a nitrogen atmosphere at 0° C., and the temperature was elevated to room temperature, followed by stirring for 3 hours. After conducting thin-layer chromatography to confirm that the raw materials had been consumed, the reaction solution was cooled to 0° C., and water was added thereto to stop the reaction. Then, extraction was conducted with ethyl acetate three times, and the obtained organic phase was washed with water twice. Thereafter, the solvent was distilled off under reduced pressure to obtain a crude product, and the obtained crude product was purified by silica gel filtration (using ethyl acetate), thereby obtaining 19 g of a compound (16) in the form of a colorless liquid (yield: 58%).

[Chemical Formula 85.]

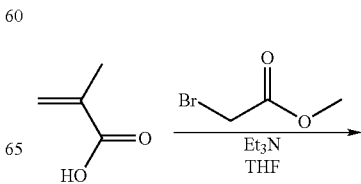

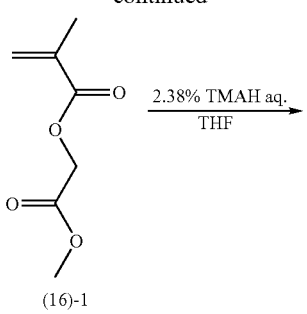

(16)-1

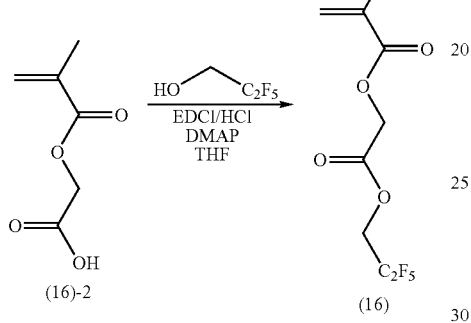

(16)-2    (16)

The obtained compounds (16)-1, (16)-2 and (16) were analyzed by $^1$H-NMR.

The results are shown below.

Spectrum data of compound (16)-1

$^1$H-NMR(CDCl$_3$) 6.23(s, 1H,Hb), 5.67(d, 1H,Hb), 4.13(s, 2H,Hc), 3.78(s, 3H,Hd), 2.00(s, 3H,Ha)

[Chemical Formula 86.]

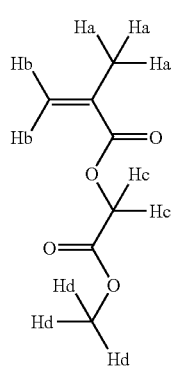

(16)-1

Spectrum Data of Compound (16)-2

$^1$H-NMR(CDCl$_3$) 6.23(s, 1H,Hb), 5.67(d, 1H,Hb), 4.69(s, 2H,Hc), 2.00(s, 3H,Ha)

[Chemical Formula 87.]

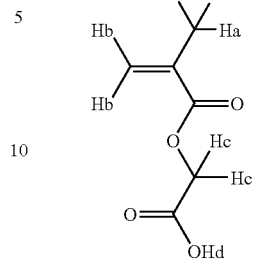

(16)-2

Spectrum Data of Compound (16)

$^1$H-NMR(CDCl$_3$) 6.14(s, 1H,Hb), 5.80(d, 1H,Hb), 4.90(s, 4H,Hc,Hd), 1.92(s, 3H,Ha)

[Chemical Formula 88.]

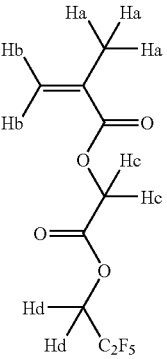

(16)

Example 13

Synthesis Example of Polymeric Compound (17)

3.50 g (12.67 mmol) of the compound (16), 0.82 g (5.28 mmol) of a compound (7) and 0.23 g (3.17 mmol) of a compound (14) were charged into a three-necked flask equipped with a thermometer and a reflux tube, and 25.78 g of tetrahydrofuran was added thereto and dissolved. Then, 1.27 mmol of dimethyl 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 3.40 g of a polymeric compound (17) as an objective compound.

With respect to the compound (17), the weight average molecular weight and the dispersity were determined by the polystyrene equivalent value as measured by gel permeation chromatography (GPC). As a result, it was found that the weight average molecular weight was 14,000, and the dispersity was 1.67. Further, the polymeric compound (17) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m/n=62.3/25.6/12.1.

[Chemical Formula 89.]

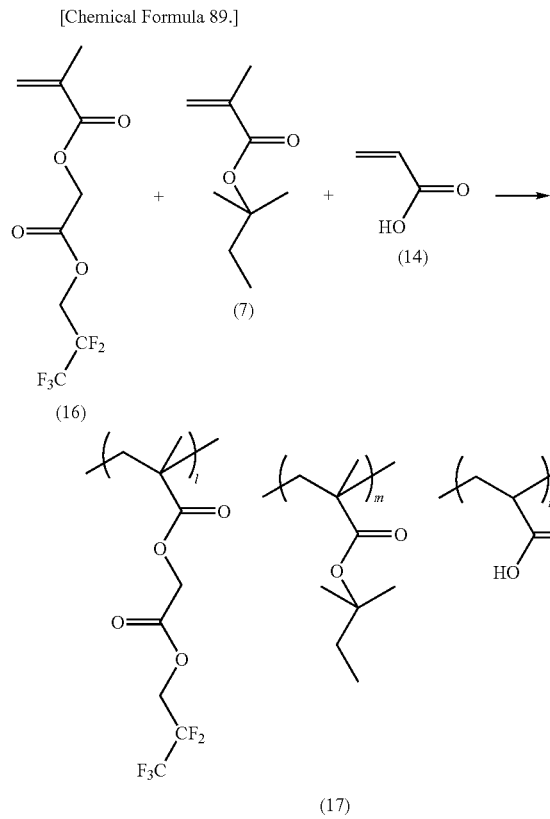

[Chemical Formula 90.]

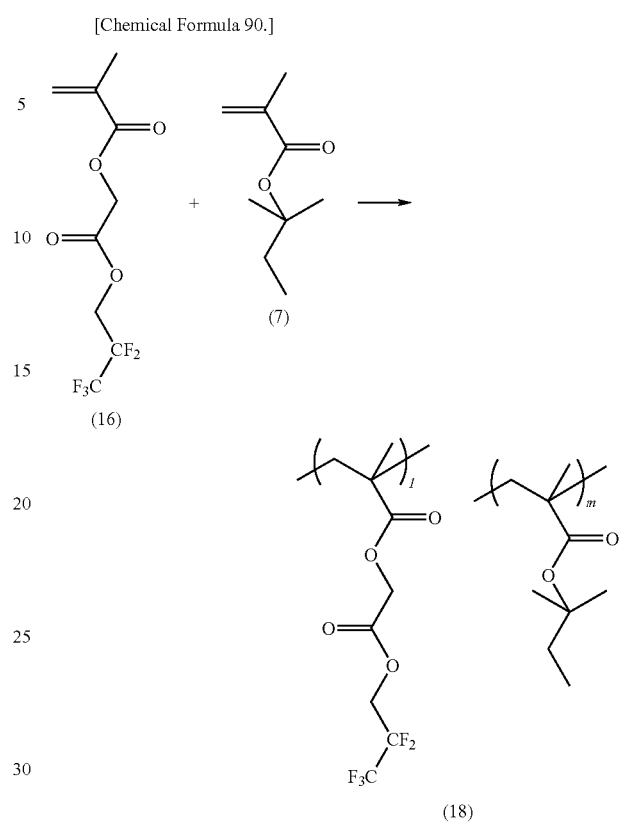

Example 14

Synthesis Example of Polymeric Compound (18)

4.00 g (14.48 mmol) of the compound (16) and 1.51 g (9.67 mmol) of a compound (7) were charged into a three-necked flask equipped with a thermometer and a reflux tube, and 31.5 g of tetrahydrofuran was added thereto and dissolved. Then, 1.21 mmol of dimethyl 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 3.12 g of a polymeric compound (18) as an objective compound.

With respect to the compound (18), the weight average molecular weight and the dispersity were determined by the polystyrene equivalent value as measured by gel permeation chromatography (GPC). As a result, it was found that the weight average molecular weight was 15,300, and the dispersity was 1.50. Further, the polymeric compound (18) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=61.4/38.6.

Example 15

Synthesis Example of Polymeric Compound (19)

4.00 g (14.48 mmol) of the compound (16) and 1.78 g (9.66 mmol) of a compound (10) were charged into a three-necked flask equipped with a thermometer and a reflux tube, and 33.0 g of tetrahydrofuran was added thereto and dissolved. Then, 1.21 mmol of dimethyl 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 0.82 g of a polymeric compound (19) as an objective compound.

With respect to the compound (19), the weight average molecular weight and the dispersity were determined by the polystyrene equivalent value as measured by gel permeation chromatography (GPC). As a result, it was found that the weight average molecular weight was 13,900, and the dispersity was 1.30. Further, the polymeric compound (19) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=69.1/30.9.

[Chemical Formula 91.]

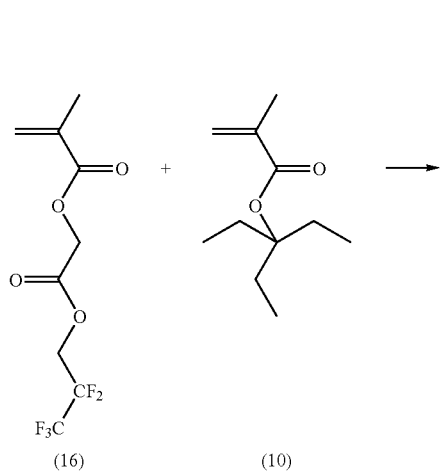

Example 16

Synthesis Example of Polymeric Compound (20)

4.15 g (15.03 mmol) of the compound (16) was charged into a three-necked flask equipped with a thermometer and a reflux tube, and 23.52 g of tetrahydrofuran was added thereto and dissolved. Then, 0.30 mmol of dimethyl 2,2'-azobis (isobutyrate) (product name: V-601) as a polymerization initiator was added and dissolved in the resulting solution. The solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 0.82 g of a polymeric compound (20) as an objective compound.

With respect to the compound (20), the weight average molecular weight and the dispersity were determined by the polystyrene equivalent value as measured by gel permeation chromatography (GPC). As a result, it was found that the weight average molecular weight was 23,000, and the dispersity was 1.80.

[Chemical Formula 92.]

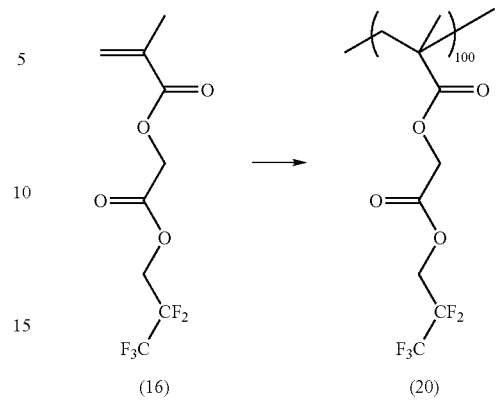

Example 17

Synthesis Example of Polymeric Compound (21)

A polymeric compound (21) was obtained by performing the following steps 1 to 4.

[Step 1]

25 g of ethyl lactate and 200 g of tetrahydrofuran were mixed together in a nitrogen atmosphere at 0° C., and 30.4 g of triethylamine was added thereto while stirring. Then, 20.9 g of methacryloyl chloride was dropwise added thereto, and the temperature of the resultant was elevated to room temperature to effect a reaction for 10 hours. Thereafter, the reaction solution was concentrated under reduced pressure to remove tetrahydrofuran. Then, extraction was conducted with a water/ethyl acetate mixture, and the resulting organic phase was concentrated under reduced pressure, thereby obtaining 31 g of an ester compound (21)-1 as an objective compound.

[Chemical Formula 93.]

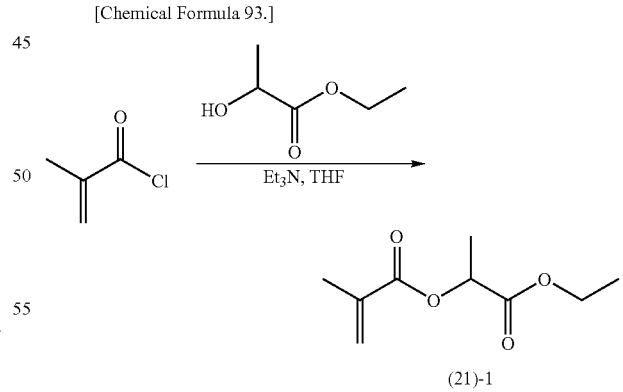

The obtained compound (21)-1 was analyzed by $^1$H-NMR. The results are shown below.

$^1$H-NMR(400 MHz, CDCl$_3$) δ6.20(s, 1H,Ha), 5.62(s, 1H,Hb), 5.12(q, 1H,Hc), 4.21(q, 2H,Hd), 1.97(s, 3H,He), 1.53(d, 3H,Hf), 1.28(t, 3H,Hg)

From the results shown above, it was confirmed that the compound (21)-1 had a structure shown below.

[Chemical Formula 94.]

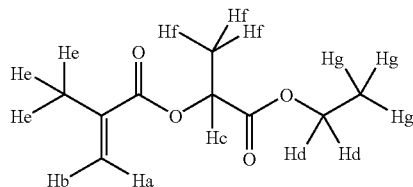

[Step 2]

10 g of the compound (21)-1 and 205.7 g of tetrahydrofuran were charged into a 1L three-necked separable flask and stirred at room temperature. Then, while maintaining the content of the separable flask at 0° C., 205.7 g of a 2.38% by weight aqueous solution of tetramethylammonium hydroxide (TMAH) was added thereto, and the resultant was returned to room temperature and reacted for 1 hour. After the completion of the reaction, the reaction solution was concentrated under reduced pressure to remove tetrahydrofuran, and a 1N HCl was added to render the reaction system acidic, followed by extraction with a water/ethyl acetate mixture. Then, the resulting ethyl acetate solution was concentrated under reduced pressure, thereby obtaining 7.2 g of a compound (21)-2.

[Chemical Formula 95.]

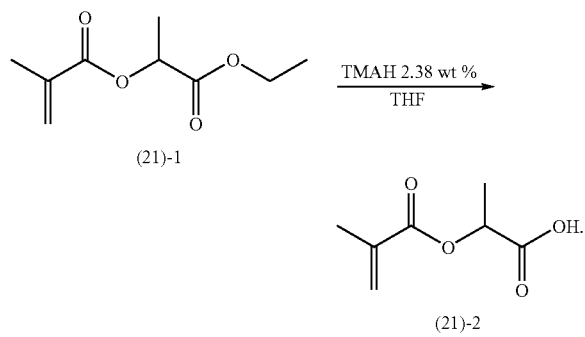

The obtained compound (21)-2 was analyzed by $^1$H-NMR. The results are shown below.

$^1$H-NMR(400 MHz, CDCl$_3$) 66.12(s, 1H,Ha), 5.63(s, 1H,Hb), 5.17(q, 1H,Hc), 1.97(s, 3H,Hd), 1.59(d, 3H,He)

From the results shown above, it was confirmed that the compound (21)-2 had a structure shown below.

[Chemical Formula 96.]

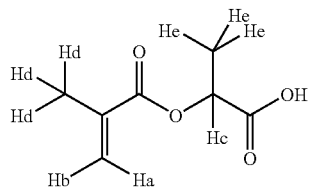

[Step 3]

7.0 g (44.26 mmol) of the compound (21)-2 was added to 100 ml of a THF solution containing 8.0 g (53.11 mmol) of 2,2,3,3,3-pentafluoro-1-propanol (fluorinated alcohol), 12.7 g (66.39 mmol) of ethyldiisopropylaminocarbodiimide hydrochloride (EDCl) and 0.27 g (0.02 mmol) of dimethylaminopyridine (DMAP) in a nitrogen atmosphere at 0° C., and the temperature was elevated to room temperature, followed by stirring for 3 hours. After conducting thin-layer chromatography to confirm that the raw materials had been consumed, the reaction solution was cooled to 0° C., and water was added thereto to stop the reaction. Then, the reaction solution was concentrated under reduced pressure to remove THF, followed by extraction with ethyl acetate three times. The resulting organic phase was washed with water twice, and the solvent was distilled off under reduced pressure. The resultant was dissolved in heptane, followed by suction filtration. The filtrate was concentrated under reduced pressure, thereby obtaining 8.1 g of a compound (21)-3 (yield: 74%).

[Chemical Formula 97.]

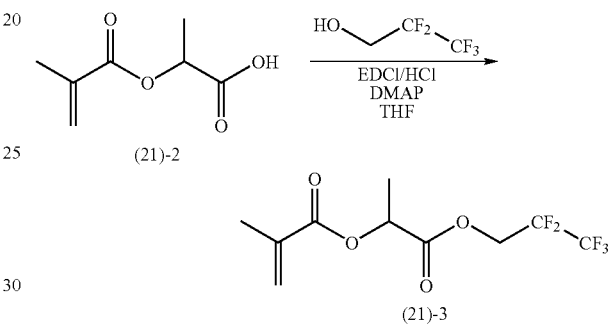

The obtained compound (21)-3 was analyzed by $^1$H-NMR. The results are shown below.

$^1$H-NMR(400 MHz, CDCl$_3$) 66.21(s, 1H,Ha), 5.67(s, 1H,Hb), 5.20(q, 1H,Hc), 4.69(q, 1H,Hd), 4.51(q, 1H,He), 1.98(s, 3H,Hf), 1.58(d, 3H,Hg)

From the results shown above, it was confirmed that the compound (21)-3 had a structure shown below.

[Chemical Formula 98.]

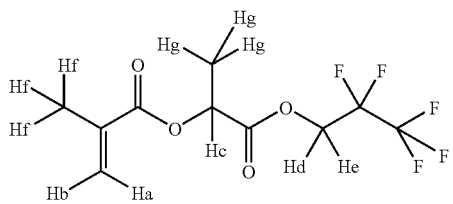

[Step 4]

8.10 g (27.93 mmol) of the compound (21)-3 was charged into a three-necked flask equipped with a thermometer and a reflux tube, and 45.90 g of tetrahydrofuran was added thereto and dissolved. Then, 1.40 mmol of 2,2'-azobis(isobutyrate) (product name: V-601) as a polymerization initiator was added and dissolved in the resulting solution. The solution was stirred while heating at 80° C. for 6 hours in a nitrogen atmosphere, and was then cooled to room temperature.

Subsequently, the resulting polymer solution was concentrated under reduced pressure, and dropwise added to an excess amount of n-heptane to thereby precipitate a polymer. Then, the precipitated polymer was separated by filtration, followed by washing and drying, thereby obtaining 5.3 g of a polymeric compound (21) as an objective compound.

With respect to the polymeric compound (21), the weight average molecular weight and the dispersity were determined by the polystyrene equivalent value as measured by gel permeation chromatography (GPC). As a result, it was found that the weight average molecular weight was 18,900, and the dispersity was 1.55.

[Chemical Formula 99.]

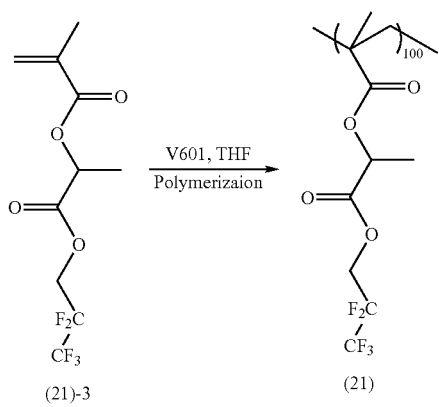

Example 18

Synthesis Example of Polymeric Compound (22)

1.0 g (4.38 mmol) of the aforementioned compound (6)-2 was added to 15 ml of a THF solution containing 0.88 g (5.26 mmol) of 1,1,1,3,3,3-hexafluoro-2-propanol, 1.30 g (81.42 mmol) of ethyldiisopropylaminocarbodiimide hydrochloride (EDCl) and 52 mg (0.43 mmol) of dimethylaminopyridine (DMAP) in a nitrogen atmosphere at 0° C., and the temperature was elevated to room temperature, followed by stirring for 24 hours. After conducting thin-layer chromatography to confirm that the raw materials had been consumed, the reaction solution was cooled to 0° C., and water was added thereto to stop the reaction. Then, extraction was conducted with ethyl acetate three times, and the resulting organic phase was washed with water twice. Thereafter, the solvent was distilled off under reduced pressure, thereby obtaining 1.4 g of a compound (22)-1 in the form of a colorless liquid (yield: 84%).

[Chemical Formula 100.]

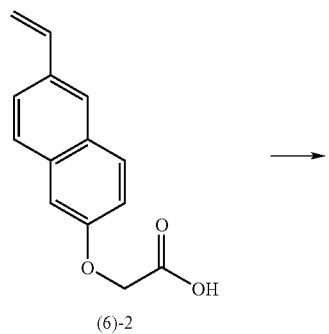

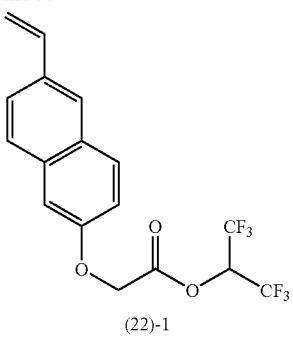

The obtained compound (22)-1 was analyzed by $^1$H-NMR. The results are shown below.

$^1$H-NMR(400 MHz, CDCl$_3$) 7.82-7.05(m, 6H,Hc), 6.83(q, 1H,Hb), 5.85(m, 1H,He), 5.80(d, 1H,Ha), 5.32(d, 1H,Ha), 4.96(s, 2H,Hd)

From the results shown above, it was confirmed that the compound (22)-1 had a structure shown below.

[Chemical Formula 101.]

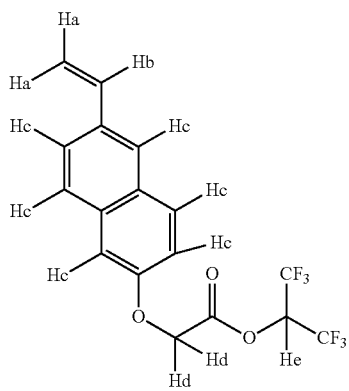

5.67 g of tetrahydrofuran was charged into a three-necked flask equipped with a thermometer and a reflux tube, and 1 g (2.65 mmol) of the compound (22)-1 was added thereto and dissolved. Then, 0.13 mmol of 2,2'-azobis(isobutyrate) (product name: V-601) as a polymerization initiator was added and dissolved in the resulting solution.

Subsequently, the solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 0.5 g of a polymeric compound (22) as an objective compound.

With respect to the polymeric compound (22), the weight average molecular weight and the dispersity were determined by the polystyrene equivalent value as measured by gel permeation chromatography (GPC). As a result, it was found that the weight average molecular weight was 18,800, and the dispersity was 1.25.

[Chemical Formula 102.]

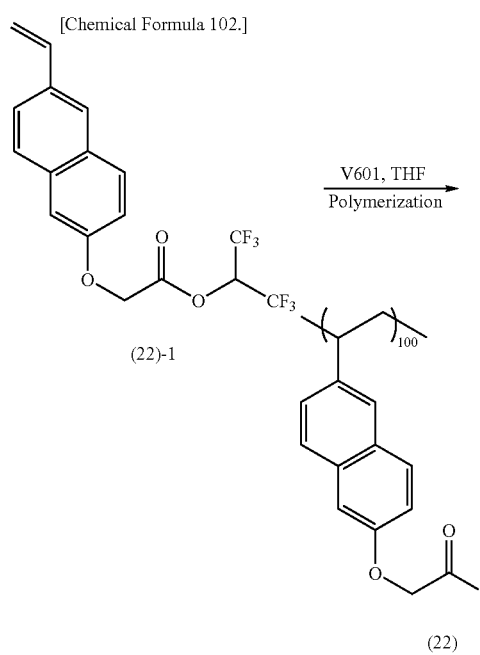

Example 19

Synthesis Example of Polymeric Compound (24)

15.00 g (27.14 mmol) of a compound (23) was added to 100 ml of a THF solution containing 5.29 g (35.28 mmol) of 2,2,3,3,3-pentafluoro-1-propanol, 15.60 g (81.42 mmol) of ethyldiisopropylaminocarbodiimide hydrochloride (EDCl) and 0.17 g (1.36 mmol) of dimethylaminopyridine (DMAP) in a nitrogen atmosphere at 0° C., and the temperature was elevated to room temperature, followed by stirring for 24 hours. After conducting thin-layer chromatography to confirm that the raw materials had been consumed, the reaction solution was cooled to 0° C., and water was added thereto to stop the reaction. Then, extraction was conducted with ethyl acetate three times, and the obtained organic phase was washed with water twice. Thereafter, the solvent was distilled off under reduced pressure, thereby obtaining 26 g of a compound (24)-1 in the form of a colorless liquid (yield: 95%).

[Chemical Formula 103.]

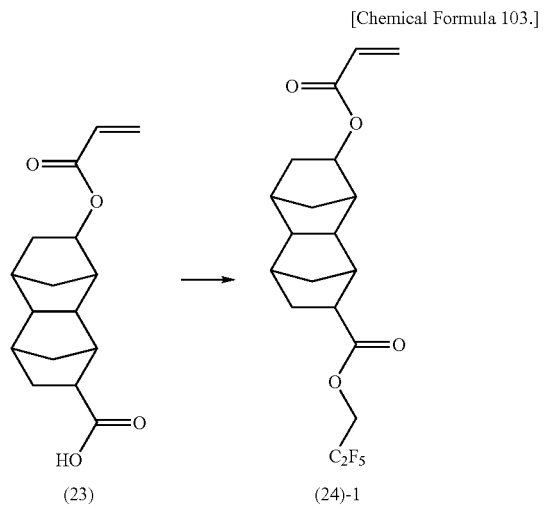

The obtained compound (24)-1 was analyzed by $^1$H-NMR. The results are shown below.

$^1$H-NMR(400 MHz, CDCl$_3$) 6.37(d, 1H,Ha), 6.05(t, 1H,Hb), 5.78(d, 1H,Ha), 5.01, 4.63-4.40(m, 3H,Hc,Hd), 2.86-1.02(m, 15H,He)

From the results shown above, it was confirmed that the compound (24)-1 had a structure shown below.

[Chemical Formula 104.]

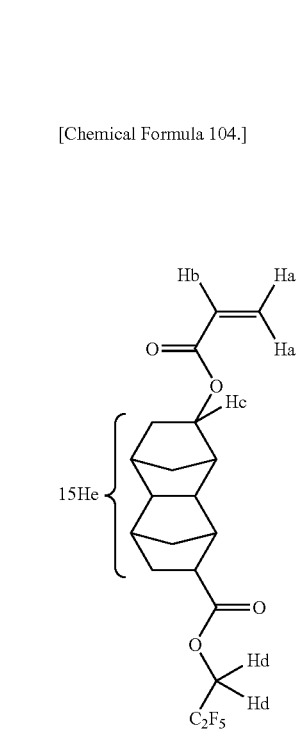

26.67 g of tetrahydrofuran was charged into a three-necked flask equipped with a thermometer and a reflux tube, and 4.00 g (9.80 mmol) of the compound (24)-1 was added thereto and dissolved. Then, 0.404 mmol of 2,2'-azobis(isobutyrate) (product name: V-601) as a polymerization initiator was added and dissolved in the resulting solution.

Subsequently, the solution was stirred while heating at 80° C. for 6 hours in a nitrogen atmosphere, and was then cooled to room temperature. The resulting polymer solution was concentrated under reduced pressure, and dropwise added to an excess amount of n-heptane to thereby precipitate a polymer. Then, the precipitated polymer was separated by filtration, followed by washing and drying, thereby obtaining 1.4 g of a polymeric compound (24) as an objective compound.

With respect to the polymeric compound (24), the weight average molecular weight and the dispersity were determined by the polystyrene equivalent value as measured by gel permeation chromatography (GPC). As a result, it was found that the weight average molecular weight was 5,700, and the dispersity was 2.47.

153

[Chemical Formula 105.]

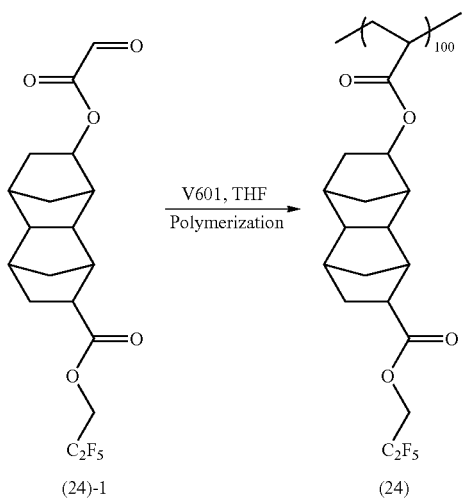

Example 20

Synthesis Example of Compound (25)

40 g (277.5 mmol) of the aforementioned compound (16)-2 was added to 350 ml of a THF solution containing 95.0 g (360.8 mmol) of 3,3,4,4,5,5,6,6,6-nonafluorohexanol, 79.8 g (416.0 mmol) of ethyldiisopropylaminocarbodiimide hydrochloride (EDCl) and 1.7 g (13.8 mmol) of dimethylaminopyridine (DMAP) in a nitrogen atmosphere at 0° C., and the temperature was elevated to room temperature, followed by stirring for 3 hours. After conducting thin-layer chromatography to confirm that the raw materials had been consumed, the reaction solution was cooled to 0° C., and water was added thereto to stop the reaction. Then, extraction was conducted with ethyl acetate three times, and the obtained organic phase was washed with water twice. Thereafter, the solvent was distilled off under reduced pressure to obtain a crude product, and the obtained crude product was purified by silica gel filtration (using ethyl acetate), thereby obtaining 99.6 g of a compound (25) in the form of a colorless liquid.

[Chemical Formula 106.]

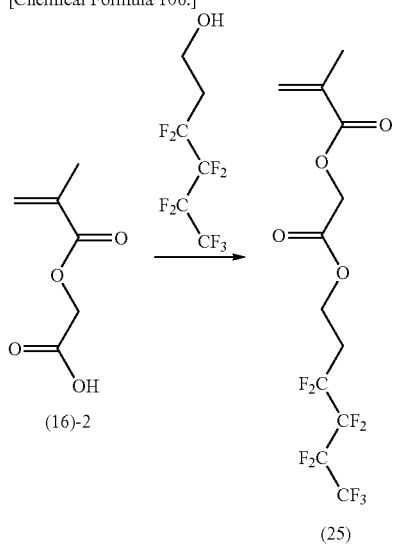

154

The obtained compound (25) was analyzed by $^1$H-NMR. The results are shown below.

$^1$H-NMR(CDCl$_3$) 6.22(s, 1H,Hb), 5.69(s, 1H,Hb), 4.70(s, 2H,Hc), 4.50(t, 2H,Hd), 2.56-2.44(m, 2H,He), 2.00(s, 3H,Ha)

From the results shown above, it was confirmed that the compound (25) had a structure shown below.

[Chemical Formula 107.]

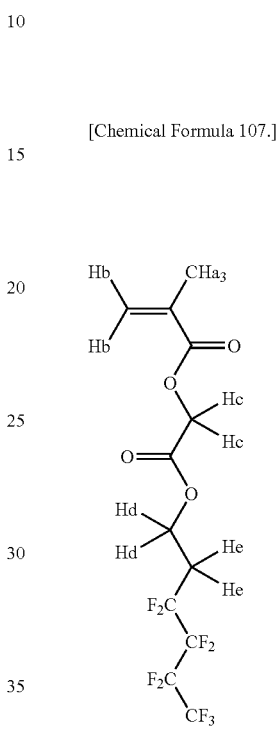

Example 21

Synthesis Example of Compound (26)

20 g (139 mmol) of the aforementioned compound (16)-2 was added to 200 ml of a THF solution containing 33.3 g (167 mmol) of 2,2,3,3,4,4,4-heptafluorobutanol, 38.3 g (200 mmol) of ethyldiisopropylaminocarbodiimide hydrochloride (EDCl) and 0.85 g of dimethylaminopyridine (DMAP) in a nitrogen atmosphere at 0° C., and the temperature was elevated to room temperature, followed by stirring for 3 hours. After conducting thin-layer chromatography to confirm that the raw materials had been consumed, the reaction solution was cooled to 0° C., and water was added thereto to stop the reaction. Then, extraction was conducted with ethyl acetate three times, and the obtained organic phase was washed with water twice. Thereafter, the solvent was distilled off under reduced pressure to obtain a crude product, and the obtained crude product was purified by silica gel filtration (using ethyl acetate), thereby obtaining 23 g of a compound (26) in the form of a colorless liquid.

[Chemical Formula 108.]

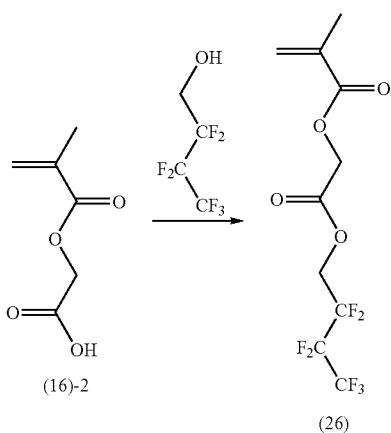

The obtained compound (26) was analyzed by $^1$H-NMR. The results are shown below.

$^1$H-NMR(CDCl$_3$) 6.24(s, 1H,Hb), 5.70(s, 1H,Hb), 4.79(s, 2H,Hc), 4.60-4.66(t, 2H,Hd), 1.99(s, 3H,Ha)

From the results shown above, it was confirmed that the compound (26) had a structure shown below.

[Chemical Formula 109.]

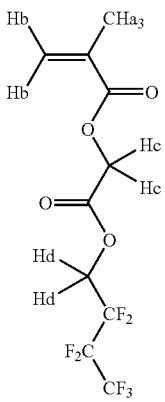

Example 22

Synthesis Example of Compound (27)

26 g (180.39 mmol) of the aforementioned compound (16)-2 was added to 200 ml of a THF solution containing 23.48 g (234.5 mmol) of 2,2,2-trifluoroethanol, 51.9 g (270.6 mmol) of ethyldiisopropylaminocarbodiimide hydrochloride (EDCl) and 0.11 g (0.9 mmol) of dimethylaminopyridine (DMAP) in a nitrogen atmosphere at 0° C., and the temperature was elevated to room temperature, followed by stirring for 3 hours. After conducting thin-layer chromatography to confirm that the raw materials had been consumed, the reaction solution was cooled to 0° C., and water was added thereto to stop the reaction. Then, extraction was conducted with ethyl acetate three times, and the obtained organic phase was washed with water twice. Thereafter, the solvent was distilled off under reduced pressure to obtain a crude product, and the obtained crude product was purified by silica gel filtration (using ethyl acetate), thereby obtaining 25 g of a compound (27) in the form of a colorless liquid.

[Chemical Formula 110.]

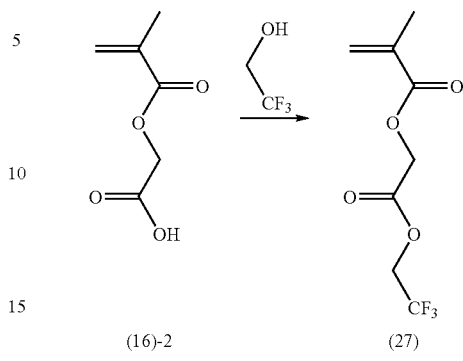

The obtained compound (27) was analyzed by $^1$H-NMR. The results are shown below.

$^1$H-NMR(CDCl$_3$) 6.24(s, 1H,Hb), 5.70(s, 1H,Hb), 4.80(s, 2H,Hc), 4.60-4.51(m, 2H,Hd), 1.99(s, 3H,Ha)

From the results shown above, it was confirmed that the compound (27) had a structure shown below.

[Chemical Formula 111.]

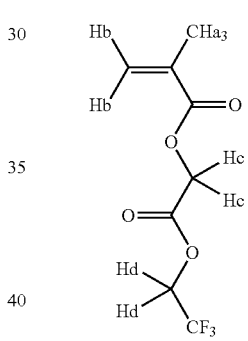

Example 23

Synthesis Example of Compound (28)

20 g (138.8 mmol) of the aforementioned compound (16)-2 was added to 200 ml of a THF solution containing 30.3 g (180.4 mmol) of 1,1,1,3,3,3-hexafluoro-2-propanol, 39.9 g (208.1 mmol) of ethyldiisopropylaminocarbodiimide hydrochloride (EDCl) and 0.08 g (0.7 mmol) of dimethylaminopyridine (DMAP) in a nitrogen atmosphere at 0° C., and the temperature was elevated to room temperature, followed by stirring for 3 hours. After conducting thin-layer chromatography to confirm that the raw materials had been consumed, the reaction solution was cooled to 0° C., and water was added thereto to stop the reaction. Then, extraction was conducted with ethyl acetate three times, and the obtained organic phase was washed with water twice. Thereafter, the solvent was distilled off under reduced pressure to obtain a crude product, and the obtained crude product was purified by silica gel filtration (using ethyl acetate), thereby obtaining 25 g of a compound (28) in the form of a colorless liquid.

[Chemical Formula 112.]

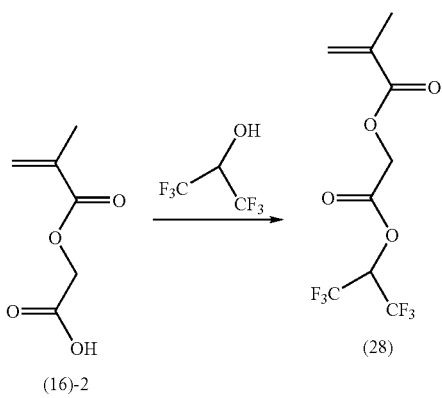

The obtained compound (28) was analyzed by $^1$H-NMR. The results are shown below.

$^1$H-NMR(CDCl$_3$) 6.21(s, 1H,Hb), 5.83-5.76(m, 1H,Hd), 5.70(s, 1H,Hb), 4.89(s, 2H,Hc), 2.00(s, 3H,Ha)

From the results shown above, it was confirmed that the compound (28) had a structure shown below.

[Chemical Formula 113.]

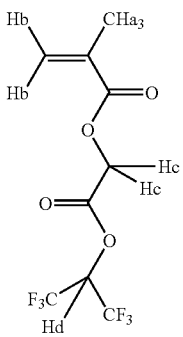

Example 24

Synthesis Example of Polymeric Compound (30)

71.80 g (259.99 mmol) of a compound (16) and 19.41 g (86.66 mmol) of a compound (29) were charged into a three-necked flask equipped with a thermometer and a reflux tube, and 136.82 g of tetrahydrofuran was added thereto and dissolved. Then, 20.80 mmol of dimethyl 2,2'-azobis(isobutyrate) (product name: V-601) as a polymerization initiator was added and dissolved in the resulting solution, and the solution was dropwise added to 76.00 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 32 g of a polymeric compound (30) as an objective compound.

With respect to the compound (30), the weight average molecular weight and the dispersity were determined by the polystyrene equivalent value as measured by gel permeation chromatography (GPC). As a result, it was found that the weight average molecular weight was 25,500, and the dispersity was 1.56. Further, the polymeric compound (30) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=77.3/22.7.

[Chemical Formula 114.]

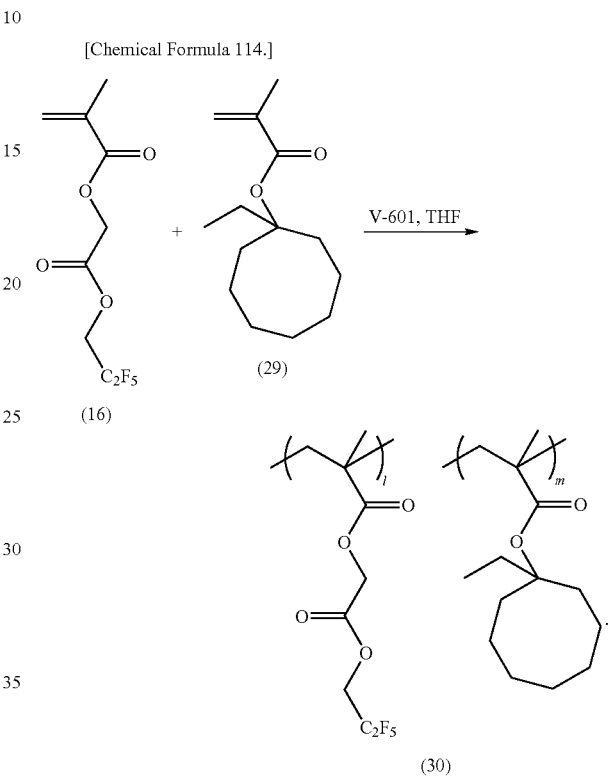

Example 25

Synthesis Example of Polymeric Compound (31)

70.00 g (253.48 mmol) of a compound (16) and 22.08 g (98.58 mmol) of a compound (29) were charged into a three-necked flask equipped with a thermometer and a reflux tube, and 38.12 g of tetrahydrofuran was added thereto and dissolved. Then, 70.41 mmol of dimethyl 2,2'-azobis(isobutyrate) (product name: V-601) as a polymerization initiator was added and dissolved in the resulting solution, and the solution was dropwise added to 76.73 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 53 g of a polymeric compound (31) as an objective compound.

With respect to the compound (31), the weight average molecular weight and the dispersity were determined by the polystyrene equivalent value as measured by gel permeation chromatography (GPC). As a result, it was found that the weight average molecular weight was 13,100, and the dispersity was 1.31. Further, the polymeric compound (31) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=76.6/23.4. The polymeric compound (31) had the same structure as that of the polymeric compound (30).

Example 26

Synthesis Example of Polymeric Compound (32)

20.00 g (72.42 mmol) of a compound (16) and 24.33 g (108.63 mmol) of a compound (29) were charged into a three-necked flask equipped with a thermometer and a reflux tube, and 66.50 g of tetrahydrofuran was added thereto and dissolved. Then, 36.21 mmol of dimethyl 2,2'-azobis(isobutyrate) (product name: V-601) as a polymerization initiator was added and dissolved in the resulting solution, and the solution was dropwise added to 36.94 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 22 g of a polymeric compound (32) as an objective compound.

With respect to the compound (32), the weight average molecular weight and the dispersity were determined by the polystyrene equivalent value as measured by gel permeation chromatography (GPC). As a result, it was found that the weight average molecular weight was 11,900, and the dispersity was 1.44. Further, the polymeric compound (32) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=41.3/58.7. The polymeric compound (32) had the same structure as that of the polymeric compound (30).

Example 27

Synthesis Example of Polymeric Compound (33)

15.00 g (54.32 mmol) of a compound (16) and 4.06 g (18.11 mmol) of a compound (29) were charged into a three-necked flask equipped with a thermometer and a reflux tube, and 28.59 g of tetrahydrofuran was added thereto and dissolved. Then, 1.09 mmol of dimethyl 2,2'-azobis(isobutyrate) (product name: V-601) as a polymerization initiator was added and dissolved in the resulting solution, and the solution was dropwise added to 15.88 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 3 g of a polymeric compound (33) as an objective compound.

With respect to the compound (33), the weight average molecular weight and the dispersity were determined by the polystyrene equivalent value as measured by gel permeation chromatography (GPC). As a result, it was found that the weight average molecular weight was 87,100, and the dispersity was 1.62. Further, the polymeric compound (33) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=76.3/23.7. The polymeric compound (33) had the same structure as that of the polymeric compound (30).

Example 28

Synthesis Example of Polymeric Compound (34)

12.35 g (44.72 mmol) of a compound (16) and 6.68 g (29.81 mmol) of a compound (29) were charged into a three-necked flask equipped with a thermometer and a reflux tube, and 28.55 g of tetrahydrofuran was added thereto and dissolved. Then, 5.22 mmol of dimethyl 2,2'-azobis(isobutyrate) (product name: V-601) as a polymerization initiator was added and dissolved in the resulting solution, and the solution was dropwise added to 15.85 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 6 g of a polymeric compound (34) as an objective compound.

With respect to the compound (34), the weight average molecular weight and the dispersity were determined by the polystyrene equivalent value as measured by gel permeation chromatography (GPC). As a result, it was found that the weight average molecular weight was 28,300, and the dispersity was 1.41. Further, the polymeric compound (34) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=59.5/40.5. The polymeric compound (34) had the same structure as that of the polymeric compound (30).

Example 29

Synthesis Example of Polymeric Compound (35)

15.00 g (54.32 mmol) of a compound (16) and 5.21 g (23.28 mmol) of a compound (29) were charged into a three-necked flask equipped with a thermometer and a reflux tube, and 114.52 g of tetrahydrofuran was added thereto and dissolved. Then, 4.66 mmol of dimethyl 2,2'-azobis(isobutyrate) (product name: V-601) as a polymerization initiator was added and dissolved in the resulting solution. Thereafter, the solution was stirred for 6 hours while heating at 80° C. in a nitrogen atmosphere, and then cooled to room temperature. The resulting polymer solution was concentrated under reduced pressure, and then dropwise added to an excess amount of n-heptane to thereby precipitate a polymer. Then, the precipitated polymer was separated by filtration, followed by washing and drying, thereby obtaining 5.57 g of a polymeric compound (35) as an objective compound.

With respect to the compound (35), the weight average molecular weight and the dispersity were determined by the polystyrene equivalent value as measured by gel permeation chromatography (GPC). As a result, it was found that the weight average molecular weight was 15,000, and the dispersity was 1.37. Further, the polymeric compound (35) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=74.5/25.5. The polymeric compound (35) had the same structure as that of the polymeric compound (30).

Example 30

Synthesis Example of Polymeric Compound (36)

15.00 g (38.44 mmol) of a compound (25) and 3.69 g (16.47 mmol) of a compound (29) were charged into a three-necked flask equipped with a thermometer and a reflux tube, and 105.91 g of tetrahydrofuran was added thereto and dissolved. Then, 3.30 mmol of dimethyl 2,2'-azobis(isobutyrate) (product name: V-601) as a polymerization initiator was added and dissolved in the resulting solution. Thereafter, the solution was stirred for 6 hours while heating at 80° C. in a nitrogen atmosphere, and then cooled to room temperature. The resulting polymer solution was concentrated under reduced pressure, and then dropwise added to an excess amount of n-heptane or a mixed solution of n-heptane and isopropanol to thereby precipitate a polymer. Then, the precipitated polymer was separated by filtration, followed by washing and drying, thereby obtaining 4.26 g of a polymeric compound (36) as an objective compound.

With respect to the compound (36), the weight average molecular weight and the dispersity were determined by the polystyrene equivalent value as measured by gel permeation chromatography (GPC). As a result, it was found that the weight average molecular weight was 16,000, and the dispersity was 1.38. Further, the polymeric compound (36) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=77.2/22.8.

[Chemical Formula 115.]

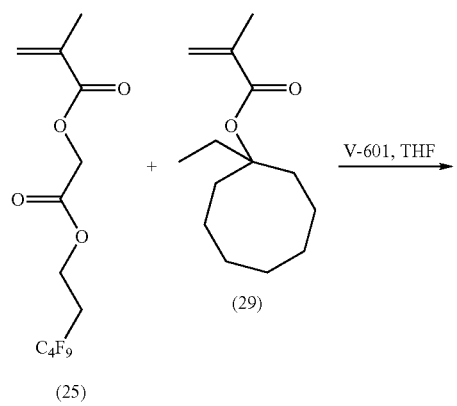

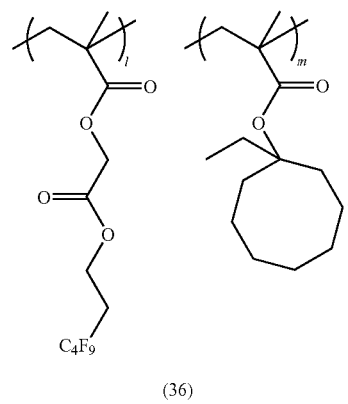

(36)

Example 31

Synthesis Example of Polymeric Compound (37)

14.82 g (41.13 mmol) of a compound (6) and 4.96 g (22.15 mmol) of a compound (29) were charged into a three-necked flask equipped with a thermometer and a reflux tube, and 112.69 g of tetrahydrofuran was added thereto and dissolved. Then, 3.16 mmol of dimethyl 2,2'-azobis(isobutyrate) (product name: V-601) as a polymerization initiator was added and dissolved in the resulting solution. Thereafter, the solution was stirred for 6 hours while heating at 80° C. in a nitrogen atmosphere, and then cooled to room temperature. The resulting polymer solution was concentrated under reduced pressure, and then dropwise added to an excess amount of n-heptane or a mixed solution of n-heptane and isopropanol to thereby precipitate a polymer. Then, the precipitated polymer was separated by filtration, followed by washing and drying, thereby obtaining 3.75 g of a polymeric compound (37) as an objective compound.

With respect to the compound (37), the weight average molecular weight and the dispersity were determined by the polystyrene equivalent value as measured by gel permeation chromatography (GPC). As a result, it was found that the weight average molecular weight was 15,100, and the dispersity was 1.27. Further, the polymeric compound (37) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=75.0/25.0

[Chemical Formula 116.]

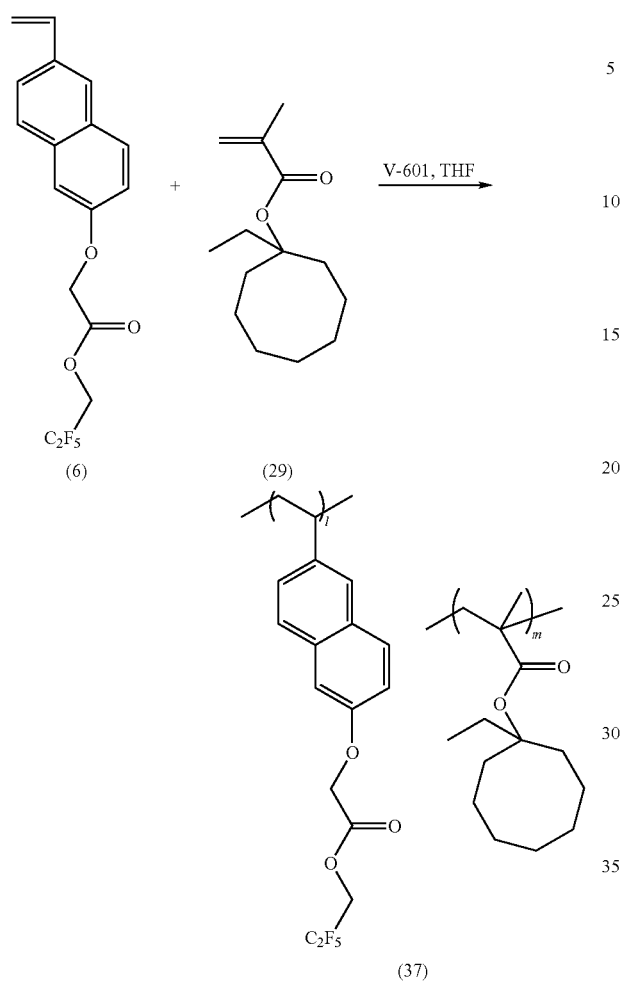

Example 32

Synthesis Example of Polymeric Compound (38)

20.00 g (88.44 mmol) of a compound (27) and 6.60 g (29.48 mmol) of a compound (29) were charged into a three-necked flask equipped with a thermometer and a reflux tube, and 39.90 g of tetrahydrofuran was added thereto and dissolved. Then, 23.58 mmol of dimethyl 2,2'-azobis(isobutyrate) (product name: V-601) as a polymerization initiator was added and dissolved in the resulting solution, and the solution was dropwise added to 22.17 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 13 g of a polymeric compound (38) as an objective compound.

With respect to the compound (38), the weight average molecular weight and the dispersity were determined by the polystyrene equivalent value as measured by gel permeation chromatography (GPC). As a result, it was found that the weight average molecular weight was 13,800, and the dispersity was 1.50. Further, the polymeric compound (38) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=77.6/22.4.

[Chemical Formula 117.]

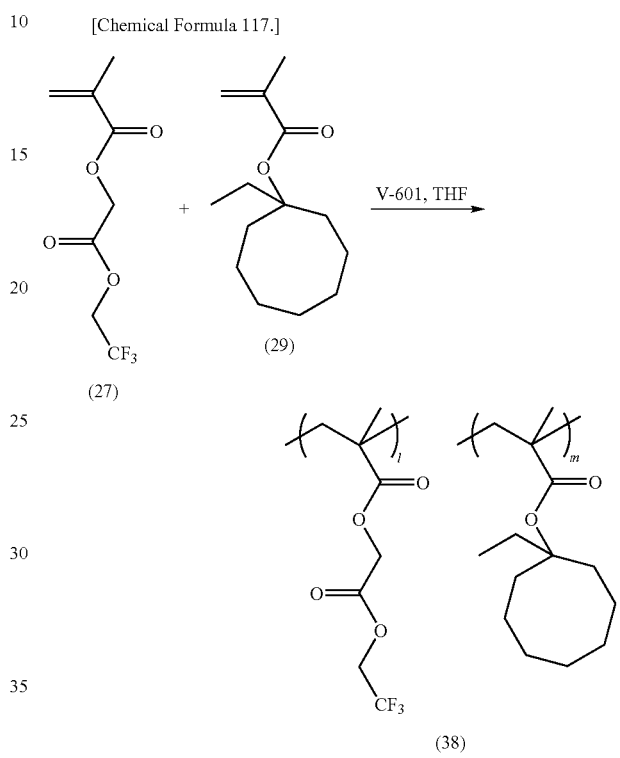

Example 33

Synthesis Example of Polymeric Compound (39)

13.65 g (60.36 mmol) of a compound (27) and 10.20 g (45.53 mmol) of a compound (29) were charged into a three-necked flask equipped with a thermometer and a reflux tube, and 35.78 g of tetrahydrofuran was added thereto and dissolved. Then, 21.18 mmol of dimethyl 2,2'-azobis(isobutyrate) (product name: V-601) as a polymerization initiator was added and dissolved in the resulting solution, and the solution was dropwise added to 19.87 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 14 g of a polymeric compound (39) as an objective compound.

With respect to the compound (39), the weight average molecular weight and the dispersity were determined by the polystyrene equivalent value as measured by gel permeation chromatography (GPC). As a result, it was found that the weight average molecular weight was 14,100, and the dispersity was 1.39. Further, the polymeric compound (38) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=60.3/39.7. The polymeric compound (39) had the same structure as that of the polymeric compound (38).

Example 34

Synthesis Example of Polymeric Compound (40)

20.00 g (61.32 mmol) of a compound (26) and 5.34 g (23.85 mmol) of a compound (29) were charged into a three-necked flask equipped with a thermometer and a reflux tube, and 38.01 g of tetrahydrofuran was added thereto and dissolved. Then, 17.03 mmol of dimethyl 2,2'-azobis(isobutyrate) (product name: V-601) as a polymerization initiator was added and dissolved in the resulting solution, and the solution was dropwise added to 21.17 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 14 g of a polymeric compound (40) as an objective compound.

With respect to the compound (40), the weight average molecular weight and the dispersity were determined by the polystyrene equivalent value as measured by gel permeation chromatography (GPC). As a result, it was found that the weight average molecular weight was 17,100, and the dispersity was 1.35. Further, the polymeric compound (40) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=75.5/24.5.

[Chemical Formula 118.]

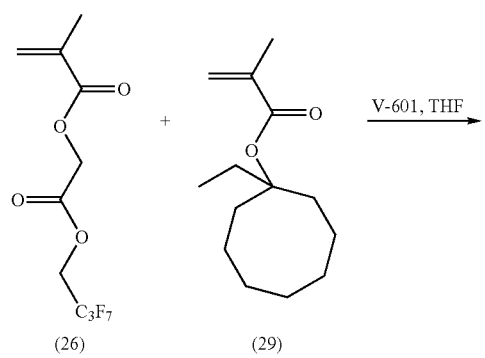

(26) (29)

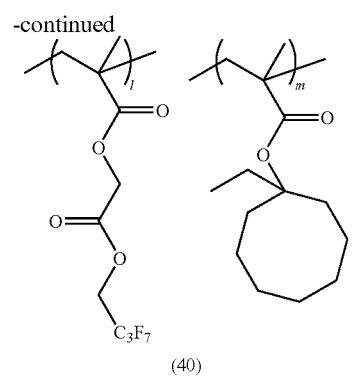

(40)

Example 35

Synthesis Example of Polymeric Compound (41)

10.45 g (32.04 mmol) of a compound (26) and 5.41 g (24.17 mmol) of a compound (29) were charged into a three-necked flask equipped with a thermometer and a reflux tube, and 23.79 g of tetrahydrofuran was added thereto and dissolved. Then, 11.24 mmol of dimethyl 2,2'-azobis(isobutyrate) (product name: V-601) as a polymerization initiator was added and dissolved in the resulting solution, and the solution was dropwise added to 13.22 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 3 g of a polymeric compound (41) as an objective compound.

With respect to the compound (41), the weight average molecular weight and the dispersity were determined by the polystyrene equivalent value as measured by gel permeation chromatography (GPC). As a result, it was found that the weight average molecular weight was 23,700, and the dispersity was 1.51. Further, the polymeric compound (41) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=60.5/39.5. The polymeric compound (41) had the same structure as that of the polymeric compound (40).

Example 36

Synthesis Example of Polymeric Compound (42)

15.00 g (50.99 mmol) of a compound (28) and 3.81 g (17.00 mmol) of a compound (29) were charged into a three-necked flask equipped with a thermometer and a reflux tube, and 28.22 g of tetrahydrofuran was added thereto and dissolved. Then, 13.60 mmol of dimethyl 2,2'-azobis(isobutyrate) (product name: V-601) as a polymerization initiator was added and dissolved in the resulting solution, and the solution was dropwise added to 15.67 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 10 g of a polymeric compound (42) as an objective compound.

With respect to the compound (42), the weight average molecular weight and the dispersity were determined by the polystyrene equivalent value as measured by gel permeation chromatography (GPC). As a result, it was found that the weight average molecular weight was 19,500, and the dispersity was 1.45. Further, the polymeric compound (42) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=76.9/23.1.

[Chemical Formula 119.]

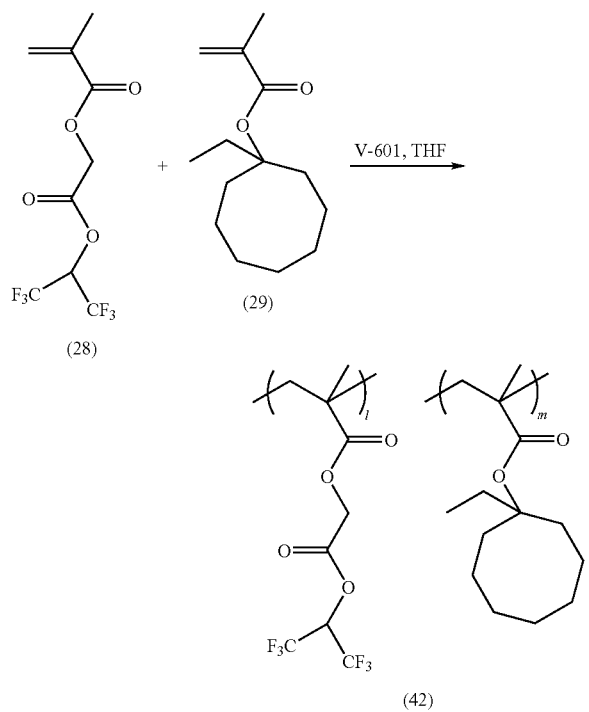

Example 37

Synthesis Example of Polymeric Compound (43)

10.30 g (35.02 mmol) of a compound (28) and 5.92 g (26.42 mmol) of a compound (29) were charged into a three-necked flask equipped with a thermometer and a reflux tube, and 24.33 g of tetrahydrofuran was added thereto and dissolved. Then, 12.29 mmol of dimethyl 2,2'-azobis(isobutyrate) (product name: V-601) as a polymerization initiator was added and dissolved in the resulting solution, and the solution was dropwise added to 13.52 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing and drying, thereby obtaining 1 g of a polymeric compound (43) as an objective compound.

With respect to the compound (43), the weight average molecular weight and the dispersity were determined by the polystyrene equivalent value as measured by gel permeation chromatography (GPC). As a result, it was found that the weight average molecular weight was 38,600, and the dispersity was 1.57. Further, the polymeric compound (43) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=61.7/38.3. The polymeric compound (43) had the same structure as that of the polymeric compound (42).

Example 38

Synthesis Example of Polymeric Compound (44)

11.67 g of tetrahydrofuran was charged into a flask equipped with a thermometer, a reflux tube and a nitrogen-introduction tube, and 5.00 g (22.12 mmol) of a compound (27) was added thereto and dissolved. Then, 1.1 mmol of dimethyl 2,2'-azobis(isobutyrate) (product name: V-601) as a polymerization initiator was added and dissolved in the resulting solution, and a polymerization reaction was performed at 67° C. for 3 hours in a nitrogen atmosphere. After the predetermined period, the reaction solution was cooled to room temperature. Then, the resulting polymer solution was dropwise added to an excess amount of n-heptane to precipitate a polymer, and the precipitated polymer was separated by filtration. The separated polymer was washed with a heptane/isopropanol (IPA) mixed solvent and dried, thereby obtaining 5 g of a polymeric compound (44) as an objective compound.

With respect to the compound (44), the weight average molecular weight and the dispersity were determined by the polystyrene equivalent value as measured by gel permeation chromatography (GPC). As a result, it was found that the weight average molecular weight was 32,000, and the dispersity was 2.78.

[Chemical Formula 120.]

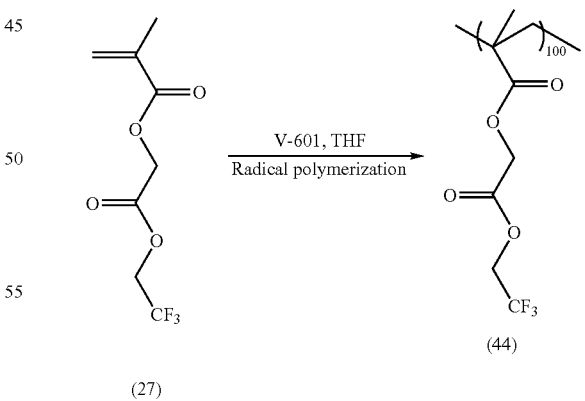

Example 39

Synthesis Example of Polymeric Compound (45)

35 g of tetrahydrofuran was charged into a flask equipped with a thermometer, a reflux tube and a nitrogen-introduction tube, and 15.00 g (66.37 mmol) of a compound (27) was added thereto and dissolved. Then, 16.6 mmol of dimethyl 2,2'-azobis(isobutyrate) (product name: V-601) as a polymerization initiator was added and dissolved in the resulting solution, and a polymerization reaction was performed at 67° C. for 3 hours in a nitrogen atmosphere. After the predetermined period, the reaction solution was cooled to room temperature. Then, the resulting polymer solution was dropwise added to an excess amount of n-heptane to precipitate a polymer, and the precipitated polymer was separated by filtration. The separated polymer was washed with a heptane/IPA mixed solvent and dried, thereby obtaining 12 g of a polymeric compound (45) as an objective compound.

With respect to the compound (45), the weight average molecular weight and the dispersity were determined by the polystyrene equivalent value as measured by gel permeation chromatography (GPC). As a result, it was found that the weight average molecular weight was 15,000, and the dispersity was 2.06.

[Chemical Formula 121.]

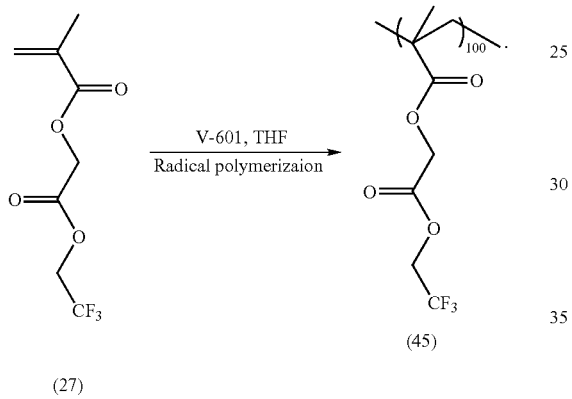

(45)

(27)

Example 40

Synthesis Example of Polymeric Compound (47)

15.00 g (66.37 mmol) of a compound (27) and 5.18 g (22.12 mmol) of a compound (46) were charged into a separable flask equipped with a thermometer, a reflux tube and a nitrogen-introduction tube, and 30.27 g of tetrahydrofuran was added thereto and dissolved. Then, 4.4 mmol of dimethyl 2,2'-azobis(isobutyrate) (product name: V-601) as a polymerization initiator was added and dissolved in the resulting solution, and the solution was dropwise added to 16.82 g of tetrahydrofuran heated to 67° C., over 3 hours in a nitrogen atmosphere, to effect a polymerization reaction. Thereafter, the reaction solution was stirred for 4 hours while heating, and then cooled to room temperature. The resulting polymer solution was dropwise added to an excess amount of n-heptane to thereby precipitate a polymer. Then, the precipitated polymer was separated by filtration, followed by washing with a heptane/IPA mixed solvent and drying, thereby obtaining 17 g of a polymeric compound (47) as an objective compound.

With respect to the compound (47), the weight average molecular weight and the dispersity were determined by the polystyrene equivalent value as measured by gel permeation chromatography (GPC). As a result, it was found that the weight average molecular weight was 28,000, and the dispersity was 2.35. Further, the polymeric compound (47) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=76.9/23.1.

[Chemical Formula 122.]

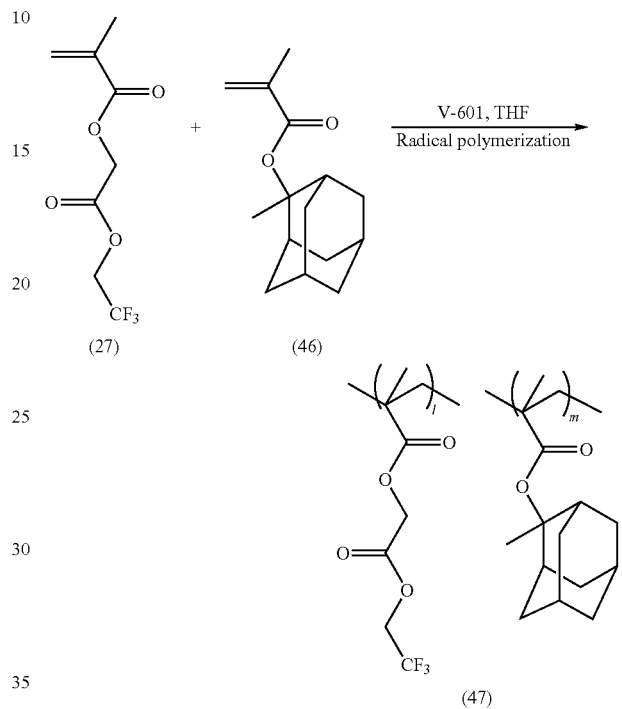

(27)    (46)

(47)

Example 41

Synthesis Example of Polymeric Compound (49)

36.84 g (163 mmol) of a compound (27) was charged into a separable flask equipped with a thermometer, a reflux tube and a nitrogen-introduction tube, and 79.63 g of PGMEA was added thereto and dissolved. Then, 8.6 mmol of dimethyl 2,2'-azobis(isobutyrate) (product name: V-601) as a polymerization initiator was added and dissolved in the resulting solution, and the solution was dropwise added to a PGMEA solution of a compound (48) obtained by dissolving 22 g (83.97 mmol) of a compound (48) in 22 g of PGMEA (weight ratio: compound (48)/PGMEA=1/1) at 80° C., over 3 hours in a nitrogen atmosphere, to effect a polymerization reaction. Thereafter, the reaction solution was stirred for 2 hours while heating, and then cooled to room temperature. The resulting polymer solution was dropwise added to an excess amount of n-heptane to thereby precipitate a polymer. Then, the precipitated polymer was separated by filtration, followed by washing with a heptane/IPA mixed solvent and drying, thereby obtaining 16 g of a polymeric compound (49) as an objective compound.

With respect to the compound (49), the weight average molecular weight and the dispersity were determined by the polystyrene equivalent value as measured by gel permeation chromatography (GPC). As a result, it was found that the weight average molecular weight was 19,800, and the dispersity was 1.80. Further, the polymeric compound (49) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=73.1/26.9.

[Chemical Formula 123.]

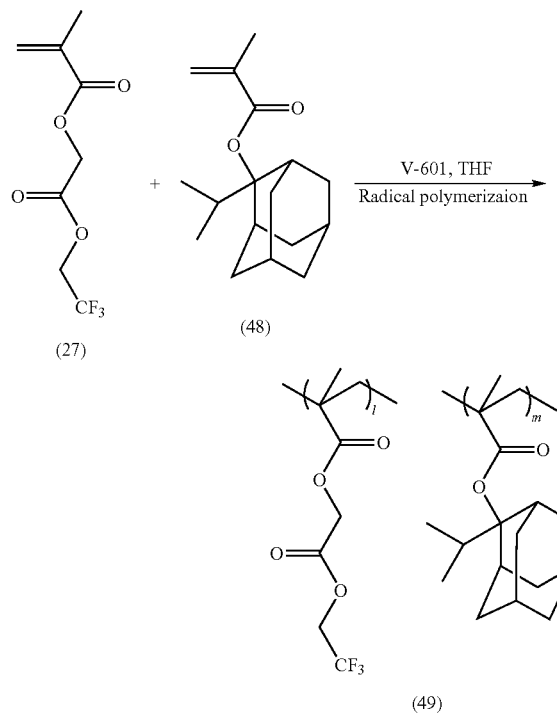

analyzed by carbon 13 nuclear magnetic resonance spectroscopy (600 MHz, $^{13}$C-NMR). As a result, it was found that the composition of the copolymer (ratio (molar ratio) of the respective structural units within the structural formula) was l/m=53.9/46.1.

[Chemical Formula 124.]

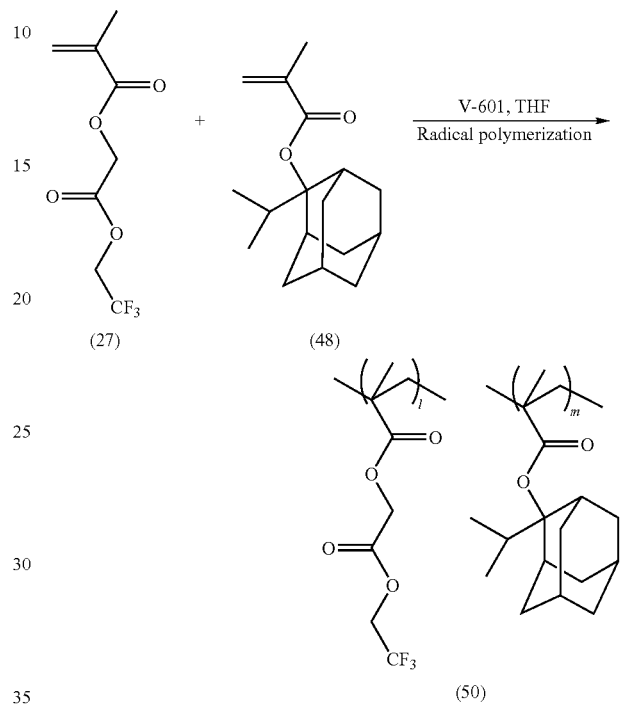

Example 42

Synthesis Example of Polymeric Compound (50)

19.58 g (86.65 mmol) of a compound (27) was charged into a separable flask equipped with a thermometer, a reflux tube and a nitrogen-introduction tube, and 46.32 g of PGMEA was added thereto and dissolved. Then, 5.8 mmol of dimethyl 2,2'-azobis(isobutyrate) (product name: V-601) as a polymerization initiator was added and dissolved in the resulting solution, and the solution was dropwise added to a PGMEA solution of a compound (48) obtained by dissolving 38 g (145.04 mmol) of a compound (48) in 38 g of PGMEA (weight ratio: compound (48)/PGMEA=1/1) at 80° C., over 3 hours in a nitrogen atmosphere, to effect a polymerization reaction. Thereafter, the reaction solution was stirred for 2 hours while heating, and then cooled to room temperature. The resulting polymer solution was dropwise added to an excess amount of n-heptane to thereby precipitate a polymer. Then, the precipitated polymer was separated by filtration, followed by washing with a heptane/IPA mixed solvent and drying, thereby obtaining 8 g of a polymeric compound (50) as an objective compound.

With respect to the compound (50), the weight average molecular weight and the dispersity were determined by the polystyrene equivalent value as measured by gel permeation chromatography (GPC). As a result, it was found that the weight average molecular weight was 18,600, and the dispersity was 1.44. Further, the polymeric compound (50) was <Test for Evaluating Decomposability in Alkali Developing Solution>

With respect to the compound (1), compound (2) and polymeric compound (5) obtained in the aforementioned synthesis examples which were ester compounds, a test for evaluating the decomposability in an alkali developing solution was conducted as follows.

[Test for Compound (1)]

0.1 g of the compound (1), 4.9 g of tetrahydrofuran and 5 g of a 2.38% by weight aqueous solution of tetramethylammonium hydroxide were charged into a screw cap tube, and reacted at room temperature for 1 minute. Then, the resultant was neutralized with 1N—HCl, followed by concentration under reduced pressure to remove tetrahydrofuran. Thereafter, extraction was conducted with a water/ethyl acetate mixed solvent, and the obtained organic phase was concentrated under reduced pressure to obtain a product. The structure of the obtained product was confirmed by $^1$H-NMR to thereby evaluate the decomposability of the compound (1) in an alkali developing solution.

As a result, it was found that 2-carboxyethyl acrylate was generated.

[Test for Compound (2)]

With the exception of using the compound (2) instead of the compound (1), the evaluation of the decomposability of the compound (2) in an alkali developing solution was performed in the same manner as in the evaluation for the compound (1).

As a result, it was found that mono(2-acryloyloxyethyl) succinate was generated.

[Test for Polymeric Compound (5)]

0.1 g of the polymeric compound (5), 4.9 g of tetrahydrofuran and 5 g of a 2.38% by weight aqueous solution of tetramethylammonium hydroxide were charged into a screw cap tube, and reacted at room temperature for 10 hours. Then, the resultant was neutralized with 1N—HCl, followed by concentration under reduced pressure to remove tetrahydrofuran. Thereafter, extraction was conducted with a water/ethyl acetate mixed solvent, and the obtained organic phase was concentrated under reduced pressure to obtain a product. The structure of the obtained product was confirmed by $^1$H-NMR to thereby evaluate the decomposability of the polymeric compound (5) in an alkali developing solution.

As a result, it was found that a polymeric compound (5-3) was generated.

From the results shown above, it was confirmed that each of the compound (1), the compound (2) and the polymeric compound (5) had "—O—CH$_2$—CF$_2$—CF$_3$" within the molecule thereof decomposed to generate "—C(=O)—OH", meaning that these compounds undergo a decomposition reaction by action of an alkali developing solution.

Further, the compounds (25) to (28) and the polymeric compounds (30) to (45), (47), (49) and (50) were tested in the same manner as described above. As a result, it was confirmed that these compounds also undergo a decomposition reaction by action of an alkali developing solution.

<Production of Resist Composition>

Examples 43 to 68 and Comparative Example 1

The components shown in Table 1 were mixed together and dissolved to obtain resist compositions.

TABLE 1

| | Component (A) | Component (B) | Component (C) | Component (D) | Component (E) | Component (S) | |
|---|---|---|---|---|---|---|---|
| Comp. Ex. 1 | (A)-1 [100] | (B)-1 [8.0] | — | (D)-1 [0.12] | (E)-1 [1.32] | (S)-1 [10] | (S)-2 [2500] |
| Ex. 43 | (A)-1 [100] | (B)-1 [8.0] | (C)-1 [3.0] | (D)-1 [0.12] | (E)-1 [1.32] | (S)-1 [10] | (S)-2 [2500] |
| Ex. 44 | (A)-1 [100] | (B)-1 [8.0] | (C)-2 [5.0] | (D)-1 [0.12] | (E)-1 [1.32] | (S)-1 [10] | (S)-2 [2500] |
| Ex. 45 | (A)-1 [100] | (B)-1 [8.0] | (C)-3 [1.0] | (D)-1 [0.12] | (E)-1 [1.32] | (S)-1 [10] | (S)-2 [2500] |
| Ex. 46 | (A)-1 [100] | (B)-1 [8.0] | (C)-3 [5.0] | (D)-1 [0.12] | (E)-1 [1.32] | (S)-1 [10] | (S)-2 [2500] |
| Ex. 47 | (A)-1 [100] | (B)-1 [8.0] | (C)-4 [1.0] | (D)-1 [0.12] | (E)-1 [1.32] | (S)-1 [10] | (S)-2 [2500] |
| Ex. 48 | (A)-1 [100] | (B)-1 [8.0] | (C)-4 [5.0] | (D)-1 [0.12] | (E)-1 [1.32] | (S)-1 [10] | (S)-2 [2500] |
| Ex. 49 | (A)-1 [100] | (B)-1 [8.0] | (C)-5 [1.0] | (D)-1 [0.12] | (E)-1 [1.32] | (S)-1 [10] | (S)-2 [2500] |
| Ex. 50 | (A)-1 [100] | (B)-1 [8.0] | (C)-5 [5.0] | (D)-1 [0.12] | (E)-1 [1.32] | (S)-1 [10] | (S)-2 [2500] |
| Ex. 51 | (A)-1 [100] | (B)-1 [8.0] | (C)-6 [1.0] | (D)-1 [0.12] | (E)-1 [1.32] | (S)-1 [10] | (S)-2 [2500] |
| Ex. 52 | (A)-1 [100] | (B)-1 [8.0] | (C)-6 [5.0] | (D)-1 [0.12] | (E)-1 [1.32] | (S)-1 [10] | (S)-2 [2500] |
| Ex. 53 | (A)-1 [100] | (B)-1 [8.0] | (C)-7 [1.0] | (D)-1 [0.12] | (E)-1 [1.32] | (S)-1 [10] | (S)-2 [2500] |
| Ex. 54 | (A)-1 [100] | (B)-1 [8.0] | (C)-7 [5.0] | (D)-1 [0.12] | (E)-1 [1.32] | (S)-1 [10] | (S)-2 [2500] |
| Ex. 55 | (A)-1 [100] | (B)-1 [8.0] | (C)-8 [1.0] | (D)-1 [0.12] | (E)-1 [1.32] | (S)-1 [10] | (S)-2 [2500] |
| Ex. 56 | (A)-1 [100] | (B)-1 [8.0] | (C)-8 [5.0] | (D)-1 [0.12] | (E)-1 [1.32] | (S)-1 [10] | (S)-2 [2500] |
| Ex. 57 | (A)-1 [100] | (B)-1 [8.0] | (C)-9 [1.0] | (D)-1 [0.12] | (E)-1 [1.32] | (S)-1 [10] | (S)-2 [2500] |
| Ex. 58 | (A)-1 [100] | (B)-1 [8.0] | (C)-9 [5.0] | (D)-1 [0.12] | (E)-1 [1.32] | (S)-1 [10] | (S)-2 [2500] |
| Ex. 59 | (A)-1 [100] | (B)-1 [8.0] | (C)-10 [1.0] | (D)-1 [0.12] | (E)-1 [1.32] | (S)-1 [10] | (S)-2 [2500] |
| Ex. 60 | (A)-1 [100] | (B)-1 [8.0] | (C)-10 [5.0] | (D)-1 [0.12] | (E)-1 [1.32] | (S)-1 [10] | (S)-2 [2500] |
| Ex. 61 | (A)-1 [100] | (B)-1 [8.0] | (C)-11 [1.0] | (D)-1 [0.12] | (E)-1 [1.32] | (S)-1 [10] | (S)-2 [2500] |
| Ex. 62 | (A)-1 [100] | (B)-1 [8.0] | (C)-11 [5.0] | (D)-1 [0.12] | (E)-1 [1.32] | (S)-1 [10] | (S)-2 [2500] |
| Ex. 63 | (A)-1 [100] | (B)-1 [8.0] | (C)-12 [1.0] | (D)-1 [0.12] | (E)-1 [1.32] | (S)-1 [10] | (S)-2 [2500] |
| Ex. 64 | (A)-1 [100] | (B)-1 [8.0] | (C)-12 [5.0] | (D)-1 [0.12] | (E)-1 [1.32] | (S)-1 [10] | (S)-2 [2500] |
| Ex. 65 | (A)-1 [100] | (B)-1 [8.0] | (C)-13 [5.0] | (D)-1 [0.12] | (E)-1 [1.32] | (S)-1 [10] | (S)-2 [2500] |
| Ex. 66 | (A)-1 [100] | (B)-1 [8.0] | (C)-14 [1.0] | (D)-1 [0.12] | (E)-1 [1.32] | (S)-1 [10] | (S)-2 [2500] |
| Ex. 67 | (A)-1 [100] | (B)-1 [8.0] | (C)-14 [5.0] | (D)-1 [0.12] | (E)-1 [1.32] | (S)-1 [10] | (S)-2 [2500] |
| Ex. 68 | (A)-1 [100] | (B)-1 [8.0] | (C)-15 [5.0] | (D)-1 [0.12] | (E)-1 [1.32] | (S)-1 [10] | (S)-2 [2500] |

In Table 1, the reference characters indicate the following. Further, the values in brackets [ ] indicate the amount (in terms of parts by weight) of the component added.

(A)-1: a copolymer represented by chemical formula (A)-1 shown below, having a Mw of 7,000 and a Mw/Mn of 1.8 (in chemical formula (A)-1, the subscript numerals represent the proportion (mol %) of the respective structural units)

[Chemical Formula 125.]

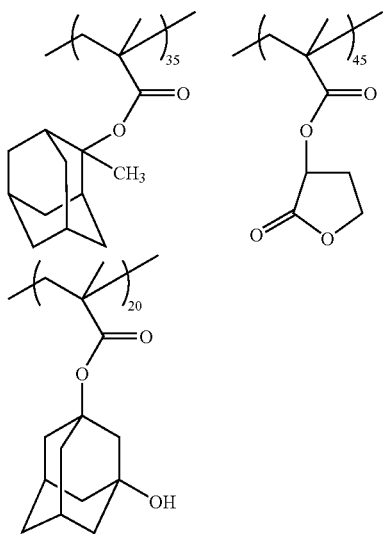

(A)-1

(B)-1: (4-methylphenyl)diphenylsulfonium nonafluoro-n-butanesulfonate
(C)-1: the aforementioned polymeric compound (3)
(C)-2: the aforementioned polymeric compound (4)
(C)-3: the aforementioned polymeric compound (5)
(C)-4: the aforementioned polymeric compound (8)
(C)-5: the aforementioned polymeric compound (9)
(C)-6: the aforementioned polymeric compound (11)
(C)-7: the aforementioned polymeric compound (13)
(C)-8: the aforementioned polymeric compound (15)
(C)-9: the aforementioned polymeric compound (17)
(C)-10: the aforementioned polymeric compound (18)
(C)-11: the aforementioned polymeric compound (19)
(C)-12: the aforementioned polymeric compound (20)
(C)-13: the aforementioned polymeric compound (21)
(C)-14: the aforementioned polymeric compound (22)
(C)-15: the aforementioned polymeric compound (24)
(D)-1: tri-n-pentylamine
(E)-1: salicylic acid
(S)-1: γ-butyrolactone
(S)-2: a mixed solvent of PGMEA/EL=8/2 (weight ratio)

<Measurement of Contact Angle of Resist Film>

Using a spinner, each of the resist compositions of Examples 43 to 68 and Comparative Example 1 was applied onto an 8-inch silicon wafer which had been treated with hexamethyldisilazane (HMDS), and was then prebaked (PAB) on a hotplate at 110° C. for 60 seconds and dried, thereby forming a resist film having a film thickness of 120 nm.

Subsequently, water was dropped onto the surface of the resist film (prior to exposure), and the contact angle (static contact angle) was measured using DROP MASTER-700 (manufactured by Kyowa Interface Science Co. Ltd.) (measurement of contact angle: 2 μL of water). The measured value was defined as the "contact angle prior to developing (°)".

With respect to the wafer after the measurement of the contact angle, development was performed for 30 seconds and 60 seconds at 23° C. in a 2.38% by weight aqueous solution of tetramethylammonium hydroxide (TMAH). Then, the resist film was rinsed for 15 seconds with pure water, and the contact angle was measured in the same manner as described above. The measured values were defined as the "contact angle after 30 seconds development (°)" and "contact angle after 60 seconds development (°)".

Further, with respect to each of the resist films formed using the resist compositions of Examples 43 to 68 and Comparative Example 1, the difference between the contact angle prior to development and the contact angle after 60 seconds development was determined as "Δ contact angle (°)". The results are shown in Table 2.

TABLE 2

| | Contact angle prior to development (°) | Contact angle after 30 seconds development (°) | Contact angle after 60 seconds development (°) | Δ contact angle (°) |
|---|---|---|---|---|
| Comp. Ex. 1 | 68.2 | 59.5 | 59.4 | 8.8 |
| Ex. 43 | 73.8 | 68.6 | 66.2 | 7.6 |
| Ex. 44 | 75.2 | 70.2 | 70.4 | 4.8 |
| Ex. 45 | 72.6 | 57.0 | 56.8 | 15.8 |
| Ex. 46 | 84.6 | 56.1 | 55.6 | 29.0 |
| Ex. 47 | 81.9 | 64.2 | 65.7 | 16.2 |
| Ex. 48 | 92.3 | 67.4 | 66.5 | 25.8 |
| Ex. 49 | 77.0 | 60.4 | 57.8 | 19.2 |
| Ex. 50 | 90.4 | 59.9 | 57.4 | 33.0 |
| Ex. 51 | 80.6 | 59.5 | 58.8 | 21.8 |
| Ex. 52 | 95.0 | 59.3 | 58.2 | 36.8 |
| Ex. 53 | 83.7 | 62.7 | 66.7 | 17.0 |
| Ex. 54 | 91.6 | 64.5 | 66.7 | 24.9 |
| Ex. 55 | 76.2 | 61.1 | 60.1 | 16.1 |
| Ex. 56 | 93.5 | 60.8 | 60.5 | 33.0 |
| Ex. 57 | 76.5 | 59.5 | 58.6 | 17.9 |
| Ex. 58 | 92.9 | 60.3 | 58.1 | 34.8 |
| Ex. 59 | 81.3 | 60.0 | 60.1 | 21.2 |
| Ex. 60 | 96.0 | 61.0 | 60.2 | 35.8 |
| Ex. 61 | 82.1 | 60.5 | 61.0 | 21.1 |
| Ex. 62 | 96.5 | 60.8 | 61.4 | 35.1 |
| Ex. 63 | 85.3 | 58.1 | 58.0 | 27.3 |
| Ex. 64 | 97.4 | 60.1 | 56.3 | 41.1 |
| Ex. 65 | 95.5 | 70.9 | 70.5 | 25.0 |
| Ex. 66 | 87.9 | 62.3 | 60.2 | 27.7 |
| Ex. 67 | 101.2 | 60.1 | 55.3 | 45.9 |
| Ex. 68 | 90.0 | 83.5 | 78.8 | 11.2 |

As seen from the results shown in Table 2, the resist films formed using the resist compositions of Examples 43 to 68 including the fluorine-containing compound of the present invention exhibited a high contact angle prior to development, as compared to the resist film formed using the resist composition of Comparative Example 1 including no fluorine-containing compound of the present invention.

Therefore, it was found that by virtue of including the fluorine-containing compound of the present invention, the hydrophobicity of the resist film is enhanced. As a result, it is expected that not only can the water tracking ability during immersion exposure using a scanning-type immersion exposure apparatus be improved, but also elution of a substance can be suppressed.

Further, as seen from the results shown in Table 2, with respect to each of the resist films formed using the resist compositions of Examples 43 to 68, both the contact angle after 30 seconds development and the contact angle after 60 seconds development were smaller than the contact angle prior to development.

Therefore, it was found that by virtue of including the fluorine-containing compound of the present invention, the hydrophilicity of the resist film can be enhanced by alkali development. As a result, it is expected that defects ascribed to immersion lithography can be reduced.

As described above, it was confirmed that the resist films formed using the resist compositions of Examples 43 to 68 exhibited a high hydrophobicity during immersion exposure, as compared to the resist film formed using the resist composition of Comparative Example 1. Further, the hydrophilicity during alkali developing becomes higher than that prior to development.

<Formation of Resist Pattern>

An organic anti-reflection film composition (product name: ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 89 nm. Then, each of the positive resist composition obtained above was applied onto the anti-reflection film using a spinner, and was then prebaked (PAB) on a hotplate at 110° C. for 60 seconds and dried, thereby forming a resist film having a film thickness of 100 nm.

Subsequently, the resist film was selectively irradiated with an ArF excimer laser (193 nm) through a mask pattern, using an ArF immersion exposure apparatus NSR-S609B (manufactured by Nikon Corporation, NA (numerical aperture)=1.07, σ0.97). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, in each of the examples, a line and space pattern with a line width of 55 nm and a pitch of 110 nm was formed on the resist film.

From the results above, it was confirmed that the resist compositions of Examples 43 to 68 within the scope of the present invention were preferable for immersion exposure.

Further, it was confirmed that the fluorine-containing compounds of Examples 1 to 42 within the scope of the present invention were useful as an additive for a resist composition for immersion exposure.

The invention claimed is:

1. A fluorine-containing compound represented by general formula (c-1-2) shown below:

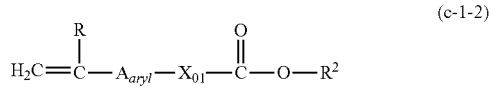

(c-1-2)

wherein each R independently represents a hydrogen atom, a lower alkyl group or a halogenated lower alkyl group; $A_{aryl}$ represents an aromatic cyclic group which may have a substituent; $X_{01}$ represents —O—, —C(=O)—, —C(=O)—O—, a carbonate bond (—O—C(=O)—O—), —NH—C(=O)—, a combination of these groups, or a combination of these groups with an alkylene group of 1 to 10 carbon atoms; and $R^2$ represents a fluorinated hydrocarbon group having 1 to 5 carbon atoms.

2. A resist composition for immersion exposure, comprising a base component (A) that exhibits changed solubility in an alkali developing solution under action of acid, an acid generator component (B) that generates acid upon exposure, and a fluorine-containing compound according to claim 1.

3. The resist composition for immersion exposure according to claim 2, wherein said base component (A) is a base component that exhibits increased solubility in an alkali developing solution under action of acid.

4. The resist composition for immersion exposure according to claim 3, wherein said base component (A) comprises a resin component (A1) that exhibits increased solubility in an alkali developing solution under action of acid, and said resin component (A1) comprises a structural unit (a1) derived from an acrylate ester containing an acid dissociable, dissolution inhibiting group.

5. The resist composition for immersion exposure according to claim 4, wherein said resin component (A1) further comprises a structural unit (a2) derived from an acrylate ester containing a lactone-containing cyclic group.

6. The resist composition for immersion exposure according to claim 4, wherein said resin component (A1) further comprises a structural unit (a3) derived from an acrylate ester containing a polar group-containing aliphatic hydrocarbon group.

7. The resist composition for immersion exposure according to claim 2, further comprising a nitrogen-containing organic compound (D).

8. A method of forming a resist pattern, comprising: forming a resist film using a resist composition for immersion exposure according to claim 2, subjecting said resist film to immersion exposure, and subjecting said resist film to alkali developing to form a resist pattern.

9. The fluorine-containing compound according to claim 1, wherein each $R^2$ independently represents —CH$_2$—CF$_3$, —CH$_2$—CF$_2$—CF$_3$ or —CH(CF$_3$)$_2$.

10. A fluorine-containing compound comprising a structural unit represented by general formula (c-1-4) shown below:

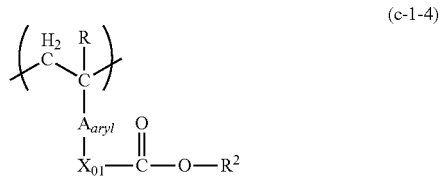

(c-1-4)

wherein each R independently represents a hydrogen atom, a lower alkyl group or a halogenated lower alkyl group; $A_{aryl}$ represents an aromatic cyclic group which may have a substituent; $X_{01}$ represents —O—, —C(=O)—, —C(=O)—O—, a carbonate bond (—O—C(=O)—O—), —NH—C(=O)—, a combination of these groups, or a combination of these groups with an alkylene group of 1 to 10 carbon atoms; and $R^2$ represents a fluorinated hydrocarbon group having 1 to 5 carbon atoms.

11. The fluorine-containing compound according to claim 10, wherein each $R^2$ independently represents —CH$_2$—CF$_3$, —CH$_2$—CF$_2$—CF$_3$ or —CH(CF$_3$)$_2$.

12. A resist composition for immersion exposure, comprising a base component (A) that exhibits changed solubility in an alkali developing solution under action of acid, an acid generator component (B) that generates acid upon exposure, and a fluorine-containing compound according to claim 10.

13. A fluorine-containing compound represented by general formula (c-1-2) shown below:

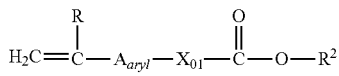
(c-1-2)

wherein each R independently represents a hydrogen atom, a lower alkyl group or a halogenated lower alkyl group; $A_{aryl}$ represents an aromatic cyclic group which may have a substituent and contains a naphthalene ring; $X_{01}$ represents, an alkylene group of 1 to 10 carbon atoms, —O—, —C(=O)—, —C(=O)—O—, a carbonate bond (—O—C(=O)—O—), —NH—C(=O)—, or a combination of these groups; and each $R^2$ independently represents a fluorinated hydrocarbon group having 1 to 5 carbon atoms.

14. A resist composition for immersion exposure, comprising a base component (A) that exhibits changed solubility in an alkali developing solution under action of acid, an acid generator component (B) that generates acid upon exposure, and a fluorine-containing compound according to claim 13.

15. The fluorine-containing compound according to claim 13, wherein each $R^2$ independently represents —CH$_2$—CF$_3$, —CH$_2$—CF$_2$—CF$_3$ or —CH(CF$_3$)$_2$.

16. The resist composition for immersion exposure according to claim 14, wherein said base component (A) is a base component that exhibits increased solubility in an alkali developing solution under action of acid.

17. The resist composition for immersion exposure according to claim 16, wherein said base component (A) comprises a resin component (A1) that exhibits increased solubility in an alkali developing solution under action of acid, and said resin component (A1) comprises a structural unit (a1) derived from an acrylate ester containing an acid dissociable, dissolution inhibiting group.

18. The resist composition for immersion exposure according to claim 17, wherein said resin component (A1) further comprises a structural unit (a2) derived from an acrylate ester containing a lactone-containing cyclic group.

19. The resist composition for immersion exposure according to claim 17, wherein said resin component (A1) further comprises a structural unit (a3) derived from an acrylate ester containing a polar group-containing aliphatic hydrocarbon group.

20. The resist composition for immersion exposure according to claim 14, further comprising a nitrogen-containing organic compound (D).

21. A method of forming a resist pattern, comprising: forming a resist film using a resist composition for immersion exposure according to claim 14, subjecting said resist film to immersion exposure, and subjecting said resist film to alkali developing to form a resist pattern.

22. A fluorine-containing compound comprising a structural unit represented by general formula (c-1-4) shown below:

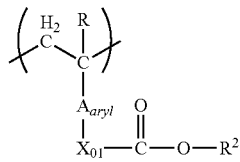
(c-1-4)

wherein each R independently represents a hydrogen atom, a lower alkyl group or a halogenated lower alkyl group; X represents a linear or branched aliphatic hydrocarbon group, a monocyclic group having 2 hydrogen atoms removed therefrom, adamantane having 2 hydrogen atoms removed therefrom, isobornane having 2 hydrogen atoms removed therefrom, tricyclodecane having 2 hydrogen atoms removed therefrom, tetracyclododecane having 2 hydrogen atoms removed therefrom, a divalent aromatic hydrocarbon group, —O—, —C(=O)—, —C(=O)—O—, a carbonate bond (—O—C(=O)—O—), —NH— —NR$^{04}$— wherein $R^{04}$ represents an alkyl group, or a combination of a linear, branched or cyclic aliphatic hydrocarbon group or a divalent aromatic hydrocarbon group with any of —O—, —C(=O)—, —C(=O)—O—, a carbonate bond (—O—C(=O)—O—), —NH—, —NR$^{04}$—, wherein $R^{04}$ represents an alkyl group; $A_{aryl}$ represents an aromatic cyclic group which may have a substituent and contains a naphthalene ring; $X_{01}$ represents, an alkylene group of 1 to 10 carbon atoms, —O—, —C(=O)—, —C(=O)—O—, a carbonate bond (—O—C(=O)—O—), —NH—C(=O)—, or a combination of these groups; and each $R^2$ independently represents a fluorinated hydrocarbon group having 1 to 5 carbon atoms.

23. A resist composition for immersion exposure, comprising a base component (A) that exhibits changed solubility in an alkali developing solution under action of acid, an acid generator component (B) that generates acid upon exposure, and a fluorine-containing compound according to claim 22.

24. The fluorine-containing compound according to claim 22, wherein each $R^2$ independently represents —CH$_2$—CF$_3$, —CH$_2$—CF$_2$—CF$_3$ or —CH(CF$_3$)$_2$.

25. A fluorine-containing compound represented by general formula (c-1-1) shown below:

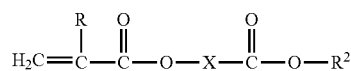
(c-1-1)

wherein each R independently represents a hydrogen atom, a lower alkyl group or a halogenated lower alkyl group; X represents a linear or branched aliphatic hydrocarbon group, a monocyclic group having 2 hydrogen atoms removed therefrom, adamantane having 2 hydrogen atoms removed therefrom, isobornane having 2 hydrogen atoms removed therefrom, tricyclodecane having 2 hydrogen atoms removed therefrom, tetracyclododecane having 2 hydrogen atoms removed therefrom, a divalent aromatic hydrocarbon group, —O—, —C(=O)—, —C(=O)—O—, a carbonate bond (—O—C(=O)—O—), —NH—, —NR$^{04}$— or a combination of a linear, branched or cyclic aliphatic hydrocarbon group or a divalent aromatic hydrocarbon group with any of —O—, —C(=O)—, —C(=O)—O—, a carbonate bond (—O—C(=O)—O—), —NH—, —NR$^{04}$—, wherein R$^{04}$ represents an alkyl group; and R$^2$ represents a linear fluorinated hydrocarbon group of 1 to 5 carbon atoms.

26. A fluorine-containing compound comprising a structural unit represented by general formula (c-1-3) shown below:

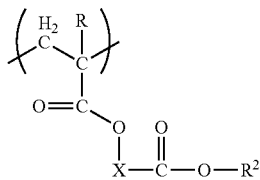

(c-1-3)

wherein each R independently represents a hydrogen atom, a lower alkyl group or a halogenated lower alkyl group; X represents a linear or branched aliphatic hydrocarbon group, a monocyclic group having 2 hydrogen atoms removed therefrom, adamantane having 2 hydrogen atoms removed therefrom, isobornane having 2 hydrogen atoms removed therefrom, tricyclodecane having 2 hydrogen atoms removed therefrom, tetracyclododecane having 2 hydrogen atoms removed therefrom, a divalent aromatic hydrocarbon group, —O—, —C(=O)—, —C(=O)—O—, a carbonate bond (—O—C(=O)—O—), —NH—, —NR$^{04}$— or a combination of a linear, branched or cyclic aliphatic hydrocarbon group or a divalent aromatic hydrocarbon group with any of —O—, —C(=O)—, —C(=O)—O—, a carbonate bond (—O—C(=O)—O—), —NH—, —NR$^{04}$—, wherein R$^{04}$ represents an alkyl group; and R$^2$ represents a linear fluorinated hydrocarbon group of 1 to 5 carbon atoms.

27. A fluorine-containing compound represented by general formula (c-1-1) shown below:

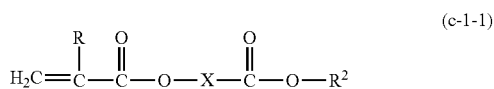

(c-1-1)

wherein each R independently represents a hydrogen atom, a lower alkyl group or a halogenated lower alkyl group; X represents a methylene group, and R$^2$ represents a branched fluorinated hydrocarbon group of 1 to 5 carbon atoms.

28. A fluorine-containing compound comprising a structural unit represented by general formula (c-1-3) shown below:

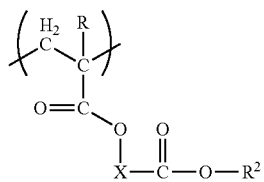

(c-1-3)

wherein each R independently represents a hydrogen atom, a lower alkyl group or a halogenated lower alkyl group; X represents a methylene group; and R$^2$ represents a branched fluorinated hydrocarbon group of 1 to 5 carbon atoms.

* * * * *